US011541119B2

(12) United States Patent
Kundra

(10) Patent No.: US 11,541,119 B2
(45) Date of Patent: *Jan. 3, 2023

(54) TUMOR TREATMENT METHODS USING CELLS THAT LOCALIZE TO THE TUMOR

(71) Applicant: Vikas Kundra, Bethesda, MD (US)

(72) Inventor: Vikas Kundra, Bethesda, MD (US)

(73) Assignee: Vikas Kundra, Bethesda, MD (US)

( * ) Notice: Subject to any disclaimer, the term of this patent is extended or adjusted under 35 U.S.C. 154(b) by 474 days.

This patent is subject to a terminal disclaimer.

(21) Appl. No.: 16/659,986

(22) Filed: Oct. 22, 2019

(65) Prior Publication Data

US 2020/0038512 A1 Feb. 6, 2020

Related U.S. Application Data

(62) Division of application No. 15/647,840, filed on Jul. 12, 2017, now Pat. No. 10,493,162, which is a division of application No. 13/821,541, filed as application No. PCT/US2011/050803 on Sep. 8, 2011, now Pat. No. 9,731,023.

(60) Provisional application No. 61/380,920, filed on Sep. 8, 2010.

(51) Int. Cl.

| | |
|---|---|
| *A61K 47/46* | (2006.01) |
| *A61K 35/28* | (2015.01) |
| *A61K 38/17* | (2006.01) |
| *A61K 38/31* | (2006.01) |
| *A61K 47/64* | (2017.01) |
| *A61K 47/69* | (2017.01) |
| *A61K 51/00* | (2006.01) |
| *A61K 51/08* | (2006.01) |
| *C07K 14/71* | (2006.01) |
| *C12N 15/88* | (2006.01) |

(52) U.S. Cl.
CPC .............. *A61K 47/46* (2013.01); *A61K 35/28* (2013.01); *A61K 38/179* (2013.01); *A61K 38/31* (2013.01); *A61K 47/6425* (2017.08); *A61K 47/6901* (2017.08); *A61K 51/00* (2013.01); *A61K 51/083* (2013.01); *A61K 51/088* (2013.01); *C07K 14/71* (2013.01); *C12N 15/88* (2013.01)

(58) Field of Classification Search
None
See application file for complete search history.

(56) References Cited

U.S. PATENT DOCUMENTS

| | | | |
|---|---|---|---|
| 5,723,299 A | 3/1998 | Bell | |
| 8,278,066 B2 | 10/2012 | Kundra | |
| 9,791,023 B2 * | 10/2017 | Hwang | ............... F16H 3/66 |
| 2002/0173626 A1 | 11/2002 | Kundra | |

FOREIGN PATENT DOCUMENTS

| | | |
|---|---|---|
| EP | 1 118 336 | 7/2001 |
| WO | WO 2006/099019 | 9/2006 |
| WO | WO 2008/085564 | 7/2008 |

OTHER PUBLICATIONS

"Immune Cells," National Institutes of Health, http://www.niaid.nih.gov/topics/immunesystem/immunecells/pages/default.aspx, downloaded Nov. 13, 2014.
"Phagocytes," National Institutes of Health, http://www.niaid.nih.gov/topics/immuneSystem/immuneCells/Pages/phagocytes.aspx, downloaded Nov. 13, 2014.
"Somatic Cell," Wikipedia, http://en.wikipedia.org/wiki/Somatic_cell, downloaded Nov. 13, 2014.
Akinlolu et al., "Antiproliferative effects of $^{111}$In- or $^{177}$Lu-DOTATOC on cells exposed to low multiplicity-of-infection double-deleted vaccinia virus encoding somatostatin subtype-2 receptor," *Cancer Biotherapy and Radiopharmaceuticals*, 25(3):325-333, 2010.
Andreesen et al., "Adoptive immunotherapy of cancer using monocyte-derived macrophages: rationale, current status, and perspectives," *Journal of Leukocyte Biology*, 64:419-426, 1998.
Brower, "Search and Destroy: Recent Research Exploits Adult Stem Cell's Attraction to Cancer," *J. Natl. Cancer Inst.*, 97(6):414-416, 2005.
Dwyer et al., "Advances in mesenchymal stem cell-mediated gene therapy for cancer," *Stem Cell Research & Therapy*, 1:25, 2010.
Extended European Search Report issued in European Application No. 11824117.3, dated Apr. 13, 2015.
Gajewski et al., "Innate and adaptive immune cells in the tumor microenvironment," *Nat. Immunol.*, 14:1014-1022, 2013.
Gambhir et al., "Assays for noninvasive imaging of reporter gene expression", *Nucl. Med. Biol.*, 26:481-490, 1999.
Han et al., "Signalling Can be Uncoupled from Imaging of the Somatostatin Receptor Type 2," *Mol. Imaging*, 6(6):427-437, 2007.
Harrower et al., "The emerging technologies of neutral xenografting and stem cell transplantation for treating neurodegenerative disorders," *Drugs Today*, 40(2):171-189, 2004.
Hung et al., "Mesenchymal stem cell targeting of microscopic tumors and tumor stroma development monitored by noninvasive in vivo positron emission tomography imaging", *Clin Cancer Res.*, 11(21):7749-7755, 2005.
Krüger et al., "Immune based therapies in cancer," *Histology and Histopathology*, 22:687-696, 2007.
Lopez et al., "Neuronal nitric oxide synthase is a SHP-1 substrate involved in sst2 somatostatin receptor growth inhibitory signaling", *FASEB. J.*, 15:2300-2302, 2001.

(Continued)

*Primary Examiner* — Robert M Kelly
(74) *Attorney, Agent, or Firm* — Parker Highlander PLLC

(57) ABSTRACT

Methods and composition for cell-based therapy as well as somatostatin receptor-based therapy are described. For example, in certain aspects methods for administering an anti-tumor therapy using a signaling defective somatostatin receptor mutant are described. Furthermore, the invention provides compositions and methods involve a somatostatin constitutively active somatostatin receptor mutant.

13 Claims, 14 Drawing Sheets
(9 of 14 Drawing Sheet(s) Filed in Color)
Specification includes a Sequence Listing.

(56) References Cited

OTHER PUBLICATIONS

Matthews et al., "Identifying the safety profile of Ad5.SSTR/TK. RGD, a novel infectivity-enhanced bicistronic adenovirus, in anticipation of a phase I clinical trial in patients with recurrent ovarian cancer", *Clin Cancer Res.*, 15:4131-4137, 2009.
Mearadji et al., "Somatostatin receptor gene therapy comined with targeted therapy with radiolabeled octreotide", *Annals of Surgery*, 236(6):722-729, 2002.
Office Action issued in Brazilian Application No. BR112013005711-4, dated Dec. 22, 2020.
Office Action issued in Canadian Application No. 2,810,838, dated Jun. 23, 2017.
Office Action issued in Canadian Application No. 2,810,838, dated Mar. 29, 2018.
Office Action issued in Canadian Application No. 2,810,838, dated Mar. 11, 2019.
Office Action issued in Canadian Application No. 2,810,838, dated Mar. 17, 2020.
Office Action issued in European Application No. 11824117.3, dated Sep. 26, 2017.
Office Action issued in European Application No. 11824117.3, dated Sep. 4, 2020.
Office Action issued in European Application No. 11824117.3, dated Jan. 31, 2020.
Office Action issued in European Application No. 11824117.3, dated Mar. 13, 2019.
Office Action issued in European Application No. 11824117.3, dated Aug. 21, 2018.
Office Action issued in Indian Application No. 2330/DELNP/2013, dated Jun. 13, 2018.
Office Action issued in U.S. Appl. No. 13/821,541, dated Apr. 17, 2014.
Office Action issued in U.S. Appl. No. 13/821,541, dated Dec. 9, 2014.
Office Action issued in U.S. Appl. No. 13/821,541, dated Jun. 30, 2014.
Office Action issued in U.S. Appl. No. 13/821,541, dated Nov. 26, 2014.
Office Action issued in U.S. Appl. No. 15/647,840, dated Mar. 29, 2019.
Office Action issued in U.S. Appl. No. 15/647,840, dated Nov. 2, 2018.
PCT International Preliminary Report on Patentability issued in International Application No. PCT/US2011/050803, dated Feb. 1, 2013.
PCT International Search Report and Written Opinion issued in International Application No. PCT/US2011/050803, dated Apr. 27, 2012.
Rogers et al., "In vivo localization of [111In]-DTPA-d-Phe-octreotide to human ovarian tumor xenografts induced to express the somatostatin receptor subtype 2 using an adenoviral vector", *Clin Cancer Res.*, 5:383-393, 1999.
Schmid and Varner, "Myeloid cell trafficking and tumor angiogenesis," *Cancer Letters*, 250:1-8, 2007.
Schwartkop et al., "Agonist-independent internalization and activity of a c-terminally truncated somatostatin receptor subtype 2 ($\Delta$349)", *Journal of Neurochemistry*, 72(3):1275-1282, 1999.
Sutlu and Alici et al., "Natural killer cell-based immunotherapy in cancer: current insights and future prospects," *Journal of Internal Medicine*, 266:154-181, 2009.
Wei et al., "Glioma-Associated Cancer-Initiating Cells Induce Immunosuppression," *Clin. Cancer Res.*, 16(2):461-473, 2010.
Wels et al., "Migratory neighbors and distant invaders: tumor-associated niche cells," *Genes Dev.*, 22:559-574, 2008.

\* cited by examiner

TUMOR TREATMENT METHODS USING CELLS THAT LOCALIZE TO THE TUMOR

This application is a divisional of U.S. application Ser. No. 15/647,840, filed Jul. 12, 2017, now U.S. Pat. No. 10,493,162, which is a divisional of U.S. application Ser. No. 13/821,541, filed Jun. 26, 2013, now U.S. Pat. No. 9,731,023, which is a national phase application under 35 U.S.C. § 371 of International Application No. PCT/US2011/050803, filed Sep. 8, 2011, which claims priority to U.S. Application No. 61/380,920 filed on Sep. 8, 2010, the entire content of each of which is hereby incorporated by reference in its entirety.

BACKGROUND OF THE INVENTION

1. Field of the Invention

The present invention relates generally to the field of molecular biology, cell therapy, gene therapy, and cancer therapy. More particularly, it concerns methods for treatment of a subject by administration of cells comprising somatostatin receptor such as a signaling deficient somatostatin receptor mutant. The invention also generally pertains to methods for therapy that involves constitutively active somatostatin receptor mutants.

2. Description of Related Art

Therapeutic treatment of many human disease states is limited by the systemic toxicity of the therapeutic agents used. Cancer therapeutic agents in particular exhibit a very low therapeutic index, with rapidly growing normal tissues such as skin and bone marrow typically affected at concentrations of agent that are not much higher than the concentrations used to kill tumor cells. For example, gene therapy and cellular therapies have great promise, but they suffer from a lack of methodology for specifically targeting and localization of a gene therapy and/or a cell expressing a recombinant nucleic acid within an organism. Treatment and diagnosis of cancer would be greatly facilitated by the development of compositions and methods for targeted delivery to cancer cells.

Somatostatin receptors are known to be expressed in a large number of human tumors and represent the basis for in vivo tumor targeting. However, not all tumors express somatostatin receptors. In a pre-clinical tumor model, a recombinant somatostatin receptor type 2 (SSTR2) chimera can serve as a reporter gene of gene expression that can be quantified in vivo and can also serve as a growth inhibitor when targeting cancer. However, this SSTR-mediated signaling, such as growth inhibition, may or may not be desirable in different therapy purposes wherein the SSTR-specific targeting is envisioned.

Therefore, there exists a need of novel methods for targeted therapy, especially cancer therapy.

SUMMARY OF THE INVENTION

Aspects of the present invention overcome a major deficiency in the art by providing novel methods and compositions for treating a disease or a condition with cell therapy, gene therapy, radiotherapy, additional anti-tumor therapy, or a combination thereof.

For targeted cellular therapy, cells having an exogenous expression construct may be delivered to a disease site, such as a tumor, and a therapeutic may target the cells and exert a bystander therapeutic effect to the tumor. For example, a radiotherapeutic may bind the delivered cells, more specifically, the exogenous expressed product in the delivered cells, and kill the neighboring tumor by bystander effect. Alternatively, a thermal therapeutic such as a photothermal therapeutic that bind the delivered cells may kill the neighboring cells upon activation, such as laser-activatable nanoparticles.

In particular aspects, the treatment methods may be based on somatostatin receptor or its signaling mutants. The signaling mutants may comprise signaling defective mutants or constitutively active mutants. They can be used either on their own or with other agents for therapy. The invention is in part based on the discovery that a radioligand can be therapeutically effective even in cells expressing a signaling deficient SSTR mutant. Radiotherapy has been used to target tumors endogenously expressing SSTR or after gene transfer of wild-type SSTR, but not mutant receptors. The advantages of an SSTR-binding therapeutic such as a radioligand used in combination with an SSTR mutant include, but are limited to, augmentation of the effect of a growth inhibiting mutant, bystander effect, and enablement of cellular therapy using a signaling deficient reporter. In some cell types, SSTR-mediated signaling may not reconstitute, for example, for growth inhibition; tumor growth may be inhibited by other mechanisms such as radiation-induced damage in cells without functional SSTR signaling but expressing SSTR's. It also enables use of agents that may not activate SSTR signaling but bind SSTR's such as antagonists or binding agents that are neither agonists or antagonists.

Accordingly, in a first embodiment there is provided a method of treating a tumor using a somatostatin receptor such as a signaling defective somatostatin receptor mutant for tumor targeting and therapy. Such a method may be a cell-based therapy, a gene therapy, a radiotherapy, a chemotherapy, an immunotherapy, or a combination thereof.

In the aspects of a cell-based therapy, the method may comprise providing one or more cells capable of localizing to a tumor. The cells may comprise an expression construct comprising a nucleic acid sequence encoding a somatostatin receptor (SSTR) mutant. In a preferred aspect, the mutant may be a signaling defective mutant to avoid the growth inhibition of delivery cells via a normal somatostatin receptor-mediated signaling. The method may further comprise introducing the cells to a subject having a tumor. Introducing the cells to the subject can be by any method known to those of ordinary skill in the art. For a targeted therapy, the method may further comprise administering to the subject an anti-tumor therapeutic that specifically binds the somatostatin receptor or the cells introduced into the subject and effects a damage on the tumor, for example, through a bystander effect. The therapeutic may be coupled to a ligand that specifically binds the somatostatin receptor, which may be the native form, the signaling defective or constitutively active somatostatin receptor mutant for tumor targeting. The anti-tumor therapeutic may kill the tumor cells which might not express the SSTR by a bystander effect, such as radiotherapy.

In a further aspect, if the delivered cells or their progeny cells become malignant these cells expressing mutant SSTR may be treated with a therapy targeting the expressed mutant SSTR. This additional benefit serves as an important safeguard against undesired effects of cellular therapy.

In the aspects of a gene therapy, there may be provided a treatment method comprising providing an expression construct comprising a nucleic acid sequence encoding a signaling altered somatostatin receptor mutant, particularly a constitutively active mutant, and introducing the expression construct into the tumor, for example, directly (e.g., via intratumoral injection) or by a tumor targeting moiety-encoding sequence comprised in the expression construct. The signaling altered mutant may have reduced or enhanced signaling as compared with a native receptor, such as a signaling defective mutant or a constitutively active mutant. The mutant may have transmembrane domains III-VII of a native receptor, therefore retaining the ability to bind a native ligand or an analog.

The method may further comprise administering to the subject an anti-tumor therapeutic coupled to a ligand that specifically binds the somatostatin receptor or its mutant. A "targeting moiety" is a term that encompasses various types of affinity reagents that may be used to enhance the localization or binding of a substance to a particular location in an animal, including organs, tissues, particular cell types, diseased tissues or tumors. Targeting moieties may include peptides, peptide mimetics, polypeptides, antibodies, antibody-like molecules, nucleic acids, aptamers, and fragments thereof.

Such a mutant may have at least trans-membrane domains III-VII of a native somatostatin receptor, which may be responsible for binding to its native ligand or any known SSTR binding partners. The mutant may have a mutation that diminishes or eliminates the ability to inhibit cellular growth as compared with a native receptor. The mutant may have a C-terminal deletion. The deletion may include a deletion of an intracellular signaling domain. For example, such a C-terminal deletion include deletion of an amino acid sequence with at least about 80, 85, 90, 95, 99, 99.5, or 100% homology (or any intermediate ranges) to a C-terminal 55-amino acid sequence of human SSTR2 (i.e., amino acid positions 315 to 349 of SEQ ID NO:6) as compared with a corresponding native somatostatin receptor. The mutant may be a truncated mutant, such as a somatostatin receptor that is truncated carboxy terminal to amino acid position 314, particularly human SSTR2 delta 314, which is a human SSTR truncated carboxy terminal to amino acid 314 (having the sequence of amino acids 1-314 of SEQ ID NO:6).

The mutant may be a mutant of a somatostatin receptor type 1, 2, (2A, 2B), 3, 4, or 5. In further particular embodiments, the mutant is a somatostatin receptor type 2 (SSTR2) mutant. The mutant may be a mutant of a somatostatin receptor of human, mice, rat, primates, or any other mammals. The mutant can be truncated at either the N-terminus or the C-terminus. In some embodiments, there is a truncation at both the N-terminus and the C-terminus. In certain embodiments, the mutant has altered signaling including being signaling defective, altered internalization, or a combination thereof. Altered signaling may include an increase in signaling, a decrease in signaling, or an inciting of signaling pathways different from those incited by the native receptor.

The cell that is so provided can be any cell known to those of ordinary skill in the art, but in particular embodiments the cell is a stem cell or an immune cell. A "stem cell" generally refers to any cell that has the ability to divide for indefinite periods of time and to give rise to specialized cells. In particular aspects, the invention takes advantage of the tendency for tumors, especially invasive tumors, to attract stem cells or immune cells such as white blood cells. Stem cells thus have the ability to localize to and be incorporated into tumors.

For example, the stem cell can be an embryonic stem cell, a somatic stem cell, a germ stem cell, an epidermal stem cell, or a tissue-specific stem cell. Examples of tissue-specific stem cells include, but are not limited to, a neural stem cell, a keratinocyte stem cell, a renal stem cell, a embryonic renal epithelial stem cell, an embryonic endodermal stem cell, a hepatocyte stem cell, a mammary epithelial stem cell, a bone marrow-derived stem cell, a skeletal muscle stem cell (satellite cell), a limbal stem cell, a hematopoietic stem cell, a mesenchymal stem cell, peripheral blood mononuclear progenitor cell, a splenic precursor stem cell, and an oesophageal stem cell.

In some other aspects, the cells may be immune cells. The immune cell may traffic to the tumor by antigen-specific localization. An "immune cell" is any cell associated with generation of an immune response, such as a monocyte, a granulocyte, or a lymphocyte. An "immune cell" is defined herein to refer to a cell that recognizes and responds against microorganisms, viruses, and substances recognized as foreign and potentially harmful to the body. The granulocyte may be a neutrophil, a basophil, or an eosinophil. The lymphocyte may be a T cell, a B cell, or a NK cell. The immune cell may be a stem cell whose progeny includes any of the aforementioned cells associated with generation of an immune response. Particular examples of immune cells include T cells and B cells.

The immune cells may be active against tumor cells expressing a particular antigen. The immune cells may be engineered to localize to a tumor expressing an antigen that bind the immune cells. Methods of therapy involving immune cells involve techniques well-known to those of ordinary skill in the art.

The cell can be obtained from any source, both natural and artificial. For example, the cell is a mammalian cell, more specifically, a human cell or a mouse cell. In some embodiments, the cell is an autologous cell. For example, the cell may be a stem cell obtained from a subject, wherein the cell is reintroduced into the subject following the transfer into the cell of the expression construct. In other embodiments, the cell is an allogeneic cell, or a cell obtained from a subject that is distinct from the subject to whom the cell is introduced, but from the same species. In still further embodiments, the cell is a xenogeneic stem cell, or a cell from a different species than the recipient subject.

For example, introducing the cell to the subject may involve intravenous administration, intracardiac administration, intradermal administration, intralesional administration, intrathecal administration, intracranial administration, intrapericardial administration, intraumbilical administration, intraocular administration, intraarterial administration, intraperitoneal administration, intraosseous administration, intrahemmorhage administration, intratrauma administration, intratumor administration, subcutaneous administration, intramuscular administration, intravitreous administration, direct injection into a normal tissue or organ, direct injection into a diseased tissue or organ like a tumor, topical administration, or any other method of local or systemic administration known to those of ordinary skill in the art.

In some embodiments, the nucleic acid includes more than one coding region. For example, the nucleic acid may include a second coding region. For example, the second coding region may be a protein tag gene, a reporter gene, a therapeutic gene, a signaling sequence, or a trafficking sequence. Information regarding somatostatin fusion proteins can be found in U.S. Patent App. Pub. No. 20020173626, herein specifically incorporated by reference. A particular example of a fusion protein may be a sequence expressing both an SSTR mutant and a reporter gene, such as an SSTR mutant linked to a luciferase.

The term "reporter," "reporter gene" or "reporter sequence" as used herein refers to any genetic sequence or encoded polypeptide sequence that is detectable and distinguishable from other genetic sequences or encoded polypeptides present in cells. A "therapeutic gene" as used herein refers to any genetic sequence or encoding polynucleotide sequence that is known or suspected to be of benefit in the treatment or prevention of disease in a subject. A "signaling sequence" is defined herein to refer to any genetic sequence or encoded polynucleotide sequence that is involved in signal transduction or cell differentiation. A "trafficking sequence" as used herein refers to any genetic sequence or encoded polypeptide sequence that is involved in the transit of cells from one site in a subject to a different site in the subject. Reporter sequences, therapeutic genes, signaling sequences, and trafficking sequences are well-known to those of ordinary skill in the art, and are discussed at length elsewhere in this specification.

In some embodiments, the first coding region and the second coding region are linked by an IRES or a bidirectional promoter sequence. A "bidirectional promoter sequence" refers to a control sequence that is a region of a nucleic acid sequence at which initiation and rate of transcription of both the first and the second coding region are controlled. One of ordinary skill in the art would be familiar with bidirectional promoter sequences, such as those set forth in Trinklein et al., 2004 and at world wide web via stanford.eduMdschroed/bidirectionallindex.shtml.)

The nucleic acid encoding a somatostatin receptor or its mutant may be operably linked to a first promoter. In certain aspects, a second promoter sequence is operatively linked to the second coding region. A promoter sequence used herein, such as the first promoter sequence and the second promoter sequence, may be any promoter sequence, such as a constitutive promoter sequence, a tissue-specific promoter sequence, a lineage-specific promoter, or a function-specific promoter sequence. For example, the first promoter sequence and the second promoter sequence may be of the same type (e.g., both constitutive promoter sequences) or may differ in type (e.g., first promoter sequence is a constitutive promoter sequence, and second promoter sequence is a tissue-specific promoter sequence).

In further embodiments, the nucleic acid further includes a third coding region. Preferably, the third coding region is operatively linked to a third promoter sequence. The first coding region, the second coding region, and the third coding region may either be independent or operably linked by one or more IRES or bidirectional promoter sequences. The first promoter sequence, the second promoter sequence, and the third promoter sequence may be individually selected from the group consisting of a constitutive promoter sequence, a tissue-specific promoter sequence, a lineage-specific promoter, and a function-specific promoter sequence. As discussed above, the promoter sequences may be of the same type or be of distinct types.

The nucleic acid encoding the somatostatin receptor or its mutant may or may not further comprise a nucleic acid sequence encoding a protein tag. The protein tag may be any protein tag known to those of ordinary skill in the art. A protein tag may be fused to the N-terminal end or C-terminal end of the somatostatin receptor or its mutant. The protein tag may or may not have enzymatic activity. In embodiments wherein the protein tag has enzymatic activity, the protein tag may be, for example, hemagglutinin A, beta-galactosidase, thymidine kinase, transferrin, myc-tag, VP 16, $(His)_6$-tag, FLAG, or chloramphenicol acetyl transferase.

The method may father comprise introducing the expression construct into the cells. The expression construct that is transferred into the cell may or may not be comprised in a delivery vehicle. A "delivery vehicle" is defined herein to refer an entity that associates with a nucleic acid and mediates the transfer of the nucleic acid into a cell. Any delivery vehicle is contemplated by the present invention. In some embodiments, for example, transferring the expression construct into the cell comprises contacting the cell with the delivery vehicle.

For example, the delivery vehicle may include but is not limited to a polypeptide, a lipid, a liposome, lipofectamine, a plasmid, a viral vector, a phage, a polyamino acid such as polylysine, a prokaryotic cell, or a eukaryotic cell. In particular embodiments, the delivery vehicle is a viral vector. The viral vector can be any viral vector known to those of ordinary skill in the art. For example, the viral vector may be a lentiviral vector, a baculoviral vector, a parvovirus vector, a semiliki forest virus vector, a Sindbis virus vector, a lentivirus vector, a retroviral vector, a vaccinia viral vector, an adeno-associated viral vector, a picornavirus vector, an alphavirus vector, or a poxviral vector. In some embodiments, the viral vector is a lentiviral vector. Transferring the expression construct into the cell can be by any method known to those of ordinary skill in the art. For example, transferring the expression construct may involve performing electroporation or nucleofection of the cell in the presence of the expression construct.

In some embodiments, the method further comprises sorting of the cell from other cells following the transfer of the expression construct. "Sorting" refers to separation of a cell containing the expression construct from other cells that do not contain the expression construct. Sorting can be performed by any method known to those of ordinary skill in the art, and may rely on the presence of the expression construct. For example, sorting may be performed by fluorescence activated cell sorting (FACS), column chromatography, and/or magnetic resonance beads.

For tumor treatment, a therapeutic coupled to a ligand that specifically binds to the somatostatin receptor or its mutant may be administered to the subject by targeting the somatostatin receptor or its mutant expressed within or near tumor. An "anti-tumor therapeutic" may be defined herein to refer to a cytotoxic or cytostatic agent. The therapeutic may comprise a therapeutic radionuclide, a chemotherapeutic, a tumor suppressor, an inducer apoptosis, an enzyme, an antibody, an antibody fragment, an siRNA, a hormone, a prodrug, an immunostimulant or any therapeutic that have a bystander effect. In a particular aspect, the therapeutic may be a therapeutic radionuclide, such as a $\beta^-$ particle emitter, for example, $^{177}Lu$ or $^{90}Y$. However, many imaging radionuclides have not be found to be therapeutically effective and may not be used as therapeutic radionuclides, such as $^{111}$-In and $^{99m}Tc$.

In further embodiments, a therapeutic or a detectable moiety is coupled to a ligand that specifically binds the somatostatin receptor or its mutant to localize a therapy or tracking expression. A "ligand" is defined herein to refer to an ion, a peptide, a oligonucleotide, a molecule, or a molecular group that binds to another chemical entity or polypeptide to form a larger complex. For example, in some embodiments, the ligand is a nucleic acid, such as a DNA molecule or an RNA molecule, a protein, a polypeptide, a peptide, an antibody, an antibody fragment, or a small molecule. For example, the ligand may be somatostatin or an analogue thereof, such as octreotate, octreotide, lanreotide, or sandostatin. The ligand may further comprise a chelator molecule, such as 1,4,7,10-tetraazacyclododecane-1,4,7,10-tetraacetic acid (DOTA) or diethylene triamine pentaacetic acid (DTPA). In particular embodiments, the ligand may be [$^{90}$Y-DOTA]-octreotate or [$^{177}$Lu-DOTA]-octreotate.

The method may further comprise tracking the cells or gene expression in the subject. The method may comprise imaging the cells, particularly imaging a reporter encoded by a sequence comprised in the expression construct or a detectable moiety that will bind the somatostatin receptor expressed in the cells. In further embodiments, the method may comprise further administering a detectable moiety couple to a ligand that specifically binds the somatostatin receptor, such as its mutant.

A "detectable moiety" is defined herein to refer to any molecule or agent that can emit a signal that is detectable by imaging. For example, the detectable moiety may be a protein, a radioisotope, a fluorophore, a visible light emitting fluorophore, a near infrared light emitting fluorophore, infrared light emitting fluorophore, a metal, a ferromagnetic substance, a paramagnetic substance, a superparamagnetic substance, an electromagnetic emitting substance, a substance with a specific MR spectroscopic signature, an X-ray absorbing or reflecting substance, a small molecule, or a sound altering substance. In certain particular embodiments, the detectable moiety is a radioisotope. In particular embodiments, the detectable moiety is $^{111}$-In octreotide.

In some embodiments, the method for tracking the location of a cell in a subject further comprises detecting expression of the mutant or the reporter by assaying for an association between the mutant or reporter expressed by the cell and a detectable moiety. For example, the association between the cell and the detectable moiety comprises binding of the detectable moiety by the cell, binding of a ligand operably coupled to the detectable moiety by the cell, cellular uptake of the detectable moiety, or cellular uptake of a ligand operably coupled to the detectable moiety.

Contacting the cell with a detectable moiety may occur either prior to or after the cell is introduced into the subject. In particular embodiments, the cell is contacted with a detectable moiety prior to introduction of the cell into the subject. In some embodiments of the present invention, the cells are contacted with a detectable moiety that binds to the SSTR mutant or the reporter prior to introducing the cells into the subject, and in other embodiments, the cells are contacted with the detectable moiety that binds to the reporter or mutant after the cells are introduced into the subject.

Any imaging technique known to those of ordinary skill in the art can be applied in imaging the detectable moiety. In some embodiments, for example, the imaging technique is an invasive imaging technique. An "invasive imaging technique" is defined herein to refer to any imaging technique that involves removal of tissue from a subject or insertion of a medical device into a subject. Invasive imaging techniques may involve, for example, performance of a biopsy of tissue in conjunction with an imaging technique such as fluorescence microscopy, or insertion of a catheter or endoscope into a subject for purposes of imaging.

In particular embodiments, the imaging technique is a non-invasive imaging technique. A "non-invasive imaging technique" is defined herein as an imaging technique that does not involve removal of tissue from a subject or insertion of a medical device into a subject. One of ordinary skill in the art would be familiar with non-invasive imaging techniques. Examples include MRI, MR spectroscopy, radiography, CT, ultrasound, planar gamma camera imaging, SPECT, PET, other nuclear medicine-based imaging, optical imaging using visible light, optical imaging using luciferase, optical imaging using a fluorophore, other optical imaging, imaging using near infrared light, imaging using infrared light, photoacoustic imaging or thermoacoustic imaging.

In a further aspect, there may be provided a constitutively active human somatostatin receptor mutant, particularly a SSTR type 2 mutant. The constitutively active SSTR could inhibit function such as cell growth or hormone secretion without the need for a ligand. Thus, the cost of the ligand may be saved. Ligands such as clinically used octreotide are contraindicated in some patients and side effects may include inhibition of gastrointestinal and pancreatic function causing digestive problems such as loose stools, nausea, gas, and gallstones and sometimes diabetes and hepatitis. The primary current treatment for acromegaly is somatostatin analogues, octreotide and lanreotide. Signaling constitutively active SSTR gene therapy may both inhibit growth hormone secretion and shrink or eliminate the tumor and an appropriate radioligand may increase efficacy of tumor kill. This paradigm may be used in tumors that express somatostatin receptors such as other neuroendocrine tumors like carcinoid or pancreatic tumors. In addition, the advantage of the gene or cellular therapy approach is that it may be effective in most every tumor, including those that do not normally express somatostatin receptors. The growth suppressing receptor mutant in the constitutively active form could eliminate the need to provide octreotide after gene therapy, making the process less cumbersome, more cost effective, and avoiding toxicity of the octreotide.

The mutant may be a constitutively active form of a native human somatostatin receptor and have a C-terminal deletion. For example, the mutant is an SSTR mutant. In particular, the C-terminal deletion is a deletion of C-terminal amino acids after position 340 (delta 340), such as an SSTR delta 340 mutant having the sequence of amino acids 1-340 of SEQ ID NO:6. There may also be provided an isolated nucleic acid molecule comprising a sequence encoding the mutant and an expression vector (i.e., expression construct) comprising the isolated nucleic acid molecule.

There may further be provided a method of treating a disease or a condition wherein SSTR-mediated signaling is desired or needed, for example, inhibition of cell growth or inhibition of hormone secretion is desired. Non-limiting examples of the disease or condition may include cancer (including growth, angiogenesis, invasion, and apoptosis), glucose regulation (such as hyperglycemia of diabetes), neuronal and neuromuscular transmission, gastric acid secretion, growth (such as acromegaly), and ocular neovascularization.

The method may comprise the steps of: a) providing a therapeutic composition comprising an isolated nucleic acid molecule comprising a sequence encoding a constitutively active SSTR mutant; and b) administering a therapeutically effective amount of the therapeutic composition to the subject. The disease or condition may be a tumor, such as cancer (including growth, angiogenesis, invasion, and apoptosis), glucose regulation (such as hyperglycemia of diabetes), neuronal and neuromuscular transmission, gastric acid secretion, growth (such as acromegaly), and ocular neovascularization For example, the isolated nucleic acid molecule further comprises a second coding sequence, such as a protein tag gene, a reporter gene, a therapeutic gene, a signaling sequence, or a trafficking sequence.

In a further aspect, the method may comprise administering to the subject a therapeutic agent such as an anti-tumor therapeutic coupled to a ligand that specifically binds the somatostatin receptor, particularly a signaling altered somatostatin receptor mutant, such as signaling defective mutant or a constitutively active mutant, depending on whether SSTR-mediated signaling is desired. The isolated nucleic acid molecule may be comprised in a gene delivery vehicle. Examples of a gene delivery vehicle include, but are not limited to, a lipid, a liposome, lipofectamine, a plasmid, a viral vector, a phage, a polyamino acid, a particle, calcium phoshate, or DEAE-dextran. The administration of a gene delivery vehicle may include pulmonary administration, endobronchial administration, topical administration, intraocular administration, parenteral administration, intranasal administration, intratracheal administration, intrabronchial administration, intranasal administration, or subcutaneous administration. For tumor targeting, the isolated nucleic acid molecule may further comprise a tumor-selective promoter or a sequence encoding a tumor targeting moiety.

The subject to be treated may be any animal, such as a human, a mouse, a rat, or any other mammal. The subject may have a tumor such as a neuroendocrine tumor, breast tumor, lung tumor, prostate tumor, ovarian tumor, brain tumor, liver tumor, cervical tumor, colon tumor, renal tumor, skin tumor, head and neck tumor, bone tumor, esophageal tumor, bladder tumor, uterine tumor, lymphatic tumor, stomach tumor, pancreatic tumor, testicular tumor, or lymphoma.

The disease to be treated can be any disease known to those of ordinary skill in the art. For example, the disease may be a hyperproliferative disease, an infectious disease, an inflammatory disease, a degenerative disease, a congenital disease, a genetic disease, an immunological disease, trauma, poisoning, or a disease associated with toxicity. In particular embodiments, the disease is a hyperproliferative disease. The hyperproliferative disease may be benign or malignant. In particular embodiments, the hyperproliferative disease is cancer. The cancer may be any type of cancer. For example, the cancer may be breast cancer, lung cancer, prostate cancer, ovarian cancer, brain cancer, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. In further embodiments, the disease is type I diabetes or type II diabetes.

In still further embodiments, the disease is a cardiovascular disease. For example, the cardiovascular disease may be cardiomyopathy, ischemic cardiac disease, congestive heart failure, congenital cardiac disease, traumatic cardiac disease, toxic cardiac disease, pericarditis, or genetic cardiac disease.

Alternatively, the disease may be a neurological disease, such as Parkinson's disease, Alzheimer disease, amyotrophic lateral sclerosis, or multiple sclerosis. The neurological disease may be a neurodegenerative disease, spinal cord disease, traumatic neurological disease, infectious disease, or inflammatory disease. The disease may also be an immunological disease, such as transplant rejection, autoimmune disease, immune complex disease, vasculitis, or HIV infection.

In particular, the condition to be treated may involve any conditions related to growth hormone (GH) excess, such as acromegaly. Acromegaly is characterized by excessive levels of GH in the blood, often resulting from an adenoma of the anterior pituitary. Acromegaly is associated with significant risk of morbidity (soft-tissue swelling, arthralgia, headache, perspiration, fatigue, CV disorders), insulin resistance and diabetes, vision problems resulting from optic nerve compression by the adenoma, and premature mortality. Most of the biological impacts and symptoms related to GH excess are mediated through IGF-1, which is secreted by the liver as well as many other target organs as a result of GH receptor activation. The growth hormone excess may be related to diseases or conditions involve a gastrointestinal system, neurons, or pituitary gland.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

HT1080 cells (fibrosarcoma cells that do not endogenously express SSTR2) were grown in the presence of 5% FBS with or without 100 nM of the somatostatin analogue sandostatin. Three days later, MTT assay was used to determine cell number. Stable transfectants, wild-type receptor (SSTR2FL) was used as a positive control for ligand responsive growth inhibition and HA-SSTR2D314 does not inhibit growth upon ligand stimulation. HA-SSTR2D351 or HA-SSTR2D340 demonstrated equivalent amounts of expression (data not shown).

Figure 3A:
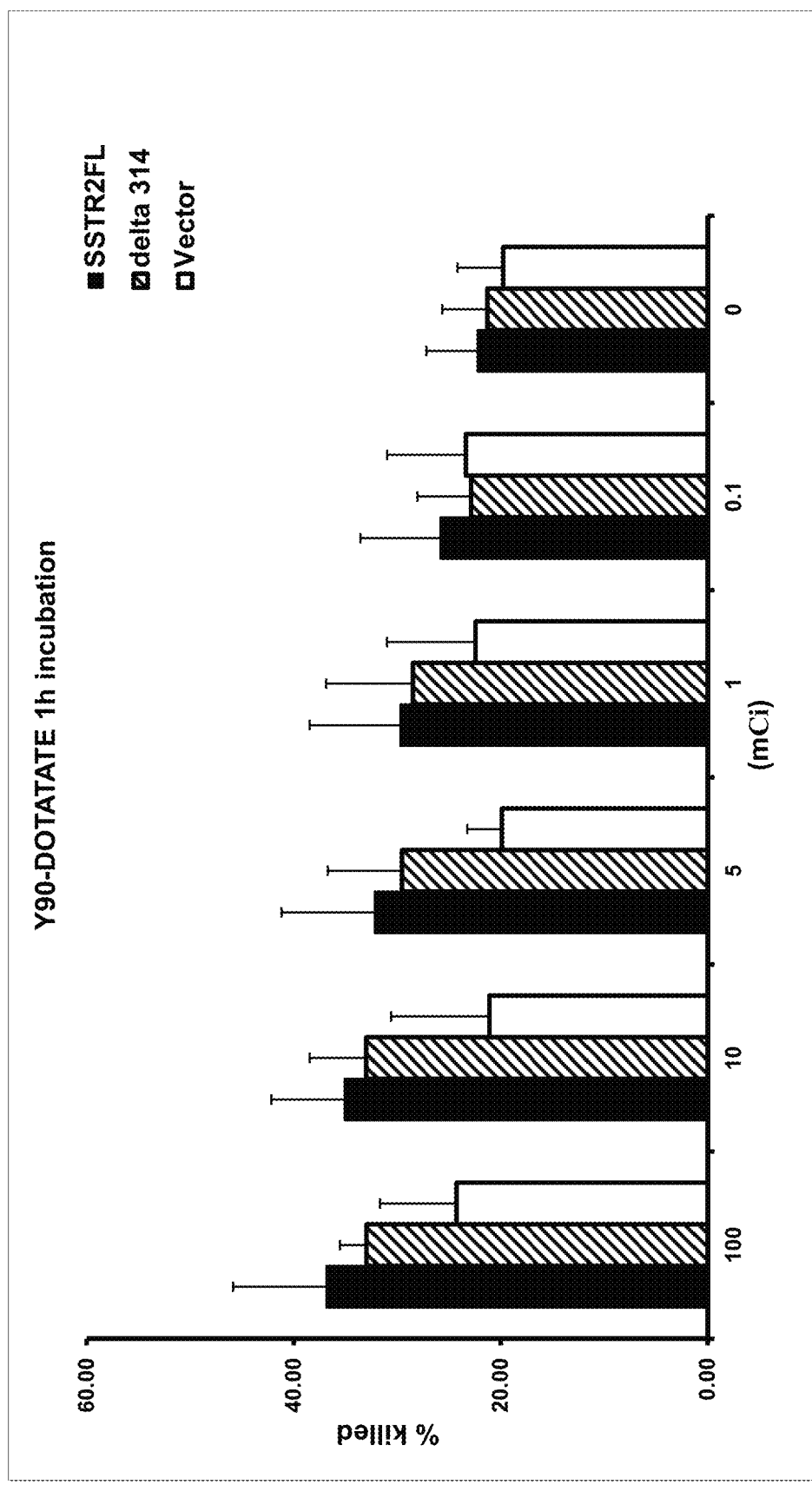
Figure 3B:
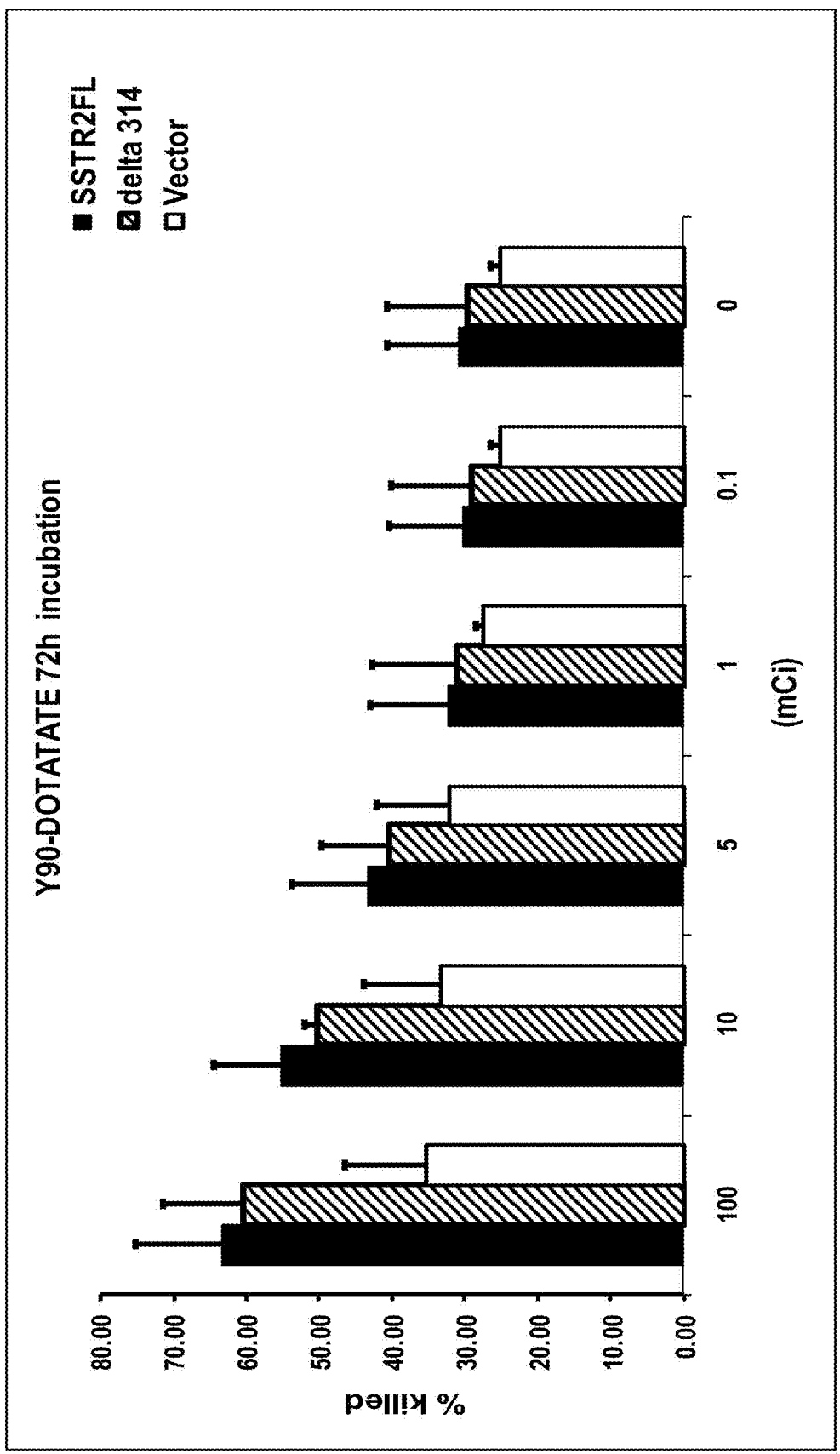

FIGS. 3A-B: Exposure to 90Y-DOTA-octreotate (DOTATATE) results in death of HT1080 cells expressing wild-type or signaling deficient SSTR2 receptors, but not vector transfected cells. Stably transfected HT1080 cells were exposed to different amounts of $^{90}$Y-DOTATATE for 1 hour and 72 hours. Dose dependent and time dependent killing was observed in HT1080 cells expressing wild-type or signaling deficient HA-SSTR2 receptors, but not vector transfected cells. Cell death was assessed by trypan blue uptake. *$p<0.05$ vs Vector.

Figure 4:
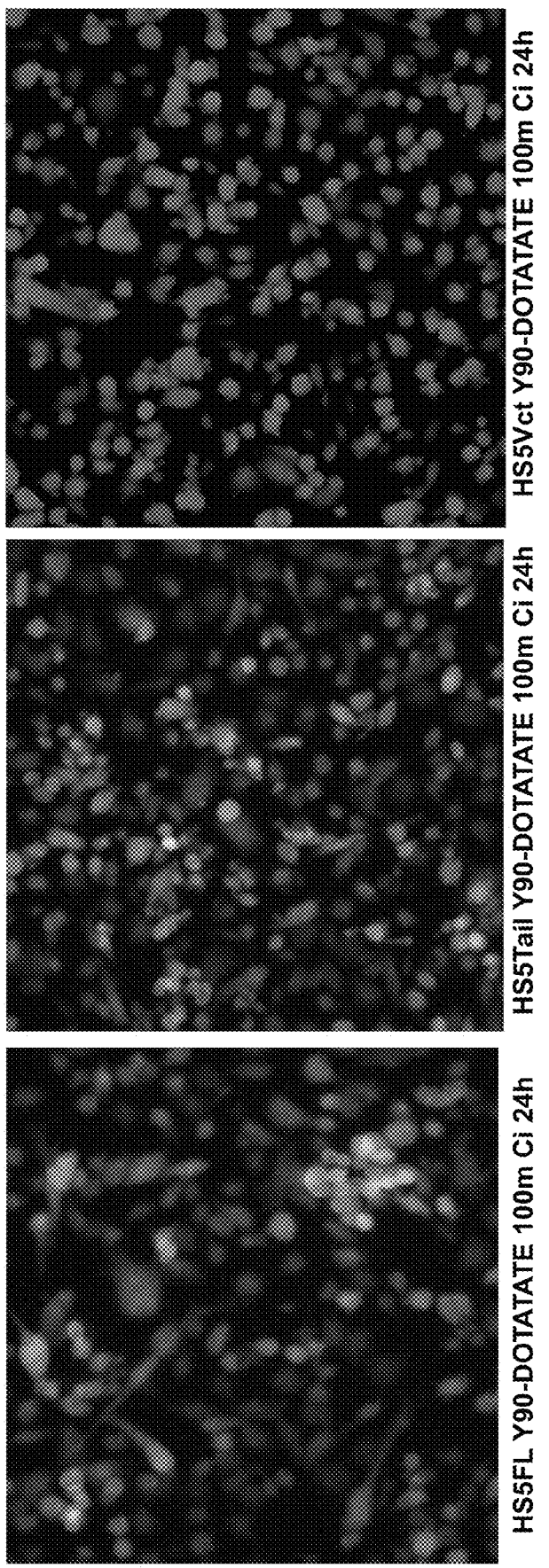

FIG. 4: Exposure to 90Y-DOTA-octreotate (DOTATATE) results in bystander cell death of tumor cells. Human mesenchymal stem cells (HS5) stably expressing wild-type or signaling deficient HA-SSTR2 receptors or transfected with vector were admixed with untransfected HT1080 cells and then exposed to 90Y-DOTATATE for 24 hours. Then, live (green)/dead (red) staining was performed. Rosettes (clusters) of dead cells were seen in wells containing mesenchymal stem cells stably expressing wild-type or signaling deficient HA-SSTR2 receptors but not in wells containing mesenchymal stem cells transfected with vector.

Figure 5:
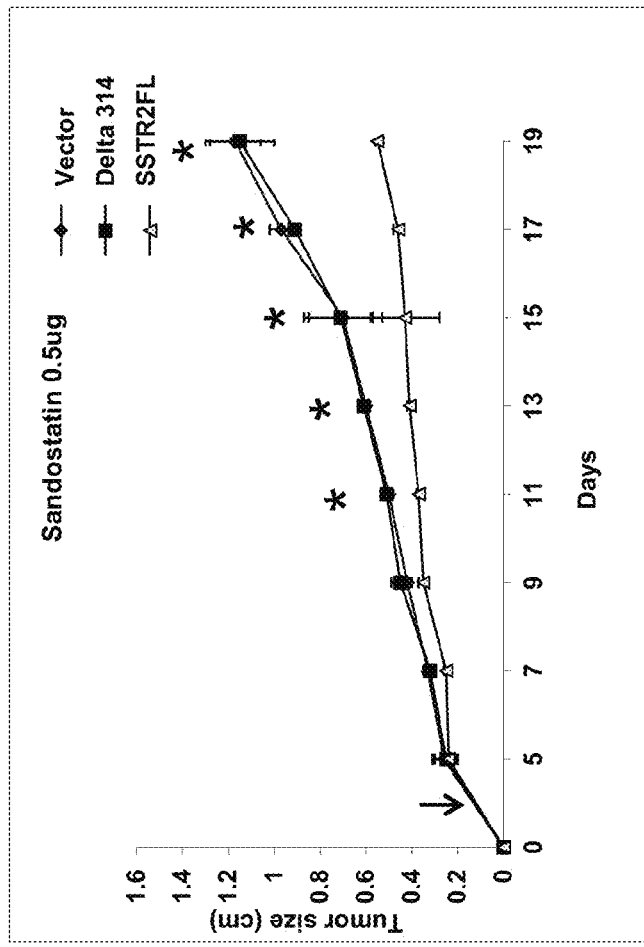
Figure 5:
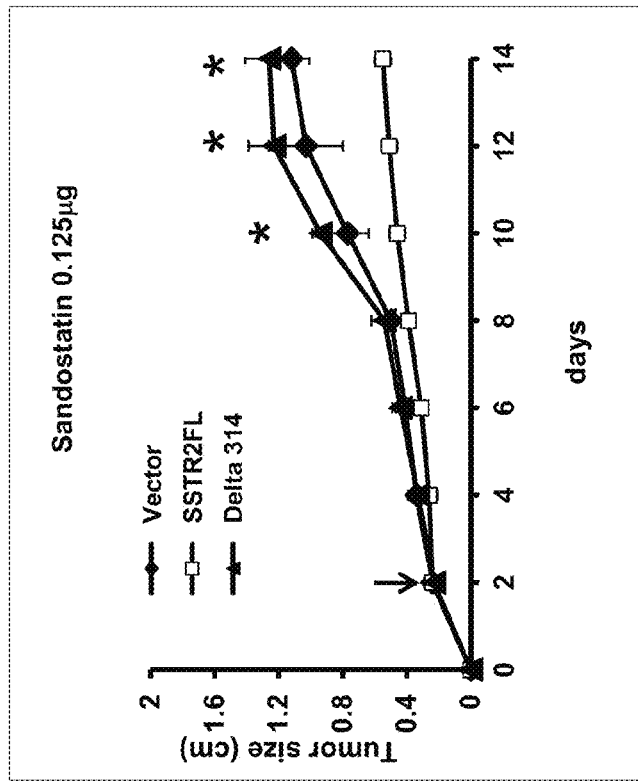

FIG. 5: The somatostatin analogue octreotide inhibited growth of tumors expressing wild-type receptor, but not the signaling deficient receptor or tumors derived from vector transfected cells. Stably transfected HT1080 cells were implanted subcutaneously in nude mice (three tumors, HA-wt, HA-D314, vector, per animal). When tumors were palpable, daily injections of the somatostatin analogue sandostatin were initiated and tumors were measured by calipers every two days. Receptor activation by octreotide inhibited growth of tumors expressing wild-type receptor, but no decrease in tumor size was seen with the signaling deficient receptor. *$p<0.05$ SSTR2FL vs Vector. Thus, receptor activation can result in inhibition of tumor growth.

Figure 6A:
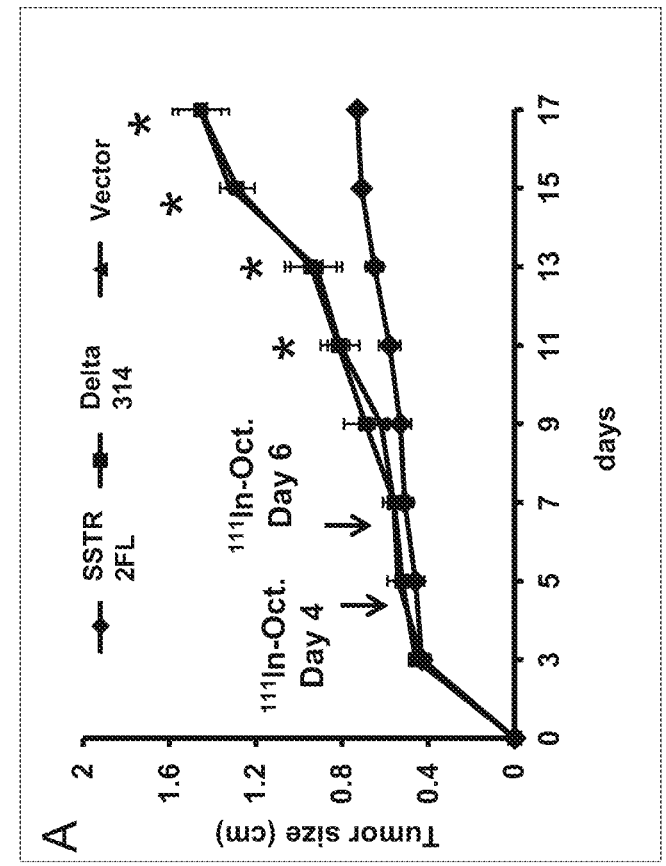

FIG. 6A: High doses of the imaging agent $^{111}$-In-octreotide inhibits tumor growth via the biologic effect of octreotide activating SSTR2 and not the effect of radioactivity (primarily gamma rays) on the tumor. The imaging agent $^{111}$-In-octreotide inhibited growth of tumors expressing the wild-type receptor, but not the signaling deficient receptor or tumors derived from vector transfected cells. Stably transfected HT1080 cells were implanted subcutaneously in nude mice (three tumors, HA-wt, HA-D314, vector, per animal). When tumors were palpable, 0.9 mCi of $^{111}$-In octreotide was given IV on day 4 and day 6. Tumors were measured by calipers every two days. *$p<0.05$ SSTR2FL vs Vector. Thus, receptor activation can result in inhibition of tumor growth.

Figure 6B:
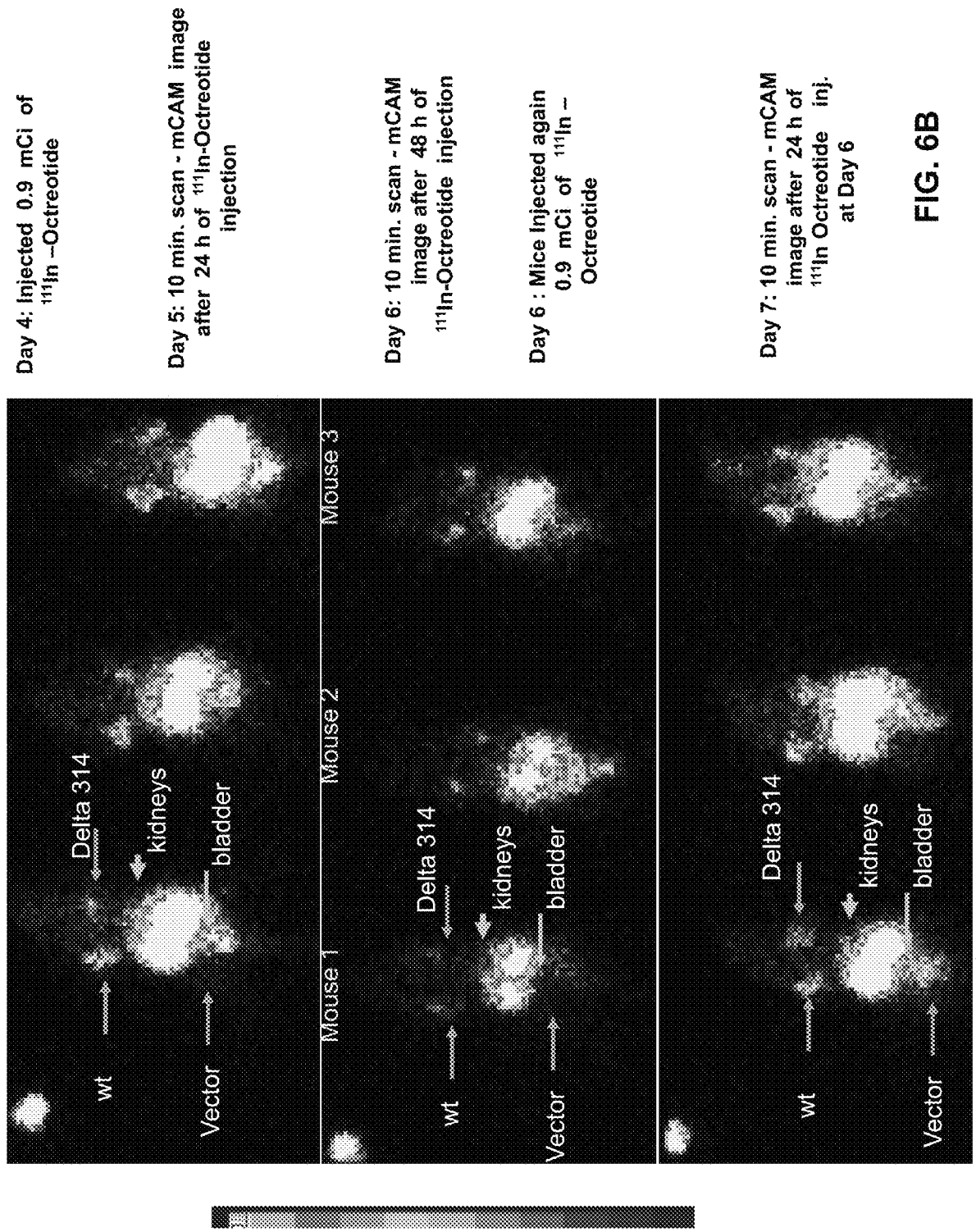

FIG. 6B: Expression of SSTR2 can be imaged in tumors expressing wild-type or signaling deficient HA-SSTR2. Gamma-camera imaging of mice at 24 and 48 hours after the first and 24 hours after the second $^{111}$-In octreotide injection. Uptake (degree of receptor expression) is similar in tumors expressing wild-type or signaling deficient HA-SSTR2 at 24 hours and wanes in both at 48 hours. Increased uptake is again seen 24 hours after the second $^{111}$-In octreotide injection. Minimal uptake is seen in tumors derived from cells transfected with vector. Thus, both wild-type and signaling deficient SSTR2 uptake 111-In octreotide. (Arrows denote the indicated structures.)

Figures 7A, 7B:
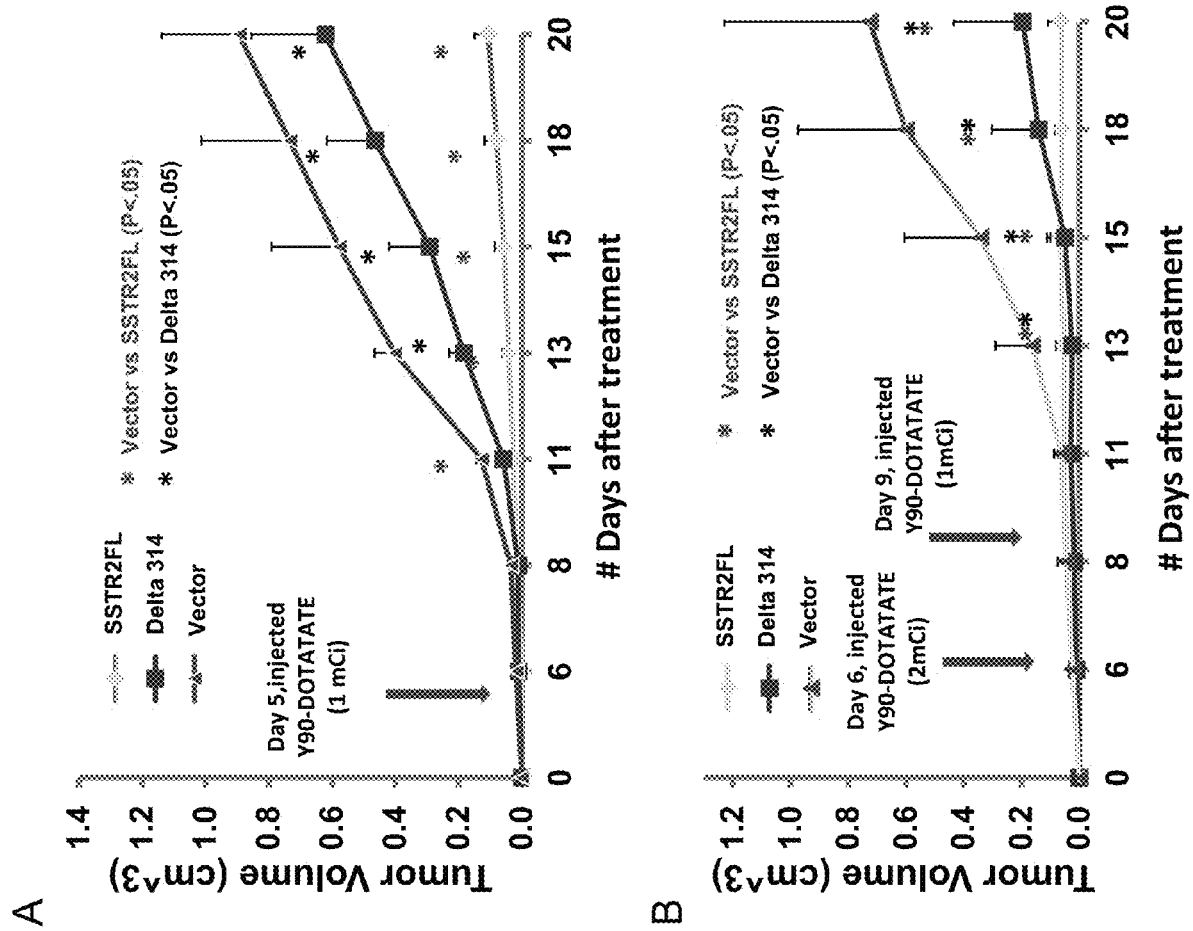

FIGS. 7A-7B: 90Y-octreotate (primarily beta emitter) Inhibited growth of tumors expressing wild-type or signaling deficient receptors, but not tumors derived from vector transfected cells. Stably transfected HT1080 cells were implanted subcutaneously in nude mice (three tumors, HA-wt, HA-D314, vector, per animal). When tumors were palpable, 90Y-octreotate was given once at a dose of 1 mCi (FIG. 7A) or twice at doses of 2 mCi and 1 mCi (FIG. 7B). Tumors were measured by calipers every two days. *$p<0.05$ HA-SSTR2FL or HA-D314 vs Vector. Tumors expressing the signaling deficient receptor decreased in size in a dose dependent manner due to the effect of radioactivity on the tumor. Reduction in size of tumors expressing wild-type HA-SSTR2 was due to a combination of effects of receptor activation by the somatostatin analogue octreotate and effects of radioactivity. This suggests that tumor growth may be inhibited by other mechanisms such as radiation-induced damage in cells without functional SSTR signaling but expressing SSTR's.

Figure 8:
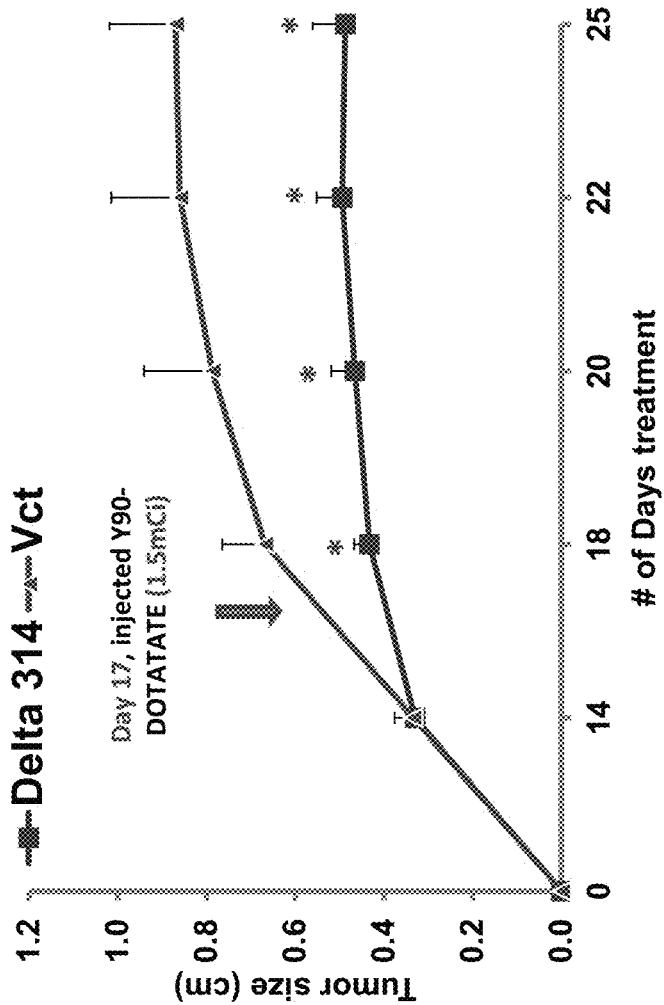

FIG. 8: Stem cells expressing the signaling deficient mutant SSTR2D314 incorporate into tumor and can be targeted with a therapeutic for inhibiting tumor growth. 90Y-octreotate (primarily beta emitter) inhibited growth of human tumors incorporating HS5 human mesenchymal stem cells expressing SSTR2D314, but not control HS5 cells.

Figure 9:
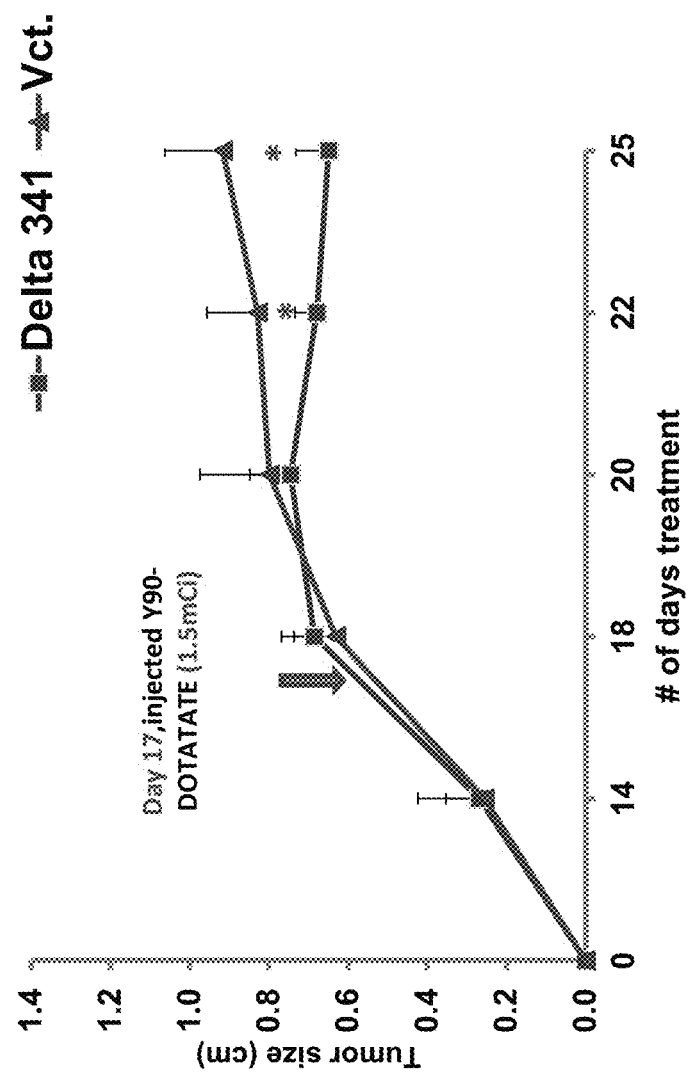

FIG. 9: Stem cells expressing the signaling deficient mutant SSTR2D314 home to and incorporate into tumor and can be targeted with a therapeutic for inhibiting tumor growth. 90Y-octreotate (primarily beta emitter) inhibited growth of human tumors to which human mesenchymal stem cells expressing HA-SSTR2D314 homed and incorporated, but not control HS5 cells.

Figure 10:
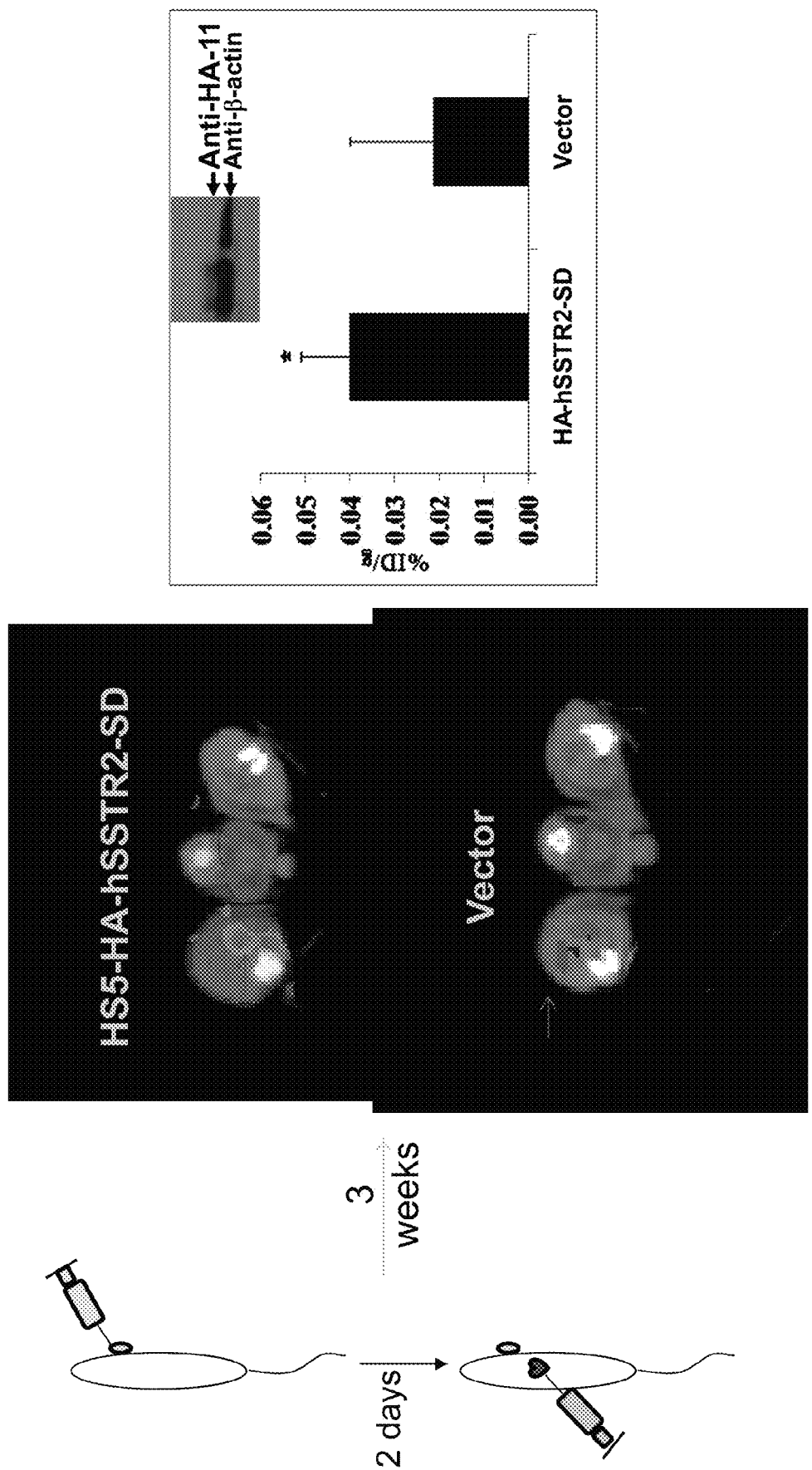

FIG. 10: After intracardiac injection, human MSC's traffic to HeyA8 tumors; and expression of the signaling deficient SSTR2 mutant in such MSC's can be distinguished. (HS5 cells expressing signaling deficient human SSTR2 (HS5-HA-hSSTR2-SD) injected intracardiac localized to Hey A8 tumors in mice and could be visualized one day after 111-In-octreotide injection (arrow, middle panel, top) whereas background signal was seen with control HS5 cells transfected with vector (arrow, middle panel, bottom). After imaging, tumors were removed and evaluated, confirming the imaging findings. Right panel: Biodistribution demonstrated increased uptake of 111-In-octreotide in tumors from animals injected intracardiac with HS5 cells expressing signaling deficient human SSTR2 (HA-hSSTR2-SD) compared to injected with HS5 cells transfected with vector. Inset: Western blot using an antibody to the HA domain of signaling deficient HA-SSTR2 demonstrated expression of the reporter by HS5 cells in tumors from animals injected intracardiac with HS5 cells expressing signaling deficient human SSTR2 (top arrow, left, Anti-HA-11) but not with HS5 cells transfected with vector (top arrow, right, Anti-HA-11). Beta-actin, a control house-keeping protein expected to be found in all tumors, was seen in both tumor lysates (bottom arrow, Anti-beta-actin) as expected.)

Figure 11:
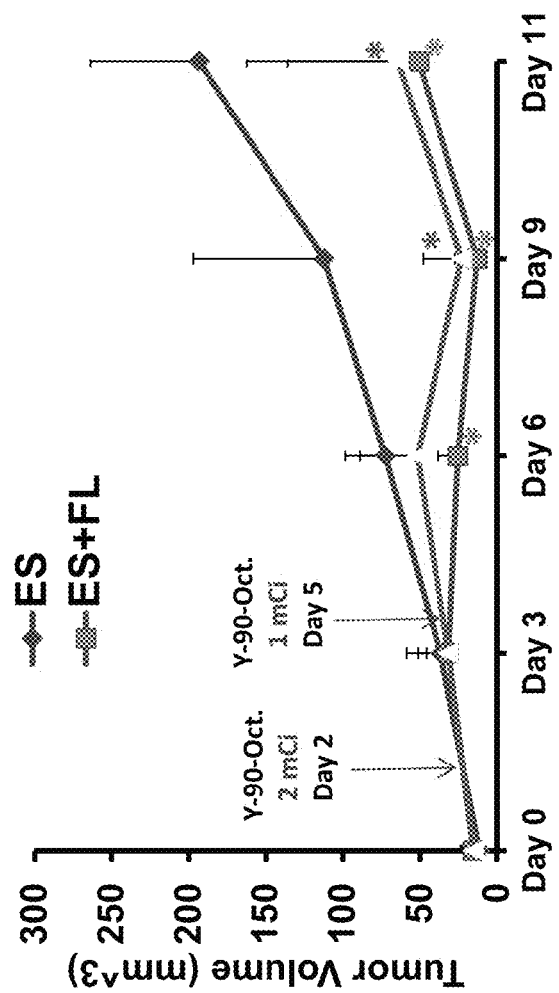

FIG. 11: 90Y-octreotate inhibited growth of embryonic stem cell-derived tumors expressing wild-type or signaling deficient SSTR2-based receptors, but not tumors derived from wild type ES cells. Thus, even if delivered cells go awry, those made to express SSTR2-based genes can be targeted therapeutically. Mouse ES cells (these are pluripotent stem cells that can be used to create transgenic mice and like most ES cells result in teratomas when injected in nude mice) were transfected with a plasmid containing HA-SSTR2 or HA-SSTR2delta314. Clones were then selected for expression. The cells were then injected into nude mice subcutaneously and tumor size was measured by calipers. After tumors were present in three locations per mouse in all 8 mice, the animals were injected i.v. with 90-Y labeled octreotate two days and 5 days later.

Figure 12:
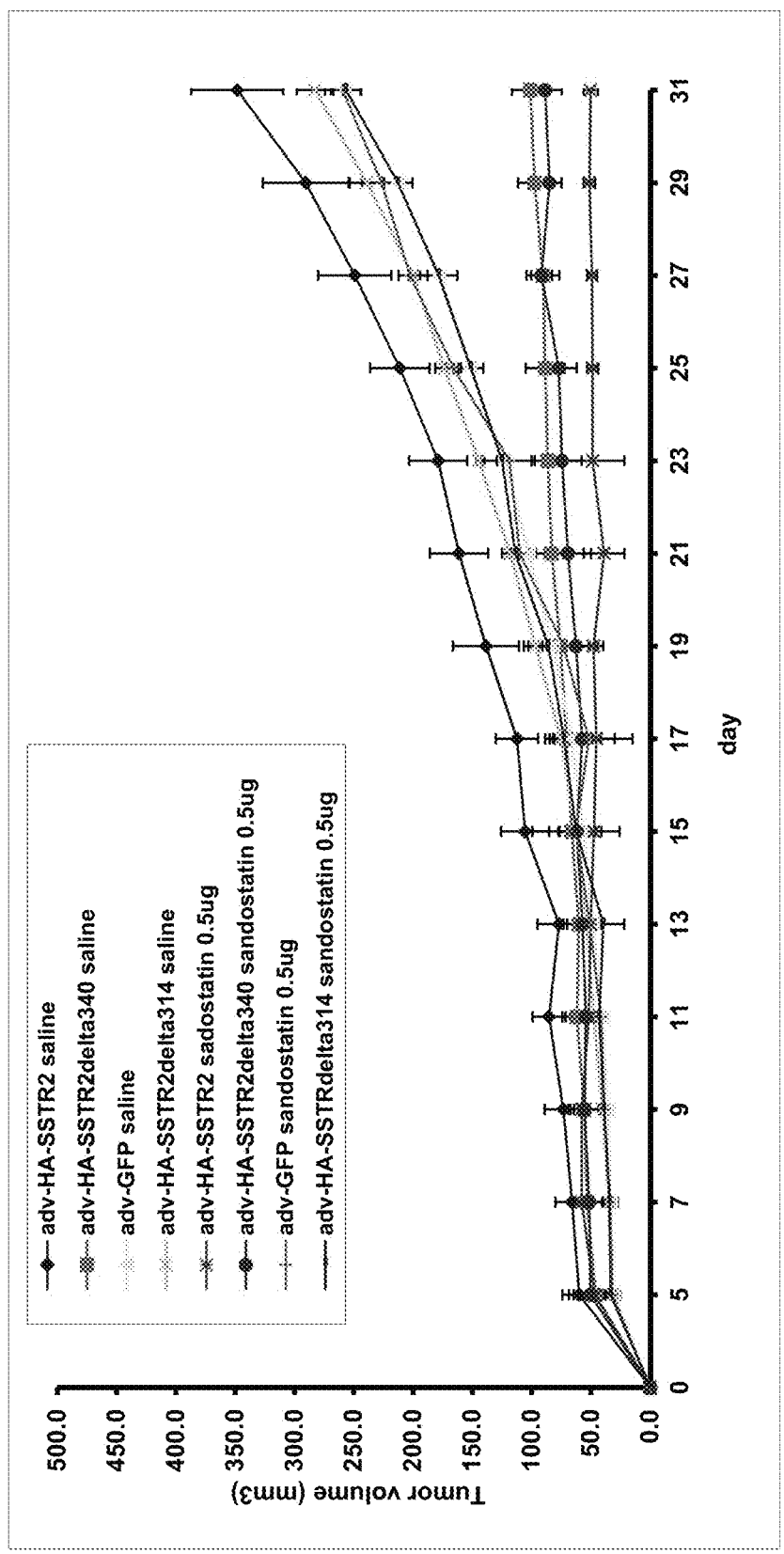

FIG. 12. Constitutively active SSTR2delta340 inhibits the growth of tumor cells. Nude mice were injected subcutaneously with HeyA8 tumors cells and then each tumor was Injected with adenovirus expressing HA-SSTR2delta340 or control inserts (8 tumors per group). Tumor size was measured by calipers. * p<0.05, tumors injected with adv-HA-SSTR2delta340 and given saline vs tumors injected with adv-GFP and given saline; for clarity only the comparison of these two groups is illustrated with *.

DESCRIPTION OF ILLUSTRATIVE EMBODIMENTS

I. Introduction

The invention relates to somatostatin receptors or their mutants that can be used either on their own or with other agents for therapy. Somatostatin receptors are involved in a variety of processes such as cancer (including growth, angiogenesis, invasion, and apoptosis), glucose regulation (such as hyperglycemia of diabetes), neuronal and neuromuscular transmission, gastric acid secretion, growth (such as acromegaly), and ocular neovascularization. In most of these processes, SSTR's have an inhibitory effect that can be therapeutically beneficial.

Signaling altered somatostatin receptors may be used for therapeutic uses that affect or are deficient in affecting functions such as growth inhibition and secretion inhibition. These may act directly, for example, after gene transfer and the expressed constitutively active mutant may have a therapeutic effect such as growth or secretion inhibition. The gene transfer of a signaling altered mutant may serve to localize the expression to the area of interest or systemically.

On the other hand, the signaling defective mutants may act indirectly, for example, through cellular therapy. In this aspect, the signaling defective or deficient mutants are desirable to not to affect the function of the delivered cells, which may home to the area of interest. In particular, maintenance of delivered cell migration and reproduction is important.

With either gene or cellular therapy, the receptor mutants may be used to localize additional therapies, such as therapies that affect cells expressing the SSTR mutant (e.g., a cytotoxic or cytostatic agent to the cell expressing an SSTR mutant), or a therapy that has bystander effect on nearby cells (such as a radioactive substance).

For example, with cellular therapy of tumors, the therapeutic cell could migrate to and then incorporate within the tumor, and via SSTR mutant could localize a substance (for example, a radioligand) that by bystander effect would aid in killing nearby tumor cells.

With gene therapy, adding a radioligand could increase kill of the cells expressing the gene and nearby tumor cells that are either not expressing the mutant or are expressing it at a low level. Gene expression may be heterogeneous even within the same tumor after gene transfer.

The SSTR mutant alone or SSTR mutant binding therapeutic agents may also be used to augment the effect of other therapeutic genes that may, for example, be dual expressed or linked to the SSTR mutants (such as via an internal ribosome entry site (IRES)) to enhance therapeutic efficacy compared to either gene alone.

II. Somatostatin Receptor Mutants

Somatostatin receptor (SSTR), belongs to the family of G protein-coupled receptors with seven transmembrane domains. SSTR2 can serve as a reporter of gene expression that can be quantified in vivo (Yang et al, 2005). Somatostatin receptors are over-expressed on a variety of tumors (John et al, 1996), and somatostatin receptor imaging can identify a variety of neuroendocrine malignancies, including carcinoid, islet cell tumor, pheochromocytoma, paraganglioma, small-cell lung cancer, and medullary thyroid cancer (Termanini et al, 1997; Lamberts et al., 2001; Kwekkeboom et al, 2000). For imaging, radiopharmaceutical analogs of the naturally occurring ligand, somatostatin, may be used. Upon activation, somatostatin initiates a variety of signaling events that affect cellular functions such as secretion, chemotaxis, and growth suppression. These effects have been exploited using therapeutic analogs of somatostatin, for example, to ameliorate or prevent carcinoid syndrome (Nikou et al., 2005; Ducreux et al., 2000; Wymenga et al., 1999).

For somatostatin receptor, in vitro studies suggest that the sixth and seventh transmembrane domains are essential for binding octreotide. Transmembrane domains three through five may also be important because a cysteine-cysteine disulfide bond is predicted between transmembrane domains three and extracellular domain two. Transmembrane domains three through seven have been predicted to cooperate in forming the pocket for binding octreotide.

For signaling, the C-terminus and intracytoplasmic domains of SSTR2 appear to be involved. As stated above, for both rat SSTR2 and human SSTR5, deletion analysis has demonstrated that the cytoplasmic C-terminus regulates inhibition of cAMP production. In particular embodiments of the present invention, the SSTR mutant amino acid sequence is a truncated recombinant somatostatin receptor amino acid sequence. Truncation can be at either the N-terminus or the C-terminus or both termini. For example, deletion of the SSTR2 after amino acid 314 is signaling defective and can be used for targeted therapy and imaging. In other aspects, deletion of the SSTR2 after amino acid 340 is constitutively active and can be used for targeted SSTR-mediated therapy.

There are six somatostatin receptor types, 1, 2A and 2B, 3, 4, and 5. Types 2A and 2B are alternate splice variants that are identical, except that type 2A has a longer intracytoplasmic carboxy-terminus (Petersenn et al., 1999). In certain embodiments, the somatostatin receptor mutant is a mutant of somatostatin receptor type 1, 2, 2A, 2B, 3, 4, or 5. Information pertaining to somatostatin receptors can be found in U.S. Patent Application Pub. No. 2002/0173626, which is herein specifically incorporated by reference in its entirety. Somatostatin receptors may be of any animal species, such as mouse, human, rat, pig, etc. Exemplary information regarding sequences of human or mouse somatostatin receptors is set forth in Table 1:

TABLE 1

Exemplary SSTR Sequence Summary

| SSTR Type | Nucleic Acid Sequence (mRNA or cDNA) | Amino Acid Sequence | Accession No.* for mRNA sequence |
|---|---|---|---|
| 1 (Human) | SEQ ID NO: 1 | SEQ ID NO: 2 | BC035618 |
| 1 (Mouse) | SEQ ID NO: 3 | SEQ ID NO: 4 | NM_009216 |
| 2 (Human) | SEQ ID NO: 5 | SEQ ID NO: 6 | BC019610 |
| 2A (Mouse) | SEQ ID NO: 7 | SEQ ID NO: 8 | NM_001042606 |
| 2B (Mouse) | SEQ ID NO: 9 | SEQ ID NO: 10 | AF008914 |
| 3 (Human) | SEQ ID NO: 11 | SEQ ID NO: 12 | BC096829 |
| 3 (Mouse) | SEQ ID NO: 13 | SEQ ID NO: 14 | BC120843 |
| 4 (Human) | SEQ ID NO: 15 | SEQ ID NO: 16 | BC117270 |
| 4 (Mouse) | SEQ ID NO: 17 | SEQ ID NO: 18 | U26176 |
| 5 (Human) | SEQ ID NO: 19 | SEQ ID NO: 20 | AY081193 |
| 5 (Mouse) | SEQ ID NO: 21 | SEQ ID NO: 22 | AF004740 |

*GenBank Accession Number pertains to nucleic acid sequence and encoded protein.

Detailed information regarding the splice variants of human SSTR2 and its genomic structure can be found in Petersenn et al., 1999, herein specifically incorporated by reference. Additional information regarding the sequence of SSTR2 can be found in Yamada et al. (1992) and Vanetti et al. (1992).

Upon activation, SSTR2 regulates signaling such as cAMP (Schwartkop et al., 1999) and cGMP production. The latter appears to regulate cell proliferation (Lopez et al., 2001). Gambhir et al. (1999) found that a D2 receptor mutant deficient in regulating cAMP can still be imaged. No functional (phenotypic changes) cellular changes were assessed such as effects on proliferation. In COS-7 cells, activation of human SSTR2 results in decreased cAMP production and activation of phospholipase C and calcium mobilization fully or partially, respectively, via a pertussis toxin sensitive G-protein. Through cAMP, somatostatin can regulate secretion. In 32D hematopoietic cells, cAMP appears to be required for SSTR2 mediated chemotaxis. The cytoplasmic C-terminus of the somatostatin receptor is involved in regulating cAMP. Deletion of amino acids beyond 349 of rat SSTR2 increases basal cAMP inhibition in human embryonic kidney (HEK 293) cells. Deletion of amino acids beyond 318 of human SSTR5 eliminates inhibition of cAMP in Chinese hamster ovary (CHO KI) cells.

Inhibition of proliferation by SSTR2 involves multiple downstream mediators including phosphatases. The tyrosine phosphatase SHP-I is regulated by SSTR2, but SHP-I does not appear to regulate cAMP in the breast carcinoma line MCF-7. Upstream of SHP-I are reported to be inhibitory G proteins, the tyrosine phosphatase SHP-2 and the tyrosine kinase Src. SHP-2 interacts with SSTR2 tyrosine 228 in the context LCYLFI in the third intracellular domain and tyrosine 312 in the context of ILYAFL in transmembrane domain 7 next to the C-terminus. The phosphatases may have direct effect on phosphorylation of the somatostatin receptor itself, stimulatory growth factors or other downstream effectors. Phosphatidyl inositol, Ras, Rap1, B-raf, MEK1 and 2, Map kinase/Erk 1 and 2 have been implicated in SSTR2 mediated signaling in CHO DG44 cells; but in neuroblastoma cells, Ras did not appear to be involved and Map kinase/Erk 1 and 2 activity decreased, instead of increased as in CHO DG44 cells.

Also downstream of SHP-I is the neuronal nitric oxide synthase (nNOS) and guanylate cyclase, both of which appear necessary for SSTR2 mediated inhibition of proliferation in CHO cells and mouse pancreatic acinar cells. The inhibition may also involve other phosphotyrosine phosphatases and more downstream effectors such as cyclin dependent kinase inhibitor p27kip1. Somatostatin also regulates transcription factors such as c-jun, c-fos and AP-I.

Among the receptor subtypes, human type 2 (SSTR2; Kluxen et al., 1992; Bell et al. 1993; Panetta et al., 1994; O'Carroll et al., 1993; Yamada et al., 1992) has the highest affinity for the most common clinically used somatostatin imaging analog, [111]Indium-labeled octreotide. This radiopharmaceutical, approved for whole body imaging, and 99mTc labeled analogs, approved for lung imaging, are used in clinical practice to detect tumors over-expressing somatostatin receptors, such as neuroendocrine tumors. This radiopharmaceutical and 99mTc-labeled analogs are used in clinical practice to detect tumors that endogenously over-express somatostatin receptors (John et al., 1996) and have been used in animals models to image tumors that express exogenously introduced SSTR2, for example, as a reporter gene (Kundra et al., 2002).

The normal biodistribution and dosimetry of radiolabeled somatostatin analogs used for imaging clinically has been well studied. The radiopharmaceutical is normally found in the kidneys, bladder, liver, spleen and bowel after intravenous injection. At the tracer doses used for imaging, no side-effects greater than placebo are found and patients are routinely imaged serially. Clinically, increased SSTR2 expression renders even small tumors detectable. PET based agents are also being developed.

The nucleic acid encoding the SSTR amino acid sequence may encode a mutated SSTR sequence, a functional SSTR protein domain, a stably expressed non-functional SSTR, an SSTR polypeptide, or an SSTR polypeptide equivalent, each of which may include one or more transmembrane, extracellular, intracellular, extracellular loop(s) and/or intracellular loop(s). The mutation may be a deletion, point mutation, insertion, truncation, or frame shift mutation. The source of the nucleic acids may be derived from genomic DNA, i.e., cloned directly from the genome of a particular organism, mRNA from a particular organism, and/or synthesized by use of various methods including but not limited to PCR™.

In some embodiments, the nucleic acid may be complementary DNA (cDNA). cDNA is DNA prepared using messenger RNA (mRNA) as a template. Thus, a cDNA does not contain any interrupted coding sequences and usually contains almost exclusively the coding region(s) for the corresponding protein. In other embodiments, the nucleic acid may be produced synthetically.

It may be advantageous to combine portions of the genomic DNA with cDNA or synthetic sequences to generate specific constructs. For example, where an intron is desired in the ultimate construct, a genomic clone may need to be used. Introns may be derived from other genes in addition to SSTR. The cDNA or a synthesized polynucleotide may provide more convenient restriction sites for the remaining portion of the construct and, therefore, would be used for the rest of the sequence.

The present invention also includes nucleic acids encoding mutated SSTR polypeptide equivalents. These nucleic acids encoding SSTR mutant polypeptide equivalents may be naturally-occurring homologous nucleic acid sequences from other organisms. A person of ordinary skill in the art would understand that commonly available experimental techniques can be used to identify or synthesize nucleic acids encoding SSTR mutant polypeptide equivalents. The present invention also encompasses chemically synthesized mutants of these sequences. Another kind of sequence variant results from codon variation. Because there are several codons for most of the 20 normal amino acids, many different DNAs can encode SSTR mutants.

III. Cells for Therapeutic Uses

Cells having the somatostatin receptors or their mutants can be used in various therapeutic applications. In particular embodiments, the cells may be delivered to a tumor or be incorporated into a tumor. An anti-tumor therapeutic or a detectable moiety that target the cells may be administered to the subject. The targeting may be achieved by specific association between a receptor ligand coupled to the therapeutic or the detectable moiety and the introduced receptor mutant in the cells.

The cells that are employed in the methods of the present invention can be any type of cell, such as an eukaryotic cell. In some embodiments, the cells are stem cells, progeny cells thereof, fibroblast cells or immune cells, such as immune progenitor cells or white blood cells.

The cells such as stem cells or immune cells can have transferred an expression construct encoding an SSTR or its mutant prior to introduction of the cells to the subject at any stage in the preparation. In particular embodiments, the mutant may be a truncated SSTR2, such as SSTR2delta314.

The term "stem cell" generally refers to any cells that have the ability to divide for indefinite periods of time and to give rise to specialized cells. The definition of "stem cell" includes, but is not limited to: a) totipotent cells such as an embryonic stem cell, an extraembryonic stem cell, a cloned stem cell, a parthenogenesis derived cell, a cell reprogrammed to possess totipotent properties, or a primordial germ cell; b) a pluripotent cell such as a hematopoietic stem cell, an adipose derived stem cell, a mesenchymal stem cell, a cord blood stem cell, a placentally derived stem cell, an exfoliated tooth derived stem cells, a hair follicle stem cell or a neural stem cell; and c) a tissue specific progenitor cell such as a precursor cell for the neuronal, hepatic, nephrogenic, adipogenic, osteoblastic, osteoclastic, alveolar, cardiac, intestinal, or endothelial lineage.

The cells that are employed in the methods of the present invention can be obtained from any source known to those of ordinary skill in the art. In some embodiments, for example, the cells are stem cells obtained from a donor. In other embodiments, the cells are obtained from the subject who is to receive the cells as part of a therapeutic procedure. The cells can be derived, for example, from tissues such as pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue. In particular embodiments, the cells that are employed in the methods of the present invention are hematopoietic stem cells. The hematopoietic stem cells can be obtained, for example, from the blood or bone marrow of a subject. Further, stem cells of different tissue types (other than hematopoetic stem cells) can be obtained from the blood.

The stem cells to be expanded can be isolated from any organ of any mammalian organism, by any means known to one of skill in the art. The stem cells can be derived from embryonic or adult tissue. One of skill of the art can determine how to isolate the stem cells from the particular organ or tissue of interest, using methods known in the art. In a particular embodiment, the stem cells are isolated from same as prior paragraph. For example, the stem cells can be obtained from blood or bone marrow.

One of skill in the art will be able to determine a suitable growth medium for initial preparation of stem cells. Commonly used growth media for stem cells includes, but is not limited to, Iscove's modified Dulbecco's Media (IMDM) media, DMEM, KO-DMEM, DMEM/F12, RPMI 1640 medium, McCoy's 5 A medium, minimum essential medium alpha medium (.alpha.-MEM), F-12K nutrient mixture medium (Kaighn's modification, F-12K), X-vivo 20, Stemline, CClOO, H2000, Stemspan, MCDB 131 Medium, Basal Media Eagle (BME), Glasgow Minimum Essential Media, Modified Eagle Medium (MEM), Opti-MEM I Reduced Serum Media, Waymouth's MB 752/1 Media, Williams Media E, Medium NCTC-109, neuroplasma medium, BGJb Medium, Brinster's BMOC-3 Medium, CMRL Medium, $CO_2$—Independent Medium, Leibovitz's L-15 Media, and the like.

If desired, other components, such as growth factors, can be added. Exemplary growth factors and other components include, but are not limited to, thrombopoietin (TPO), stem cell factor (SCF), IL-I, IL-3, IL-7, flt-3 ligand (flt-3L), G-CSF, GM-CSF, Epo, FGF-I, FGF-2, FGF-4, FGF-20, IGF, EGF, NGF, LIF, PDGF, bone morphogenic proteins (BMP), activin-A, VEGF, forskolin, glucocorticords, and the like. Furthermore, the media can contain either serum such as fetal calf, horse, or human serum, or more preferably, serum substitution components. Numerous agents have been introduced into media to alleviate the need for serum. For example, serum substitutes have included bovine serum albumin (BSA), insulin, 2-mercaptoethanol and transferrin (TF). One of ordinary skill in the art would be familiar with these supplementary components that can be added to the media.

The stem cells can then be stored for a desired period of time, if needed. Stem cell storage methods are well-known to those of skill in the art.

The stem cells can be sorted prior to administration by methods known in the art, using, for example, antibody technology such as fluorescence activated cell sorting (FACS), magnet activated cell sorting methods (e.g., magnetic resonance beads), column chromatography, or to isolate cells having the desired stem cell markers, or to remove unwanted, contaminating cell types having unwanted cell markers. For example, stem cells expressing an SSTR mutant amino acid sequence can be isolated from cells that do not expression the SSTR mutant amino acid sequence using any of these techniques.

Other cells that could be introduced into a subject for therapy include immune cells. For example, immune cells may be applied in the treatment of cancer. Examples of immune cells include T cells and B cells. For example, using positron emission tomography (PET), Koehne et al (2003) demonstrated in vivo that Epstein-Barr virus (EBV)-specific T cells expressing herpes simplex virus-1 thymidine kinase (HSV-TK) selectively traffic to EBV+ tumors expressing the T cells' restricting HLA allele. Furthermore, these T cells retain their capacity to eliminate targeted tumors. Capitalizing on sequential imaging, Dubey et al. (2003) demonstrated antigen specific localization of T cells expressing HSV-TK to tumors induced by murine sarcoma virus/Moloney murine leukemia virus (M-MS V/M-MuL V).

IV. Therapeutic Agents and Methods

"Treatment" and "treating" refer to administration or application of a drug or therapy (such as protein, nucleic acid, gene therapy, or cell-based therapy) to a subject or performance of a procedure or modality on a subject for the purpose of obtaining a therapeutic benefit of a disease or health-related condition.

The term "therapeutic benefit" used throughout this application refers to anything that promotes or enhances the well-being of the subject with respect to the medical treatment of his condition. This includes, but is not limited to, a reduction in the frequency or severity of the signs or symptoms of a disease.

A "disease" or "health-related condition" can be any pathological condition of a body part, an organ, or a system resulting from any cause, such as infection, genetic defect, trauma, and/or environmental stress. The cause may or may not be known. Examples of such conditions include cancer and diabetes.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

A. Cell-Based Therapy

The cells of the invention may be applied to treat subjects requiring the repair or replacement of body tissues resulting from disease or trauma. Treatment may entail the use of the cells of the invention to produce or induce new tissue, and the use of the tissue thus produced, according to any method presently known in the art or to be developed in the future. For example, the cells of the invention may be given systemically, implanted, injected or otherwise administered directly to the site of tissue damage so that they will produce or induce new tissue in vivo.

In addition, the stem cells, the mature cells produced from these stem cells, and the cell lines derived from these stem cells can be used: (1) to screen for the efficacy and/or cytotoxicity of compounds, allergens, growth/regulatory factors, pharmaceutical compounds, etc.; (2) to elucidate the mechanism of certain diseases; (3) to study the mechanism by which drugs operate; (4) to diagnose, monitor and treat cancer in a patient; (5) for gene therapy; and (6) to produce biologically active products, to name but a few uses.

In addition, immune cells can be applied in methods of therapy. These cells may be active against cells expressing a particular antigen. Methods of therapy involving immune cells involve techniques well-known to those of ordinary skill in the art.

Certain embodiments of the present invention involve introducing a pharmaceutically acceptable dose of cells encoding an SSTR mutant. Pharmaceutical compositions of the present invention comprise a therapeutically or diagnostically effective amount of the cells of the present invention. The phrases "pharmaceutical or pharmacologically acceptable" or "therapeutically effective" or "diagnostically effective" refers to compositions of cells of the present invention that do not produce an unacceptable adverse, allergic or other untoward reaction when administered to a subject, such as, for example, a human or a laboratory animal (e.g., mouse, rat, dog), as appropriate. One of ordinary skill in the art would be familiar with protocols known in the art for the administration of cells (such as stem cells) to a subject for the treatment of a disease. For example, see U.S. Pat. Nos. 5,139,941, 5,670,148, 7,078,032, and 6,927,060, each of which is hereby specifically incorporated by reference.

B. Therapeutic Nuclides

In certain embodiments, therapeutics such as therapeutic nuclides may be used in targeted therapy. The therapeutic nuclides may include radiopharmaceuticals such as alpha-emitting particles, beta-emitting particles, or Auger electrons as described in detail below.

The therapeutic nuclide may be coupled to a carrier that specifically binds to a somatostatin receptor or a mutant thereof. The method may further involve administration of a therapeutic radionuclide into the body by intravenous injection in liquid or aggregate form, ingestion while combined with food, inhalation as a gas or aerosol, or injection of a radionuclide that has undergone micro-encapsulation. Most diagnostic radionuclides emit gamma rays and therefore may be excluded from therapeutic nuclides in certain aspects, while the cell-damaging properties of beta particles are used in therapeutic applications.

Refined radionuclides for use in nuclear medicine may be derived from fission or fusion processes in nuclear reactors, which produce radionuclides with longer half-lives, or cyclotrons, which produce radionuclides with shorter half-lives, or take advantage of natural decay processes in dedicated generators, i.e., molybdenum/technetium or strontium/rubidium, or $^{68}$Ga.

Alpha-Particle Emitters—

Over the past 40 years, the therapeutic potential of several alpha particle-emitting radionuclides has been assessed. These particles (i) are positively charged with a mass and charge equal to that of the helium nucleus, their emission leading to a daughter nucleus that has two fewer protons and two fewer neutrons; (ii) have energies ranging from 5 to 9 MeV and corresponding tissue ranges of approximately five mammalian-cell diameters; and (iii) travel in straight lines. The linear energy transfer (LET, in keV/μm, which reflects energy deposition and, therefore, ionization density along the track of a charged particle) of these energetic and doubly charged (+2) particles is very high (~80-100 keV/μm) along most of their up-to-100-μm path before increasing to ~300 keV/μm toward the end of the track (Bragg peak). Consequently, in the case of cell irradiation, the therapeutic efficacy of alpha-particle emitters depends on (i) distance of the decaying atom from the targeted mammalian cell nucleus—vis-á-vis the probability of a nuclear traversal; and (ii) role of heavy ion recoil of the daughter atom, in particular when the alpha particle emitter is covalently bound to nuclear DNA. Of equal importance are the contribution(s) from bystander effects and the magnitude of cross-dose (from radioactive sources associated with one cell to an adjacent/nearby cell—see below) as this will vary considerably depending on the size of the labeled cell cluster and the fraction of cells labeled.

The application of alpha-particle-emitting radionuclides as targeted therapeutic agents continues to be of interest. When such radionuclides are selectively accumulated in the targeted tissues (e.g., tumors), their decay should result in highly localized energy deposition in the tumor cells and minimal irradiation of surrounding normal host tissues. The investigation of the therapeutic potential of alpha-particle emitters has focused mainly on five radionuclides: astatine-211 (211At), bismuth-212 (212Bi), bismuth-213 (213Bi), radium-223 (223Ra), and actinium-225 (225Ac).

Beta-Particle Emitters—

Beta particles are negatively charged electrons emitted from the nucleus of decaying radioactive atoms (one electron/decay), that have various energies (zero up to a maximum) and, thus, a distribution of ranges. After their emission, the daughter nucleus has one more proton and one less neutron. As these beta particles traverse matter, they lose their kinetic energies and eventually follow a contorted path and come to a stop. Because of their small mass, the recoil energy of the daughter nucleus is negligible. Additionally, the LET of these energetic and negatively (−1) charged particles is very low (~0.2 keV/μm) along their up-to-a-centimeter path (i.e., they are sparsely ionizing), except for the few nanometers at the end of the range. Consequently, their therapeutic efficacy predicates the presence of very high radionuclide concentrations within the targeted tissue. The long range of these emitted electrons leads to the production of cross-fire, a circumstance that negates the need to target every cell within the tumor, so long as all the cells are within the range of the decaying atoms. As with alpha particles, the probability of the emitted beta particle's traversing the targeted cell nucleus depends to a large degree on (i) the position of the decaying atom vis-á-vis the nucleus—specifically nuclear DNA—of the targeted tumor cell; (ii) its distance from the tumor cell nucleus; and (iii) the radius of the latter. Obviously, intranuclear localization of therapeutic radiopharmaceuticals is highly advantageous and, if possible, should always be sought.

Historically, studies of radionuclide-based tumor therapy have been carried out mainly with energetic beta-particle emitters. The exposure of cells in vitro to beta particles leads, in general, to survival curves that have a distinct shoulder and a D0 of several thousand decays. Despite the rather low in vitro cytotoxicity, these radionuclides continue to be pursued for targeted therapy, mainly due to their availability and favorable physical characteristics (e.g., energy and range of the emitted electrons leading to cross-fire irradiation; physical half-lives compatible with the biologic half-lives of the carrier molecules) (Table 2).

TABLE 2

Beta-particle emitters

| Radionuclide | Half-life | $E_{\beta-(max)}$ (keV)$^I$ | $R_{\beta-(max)}$ (mm)$^H$ |
|---|---|---|---|
| $^{33}$P | 25.4 d | 249 | 0.63 |
| $^{177}$Lu | 6.7 d | 497 | 1.8 |
| $^{67}$Cu | 61.9 h | 575 | 2.1 |
| $^{131}$I | 8.0 d | 606 | 2.3 |
| $^{186}$Re | 3.8 d | 1,077 | 4.8 |
| $^{165}$Dy | 2.3 h | 1,285 | 5.9 |
| $^{89}$Sr | 50.5 d | 1491 | 7.0 |
| $^{32}$P | 14.3 d | 1,710 | 8.2 |
| $^{166}$Ho | 28.8 h | 1854 | 9.0 |
| $^{188}$Re | 17.0 h | 2,120 | 10.4 |
| $^{90}$Y | 64.1 h | 2,284 | 11.3 |

Nonenergetic Particles—

During the decay of many radioactive atoms, a vacancy is formed (most commonly in the K shell) as a consequence of electron capture (EC) and/or internal conversion (IC). Each of these vacancies is rapidly filled by an electron dropping in from a higher shell. The process leads to a cascade of atomic electron transitions that move the vacancy toward the outermost shell. These inner-shell electron transitions result in the emission of characteristic X-ray photons or an Auger, Coster-Kronig, or super Coster-Kronig monoenergetic electron (collectively called Auger electrons). Typically, an average of 5 to 30 Auger electrons—with energies ranging from a few eV to approximately 1 keV—are emitted per decaying atom. In addition to producing low-energy electrons, this form of decay leaves the daughter atom with a high positive charge resulting in subsequent charge-transfer processes. The very low energies of Auger electrons have two major consequences: (i) these light, negatively (−1) charged particles travel in contorted paths and their range in water is from a fraction of a nanometer up to ~0.5 μm; and (ii) multiple ionizations (LET: 4-26 keV/μm) occur in the immediate vicinity (few nanometers) of the decay site, reminiscent of those observed along the path of an alpha particle. Finally, the short range of Auger electrons necessitates their close proximity to the radiosensitive target (DNA) for radiotherapeutic effectiveness. This is essentially a consequence of the precipitous drop in energy density as a function of distance in nanometers. Examples of therapeutic Auger-electron emitters include 125I, 123I, 77Br, 111In, and 195mPt.

C. Therapeutic Genes

In certain embodiments of the present invention, the mutant somatostatin receptor-coding sequence or may be operably linked to a therapeutic gene. In further embodiments, a somatostatin receptor ligand may be coupled to a therapeutic gene expression construct to be targeted to somatostatin mutant-expressing cells.

A "therapeutic gene" is a gene which can be administered to a subject for the purpose of treating or preventing a disease. For example, a therapeutic gene can be a gene administered to a subject for treatment or prevention of diabetes or cancer. Examples of therapeutic genes include, but are not limited to, Rb, CFTR, pi 6, p21, p27, p57, p73, C-CAM, APC, CTS-I, zac1, scFV ras, DCC, NF-I, NF-2, WT-I, MEN-I, MEN-II, BRCA1, VHL, MMAC1, FCC, MCC, BRCA2, IL-I, IL-2, IL-3, IL-4, IL-5, IL-6, IL-7, IL-8, IL-9, IL-10, IL-I 1 IL-12, GM-CSF, G-CSF, thymidine kinase, mda7, fus1, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN5 NRAS, PIM1, PML, RET, SRC, TALI, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1 A, cytosine deaminase, Fab, ScFv, BRCA2, zac1, ATM, HIC-I, DPC-4, FHIT, PTEN, ING1, NOEY1, NOEY2, OVCA1, MADR2, 53BP2, IRF-I, Rb, zac1, DBCCR-I, rks-3, COX-I, TFPI, PGS, Dp, E2F, ras, myc, neu, raf, erb. fms, trk, ret, gsp, hst, ab1, E1A, p300, VEGF, FGF, thrombospondin, BAI-I, GDAIF, or MCC.

In certain embodiments of the present invention, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell. Examples of tumor suppressor nucleic acids within this definition include, but are not limited to APC, CYLD, HIN-I, KRAS2b, pló, p19, p21, p27, p27mt, p53, p57, p73, PTEN, Rb, Uteroglobin, Skp2, BRCA-I, BRCA-2, CHK2, CDKN2A, DCC, DPC4, MADR2/JV18, MEN1, MEN2, MTS1, NF1, NF2, VHL, WRN, WT1, CFTR, C-CAM, CTS-I, zac1, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Other exemplary tumor suppressor genes are described in a database of tumor suppressor genes at world wide web at cise.ufl.edu/~yyl/HTML-TSGDB/Homepage.litml. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied in the present invention.

In certain embodiments of the present invention, the therapeutic gene is a gene that induces apoptosis (i.e., a pro-apoptotic gene). A "pro-apoptotic gene amino acid sequence" refers to a polypeptide that, when present in a cell, induces or promotes apoptosis. The present invention contemplates inclusion of any pro-apoptotic gene known to those of ordinary skill in the art. Exemplary pro-apoptotic genes include CD95, caspase-3, Bax, Bag-1, CRADD, TSSC3, bax, hid, Bak, MKP-7, PERP, bad, bcl-2, MST1, bbc3, Sax, BIK, BID, and mda7. One of ordinary skill in the art would be familiar with pro-apoptotic genes, and other such genes not specifically set forth herein that can be applied in the methods and compositions of the present invention. The therapeutic gene can also be a gene encoding a cytokine. The term 'cytokine' is a generic term for proteins released by one cell population which act on another cell as intercellular mediators. A "cytokine" refers to a polypeptide that, when present in a cell, maintains some or all of the function of a cytokine. This definition includes full-length as well as non-full length sequences of any length derived from the full length sequences. It being further understood, as discussed above, that the sequence includes the degenerate codons of the native sequence or sequences which may be introduced to provide codon preference in a specific host cell.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor, prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor, integrin; thrombopoietin (TPO); nerve growth factors such as NGF-β; platelet-growth factor, transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-I, IL-la, IL-2, IL-3, IL-4, IL-5, IL-6, IL-7, IL-8, IL-9, IL-IO IL-I 1, IL-12; IL-13, IL-14, IL-15, IL-16, IL-17, IL-18, IL-19, IL-20, IL-24, LIF, G-CSF5, GM-CSF, M-CSF, EPO, kit-ligand or FLT-3. Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTP ase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidase, a pullanase, a recombinase, a reverse transcriptase, a topoisomerase, a xylanase, a reporter gene, an interleukin, or a cytokine. Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

As will be understood by those in the art, the term "therapeutic gene" includes genomic sequences, cDNA sequences, and smaller engineered gene segments that express, or may be adapted to express, proteins, polypeptides, domains, peptides, fusion proteins, and mutants. The nucleic acid molecule encoding a therapeutic gene may comprise a contiguous nucleic acid sequence of about 5 to about 12000 or more nucleotides, nucleosides, or base pairs. "Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

Encompassed within the definition of "therapeutic gene" is a "biologically functional equivalent" therapeutic gene. Accordingly, sequences that have about 70% to about 99% homology of amino acids that are identical or functionally equivalent to the amino acids of the therapeutic gene will be sequences that are biologically functional equivalents provided the biological activity of the protein is maintained.

V. Detection of Introduced Cells and Genes

In addition to cell-based therapy, methods and compositions for tracking of delivered cells may be also provided. The cells may be delivered to a site of interest by direct injection, targeting moieties, or intrinsic properties of cells themselves, such as the propensity of stem cells to migrate toward a tumor. Tracking of therapeutic cell compositions may help decide the dosage, efficacy, and location of the cells and improve targeting efficiency. The cells may be tracked by detecting the expression of reporters expressed in the delivered cells directly or by further administering a detectable moiety that specifically binds to the reporters.

A. Reporters

In certain embodiments, the introduced SSTR mutant gene may be expressed in the cells and serve as reporters for tracking the cells. In other embodiments of the present invention, the expression construct comprises a coding region that encodes a reporter other than an SSTR mutant. The term "reporter," "reporter gene" or "reporter sequence" as used herein refers to any genetic sequence or encoded polypeptide sequence that is detectable and distinguishable from other genetic sequences or encoded polypeptides present in cells. Preferably, the reporter sequence encodes a protein that is readily detectable either by its presence, its association with a detectable moiety or by its activity that results in the generation of a detectable signal. In particular, reporters that can be imaged non-invasively or with non-invasive techniques are envisioned.

In some embodiments, a reporter nucleic acid may encode a polypeptide having a tag. In association with this embodiment, the method may further comprise the step of contacting the host cell with a fluorescently labeled antibody specific for the tag, thereby labeling the host cell, which may be detected and/or isolated by FACS or other detection, sorting or isolation methods.

In various embodiments, a nucleic acid sequence of certain aspects of the invention comprises a reporter nucleic acid sequence or encodes a product that gives rise to a detectable polypeptide. A reporter is or encodes a reporter molecule which is capable of directly or indirectly generating a detectable signal. Generally, although not necessarily, the reporter gene includes a nucleic acid sequence and/or encodes a detectable polypeptide that is not otherwise produced by the cells. However, non-host species specific (e.g., non-human) reporters expressed in a human subject can incite an immune response that can kill the introduced cells.

Many reporter genes have been described, and some are commercially available for the study of gene regulation (e.g., Alam and Cook, 1990, the disclosure of which is incorporated herein by reference). Signals that may be detected include, but are not limited to color, fluorescence, luminescence, isotopic or radioisotopic signals, cell surface tags, cell viability, relief of a cell nutritional requirement, cell growth and drug resistance. Reporter sequences include, but are not limited to, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, G-protein coupled receptors (GPCRs), CD2, CD4, CD8, the influenza hemagglutinin protein, symporters (such as NIS) and others well known in the art, to which high affinity antibodies or ligands directed thereto exist or can be produced by conventional means, and fusion proteins comprising a membrane bound protein appropriately fused to an antigen tag domain from, among others, hemagglutinin or Myc.

In various embodiments, the desired level of expression of at least one of the reporter sequence is an increase, a decrease, or no change in the level of expression of the reporter sequence as compared to the basal transcription level of the reporter sequence. In a particular embodiment, the desired level of expression of one of the reporter sequences is an increase in the level of expression of the reporter sequence as compared to the basal transcription level of the reporter sequence.

In various embodiments, the reporter sequence encodes unique detectable proteins which can be analyzed independently, simultaneously, or independently and simultaneously. In certain embodiments, the reporter sequence encodes a protein that can be visualized non-invasively such as the SSTR2Δ314.

In other embodiments, the host cell may be a eukaryotic cell or a prokaryotic cell. Exemplary eukaryotic cells include yeast and mammalian cells. Mammalian cells include human cells and various cells displaying a pathologic phenotype, such as cancer cells.

B. Detectable Moieties

In certain embodiments of the invention, a reporter, such as an SSTR mutant amino acid sequence, may be imaged by detecting its association with a detectable moiety. A "detectable moiety" is defined herein to refer to any molecule that can attach, either directly or indirectly, to a reporter. Examples of detectable moieties are set forth above. For example, in some embodiments, the detectable moiety comprises a ligand.

A ligand is defined herein to refer to an ion, a peptide, a oligonucleotide, aptamer, a molecule, a small molecule, or a molecular group that binds to another chemical entity or polypeptide to form a larger complex. In the context of the present invention, the ligand may bind to a reporter or to an amino acid sequence attached to the reporter sequence (e.g., such as a protein tag fused to the N-terminal end or C-terminal end of the reporter amino acid sequence) to form a larger complex. Any ligand known to those of ordinary skill in the art is contemplated for use as a ligand in the context of the present invention. In some embodiments of the present invention, a ligand may be contacted with the cell for imaging. The ligand may or may not be internalized by the cell. Where a reporter has become localized to the cell surface, the ligand, in these embodiments, may bind to or associate with the reporter. Any method of binding of the ligand to the reporter is contemplated by the present invention. In certain other embodiments, a ligand may become internalized by a cell. Once internalized the ligand may, but need not, bind to or associate with the reporter or a second reporter within the cell.

The detectable moiety may be a molecule or part of a molecule that has properties or is conjugated to a moiety such that it is capable of generating a signal that can be detected. Any imaging modality known to those of ordinary skill in the art can be applied to image a ligand. In some embodiments, the ligand is capable of binding to or being coupled to a molecule or part of a molecule that can be imaged. For example, the ligand may be capable of binding to or be coupled to a radionuclide, and the radionuclide can be imaged using nuclear medicine techniques known to those of ordinary skill in the art. For example, the ligand may be $^{111}$In-octreotide. Information regarding imaging using $^{111}$In-octreotide can be found in U.S. Patent App. Pub. No. 20020173626, herein specifically incorporated by reference. In other embodiments, for example, the ligand is capable of binding to or being coupled to a contrast agent that can be detected using imaging techniques well-known to those of ordinary skill in the art. For example, the ligand may be capable of binding to or being coupled to a CT contrast agent, an ultrasound agent, an optical agent, or an MRI contrast agent. In certain embodiments of the present invention, a detectable moiety can bind to the reporter, and the ligand in turn generates a signal that can be measured using an imaging modality known to those of ordinary skill in the art. In other embodiments, the ligand can bind to a protein tag that is fused to the reporter. Thus, for example, imaging would involve measuring a signal from the ligand, and this in turn would provide for localization of the reporter sequence within the cell or within a subject.

A variety of valent metal ions, or radionuclides, are known to be useful for radioimaging and can be employed as detectable moieties. Examples include, but are not limited to $^{67}$Ga, $^{68}$Ga, $^{111}$Tc, $^{111}$In, $^{123}$I, $^{125}$I, $^{131}$I, $^{169}$Yb, $^{60}$Cu, $^{61}$Cu, $^{64}$Cu, $^{62}$Cu, $^{201}$Tl, $^{72}$A, and $^{157}$Gd. In certain embodiments of the present invention, the nucleic acid for use in the imaging methods of the present invention encodes an amino acid sequence that can be radiolabeled in vivo. Radiolabeling of the encoded reporter sequence can be direct, or it can be indirect, such as by radiolabeling of a ligand that can bind the protein tag or reporter sequence. Radiolabeled agents, compounds, and compositions provided by the present invention are provided having a suitable amount of radioactivity.

Once the encoded sequence is radiolabeled, it can be imaged for visualizing a site, such as a tumor in a mammalian body. In accordance with this invention, the radiolabel is administered by any method known to those of ordinary skill in the art. For example, administration may be in a single unit injectable dose, administered as a radiolabeled ligand. Any of the common carriers known to those with skill in the art, such as sterile saline solution or plasma, may be utilized. Generally, a unit dose to be administered has a radioactivity of about 0.01 mCi to about 300 mCi, preferably 5 mCi to about 30 mCi. The solution to be injected at unit dosage is usually from about 0.01 mL to about 10 mL.

After intravenous administration of the radiolabeled reagent, imaging of the organ or tumor in vivo can take place, if desired, in minutes, hours or even longer, after the radiolabeled reagent is introduced into a patient. In some instances, a sufficient amount of the administered dose may accumulate in the area to be imaged within about 0.01, 0.05, 0.1, 0.1, 1, 2, 3, 4, 5, 6, 7, 8, 9, 10 minutes, 0.5, 1, 2, 3, 4, 5, 6, 7, 8, 9, 10 hours or any intermediate ranges.

C. Imaging Methods

Imaging of cells or a detectable moiety may be performed using any method known to those of ordinary skill in the art. Examples include PET, SPECT, and gamma scintigraphy. In gamma scintigraphy, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast). Some aspects of the present invention pertain to methods for tracking the location of a cell in a subject that involve detecting the location of the cell in the subject by contacting the cell with a detectably moiety that binds to the SSTR mutant that is expressed in the cell.

Detection of the expressed SSTR mutant amino acid sequence can be performed by any method known to those of ordinary skill in the art. For example, the reporter may be imaged by administration of a detectable moiety to a subject, wherein the detectable moiety is directed to the reporter amino acid sequence. In other embodiments, the detectable moiety is a radiolabeled probe, such as $^{111}$In-octreotide. In further embodiments, the detectable moiety is a probe that can be imaged optically, such as by fluorescence, near infrared, infrared, MR, or ultrasound. Any method known to those of ordinary skill in the art for measuring a signal derived from a reporter or an associated detectable moiety that attaches to the reporter is contemplated for inclusion in the present invention. Exemplary methods of detecting are as follows.

A variety of nuclear medicine techniques for imaging are known to those of ordinary skill in the art. Any of these techniques can be applied in the context of the imaging methods of the present invention to measure a signal from the reporter. For example, gamma camera imaging is contemplated as a method of imaging that can be utilized for measuring a signal derived from the reporter. One of ordinary skill in the art would be familiar with techniques for application of gamma camera imaging. In one embodiment, measuring a signal can involve use of gamma-camera imaging of an $^{111}$In or $^{99m}$Tc conjugate, in particular $^{111}$In-octreotide or $^{99m}$Tc-somatostatin analogue. Single photon emission tomography (SPECT) may also be performed for three dimensional localization.

Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth. The slices may be combined to build three-dimensional representations.

In CT, intravenous injection of a radiopaque contrast agent can assist in the identification and delineation of soft tissue masses when initial CT scans are not diagnostic. Similarly, contrast agents aid in assessing the vascularity of a soft tissue or bone lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol, and iopanoate. Gadolinium agents have also been reported to be of use as a CT contrast agent (see, e.g., Henson et al, 2004). For example, gadopentate agents have been used as a CT contrast agent (discussed in Strunk and Schild, 2004).

Magnetic resonance imaging (MRI) is an imaging modality that uses a high-strength magnet and radio-frequency signals to produce images. The most abundant molecular species in biological tissues is water. It is the quantum mechanical "spin" of the water proton nuclei that ultimately gives rise to the signal in imaging experiments and other nuclei can also be imaged. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT, SPECT, and PET image, is normally displayed in two-dimensional slices. The slices may be combined to build three-dimensional representations. Contrast agents used in MR or MR spectroscopy imaging differ from those used in other imaging techniques. Their purpose is to aid in distinguishing between tissue components with similar signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles. Atoms other than H, may be used, such as F and Na. Contrast may also be introduced using hyperpolarization.

PET and SPECT Imaging modalities that provide information pertaining to information at the cellular level, such as cellular viability, include positron emission tomography (PET) and single-photon emission computed tomography (SPECT). In PET, a patient ingests or is injected with a radioactive substance that emits positrons, which can be monitored as the substance moves through the body. Closely related to PET is single-photon emission computed tomography, or SPECT.

The major difference between the two is that instead of a positron-emitting substance, SPECT uses a radioactive tracer that emits high-energy photons. SPECT is valuable for diagnosing multiple illnesses including coronary artery disease, and already some 2.5 million SPECT heart studies are done in the United States each year. PET radiopharmaceuticals for imaging are commonly labeled with positron-emitters such as $^{11}$C, $^{13}$N, $^{15}$O, $^{18}$F, $^{82}$Rb, $^{62}$Cu, and or $^{68}$Ga. SPECT radiopharmaceuticals are commonly labeled with positron emitters such as $^{99m}$Tc, $^{201}$Tl, and $^{67}$Ga, or $^{111}$In. Important receptor-binding SPECT radiopharmaceuticals include [$^{123}$I]QNE, [$^{123}$I]IBZM, and [$^{123}$I]iomazenil. These tracers bind to specific receptors, and are of importance in the evaluation of receptor-related diseases Optical imaging is another imaging modality that has gained widespread acceptance in particular areas of medicine. Examples include optical labeling of cellular components, and angiography such as fluorescein angiography and indocyanine green angiography of the eyes. Examples of optical imaging agents include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye. Optical imaging includes near infrared imaging and infrared imaging. Near infrared imaging has more tissue penetration and less background.

Another biomedical imaging modality that has gained widespread acceptance is ultrasound. Ultrasound imaging has been used to provide real-time cross-sectional and even three-dimensional images of soft tissue structures and blood flow information in the body. High-frequency sound waves and a computer create images of blood vessels, tissues, and organs.

Ultrasound imaging of blood flow can be limited by a number of factors such as size and depth of the blood vessel. Ultrasonic contrast agents, a relatively recent development, include perfluorine and perfluorine analogs, which are designed to overcome these limitations by helping to enhance grey-scale images and Doppler signals.

Photoacoustic and thermoacoustic imaging may also be used in certain aspects. Photoacoustic imaging delivers non-ionizing laser pulses. Some of these are absorbed and converted to heat leading to thermoelastic expansion and ultrasonic emission that is detected by an ultrasound transducer. Photoacoustic imaging may be used on native tissue, or with contrast agents. When radio frequency, instead of light, is used to heat tissue, it is referred to as thermoacoustic imaging.

In certain embodiments, imaging using more than one modality is performed. For example, as set forth above, the imaging modality may include, but are not limited to, CT, MRI, PET, SPECT, ultrasound, or optical imaging. Other examples of imaging modalities known to those of ordinary skill in the art are contemplated by the present invention.

The imaging modalities may be performed at any time during or after administration of the composition comprising the diagnostically effective amount of the compound that comprises two imaging moieties. For example, the imaging studies may be performed during administration of the dual imaging compound of the present invention, or at any time thereafter. In some embodiments, the first imaging modality is performed beginning concurrently with the administration of the dual imaging agent, or about 1 sec, 1 hour, 1 day, or any longer period of time following administration of the dual imaging agent, or at any time in between any of these stated times. In some embodiments of the present invention a second imaging modality may be performed concurrently with the first imaging modality, or at any time following the first imaging modality. For example, the second imaging modality may be performed about 1 sec, about 1 hour, about 1 day, or any longer period of time following completion of the first imaging modality, or at any time in between any of these stated times. One of ordinary skill in the art would be familiar with performance of the various imaging modalities contemplated by the present invention.

D. Imaging of a Subject Following Stem Cell Administration

Imaging of a cell and/or its progeny can be performed following introduction of a cell into a subject. For example, imaging can be performed after about 1 second, 1 minute, 1 hour, 1 day, 1 week, 1 month, 1 year, or any longer period of time following administration of the cell. In some embodiments, imaging and biodistribution analysis can be performed as described by Yang et al, 2005. In other embodiments, imaging may be preformed after approximately one and one-half weeks. One of ordinary skill in the art would be familiar with generating a protocol to imaging cells, such as stem cells, following introduction of cells into a subject.

Imaging of a cell and/or its progeny that include an expressed SSTR mutant can be performed for several purposes. For example, imaging can be performed to follow the transit of cells, such as stem cells, in the body following introduction of the cells into a subject. Imaging can also be used to assess cell viability following introduction of the cells into a subject, and over the course of time. Further, imaging can also be performed to assess stem cell or immune cell localization in a subject. For example, placing the reporter under the control of a constitutive promoter would provide for constant expression that may be used to assess localization and viability of the cell. Imaging can be used to assess trans/differentiation or fusion. For example, placing the reporter under the control of a tissue-selective promoter sequence would provide for expression of a particular reporter only upon trans/differentiation or fusion of a cell or its progeny to a particular tissue/cell type.

Alternatively, imaging can be performed to assess an immune cell, stem cell or its progeny's expression from a promoter of a gene whose product performs a function of interest following introduction of the cell into a subject. For example, placing a reporter in the expression construct under the control of a function-specific promoter would provide for expression of the reporter in stem cells until trans/differentiation or fusion. Alternatively expression may occur upon differentiation of the cell into a cell capable of performing a specific function. As an example in lymphocytes, T-cell activation may be assessed using promoter elements that initiate transcription upon T-cell activation. Thus, imaging can be applied in a wide variety of contexts that are significant in the context of cell therapy such as stem cell and immune cell therapy.

The reporter may be linked to a gene of interest, for example by an IRES or a bidirectional promoter, so that expression of the reporter may be used to track not only its own expression, but also that of the gene of interest. Examples of genes of interest include those whose products may function in homing, implantation or differentiation.

With multiple promoter-reporter constructs transferred into a cell, combinations of the above may be evaluated including in vivo. For example, with multiple promoter-reporter constructs transferred individually or together, viability, localization, differentiation, functional expression, and indirect evaluation of expression of a linked gene of interest may be evaluated. When used in combination, different promoters and different reporters that can be identified either simultaneously or serially may need to be employed. Simultaneous evaluation may be performed for example if the reporter or its detectable moiety have separable characteristics, for example, different energies of emission of gamma rays that can be separated by a gamma camera. In certain embodiments, a combination of more than one imaging technique can be used to determine trafficking, viability, and/or differentiation of the cells. For example, MR and γ-camera imaging can be used to determine the biodistribution of radiopharmaceutical in tumors. Imaging can be performed following administration of a subject with a detectable moiety. Because the detectable moiety will have a limited physical and biological life, imaging of the reporter can be performed repeatedly. In addition, cells that have been exposed to a detectable moiety can be introduced into the subject, and then the subject subjected to one or more imaging techniques following introduction of the cells. Imaging can be performed a single time or more than one time point following introduction of the cells into the subject allowing serial evaluation. Image acquisition can be performed by any method known to those of ordinary skill in the art.

The reporter within the cells can be detected both in vivo and ex vivo. In certain embodiments, ex vivo evaluation occurs on a biopsy sample of tissue obtained from the subject following introduction of the cell into the subject. Ex vivo evaluation for the reporter can be performed using a variety of techniques including but not limited to autoradiography, immunologic techniques such as immunohistochemistry, ELISA or Western blotting, PCR™, optical, CT, MR, nuclear imaging, or ultrasound. As discussed above, in vivo-imaging can also be performed using any of a variety of modalities known to those of ordinary skill in the art.

VI. Pharmaceutical Preparations and Compositions

Pharmaceutical compositions of the present invention comprise an effective amount of one or more cell or gene delivery compositions or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference).

The cells of the present invention can be introduced to a subject by any method known to those of ordinary skill in the art. Examples include intravenously, intradermally, intraarterially, intraperitoneally, intralesionally, intracranially, intraarticular ly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, directly into a heart chamber, directly injected into the organ or portion of organ or diseased site of interest, or by other method or any combination of the forgoing as would be known to one of ordinary skill in the art.

The actual required amount of a composition of the present invention administered to a subject, such as a patient with a disease, can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The present invention contemplates methods of preventing, inhibiting, or treating such diseases or conditions in a subject by administration of a cell that has been transfected with an expression construct comprising a sequence encoding a somatostatin receptor constitutively active mutant. Aspects of the invention also include the use of the methods and compositions of the invention in combination with other therapies, as discussed in greater detail below.

Diseases to be prevented, treated or diagnosed can be any disease that affects a subject that would be amenable to therapy or prevention through administration of a cell as described herein. For example, the disease may be a disease amenable to stem cell therapy. Examples include cancer, diabetes, cardiovascular disease, neurological disease, neurodegenerative disease, genetic disease, liver disease, infection, trauma, toxicity, or immunological disease. Additional diseases are discussed elsewhere in this specification.

For example, the disease may be a hyperproliferative disease. A hyperproliferative disease is a disease associated with the abnormal growth or multiplication of cells. The hyperproliferative disease may be a disease that manifests as lesions in a subject. Exemplary hyperproliferative lesions include pre-malignant lesions, cancer, and tumors. The cancer can be any type of cancer including those derived from mesoderm, endoderm, or ectoderm such as blood, heart, lung, esophagus, muscle, intestine, breast, prostate, stomach, bladder, liver, spleen, pancreas, kidney, neurons, myocytes, leukocytes, immortalized cells, neoplastic cells, tumor cells, cancer cells, duodenum, jejunum, ileum, cecum, colon, rectum, salivary glands, gall bladder, urinary bladder, trachea, larynx, pharynx, aorta, arteries, capillaries, veins, thymus, lymph nodes, bone marrow, pituitary gland, thyroid gland, parathyroid glands, adrenal glands, brain, cerebrum, cerebellum, medulla, pons, spinal cord, nerves, skeletal muscle, smooth muscle, bone, testes, epidiymides, prostate, seminal vesicles, penis, ovaries, uterus, mammary glands, vagina, skin, eyes, or optic nerve.

Other examples of diseases to be treated include return of lost or lack of function such as diabetes where insulin production is inadequate, infectious diseases, genetic diseases, and inflammatory diseases, such as autoimmune diseases. The methods and compositions of the present invention can be applied to deliver an antigen that can be applied in immune therapy or immune prophylaxis of a disease. One of ordinary skill in the art would be familiar with the many disease entities that would be amenable to prevention or treatment using the pharmaceutical compositions and methods set forth herein.

VII. Combination Therapy

It is an aspect of this invention that the claimed methods for treating cells in a subject can be used in combination with another agent or therapy method.

In certain embodiments, the disease is cancer, the other agent or therapy is another anti-cancer agent or anti-cancer therapy. Treatment with the claimed somatostatin receptor-based therapeutic agent may precede or follow the other therapy method by intervals ranging from minutes to weeks. In embodiments where another agent is administered, one would generally ensure that a significant period of time did not expire between the time of each delivery, such that the agents would still be able to exert an advantageously combined effect on the cell. For example, it is contemplated that one may administer two, three, four or more doses of one agent substantially simultaneously (i.e., within less than about a minute) with the therapeutic agents of the present invention. In other aspects, a therapeutic agent or method may be administered within about 1 minute to about 48 hours or more prior to and/or after administering an SSTR-based therapeutic agent or agents of the present invention, or prior to and/or after any amount of time not set forth herein. In certain other embodiments, an SSTR-based therapeutic agent of the present invention may be administered within of from about 1 day to about 21 days prior to and/or after administering another therapeutic modality, such as surgery or gene therapy. In some situations, it may be desirable to extend the time period for treatment significantly, however, where several weeks (e.g., about 1 to 8 weeks or more) lapse between the respective administrations. Various combinations may be employed, the claimed SSTR-based agent is derivative is "A" and the secondary agent, which can be any other therapeutic agent or method, is "B":

A/B/A B/A/B B/B/A AJAJB A/B/B BIAJA A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the SSTR-based therapeutic agents of the present invention to a patient will follow general protocols for the administration of chemotherapeutics, taking into account the toxicity, if any, of these agents. It is expected that the treatment cycles would be repeated as necessary. It also is contemplated that various standard therapies, as well as surgical intervention, may be applied in combination with the therapeutic. These therapies include but are not limited to additional drug therapy, chemotherapy, additional radiotherapy, immunotherapy, gene therapy and surgery.

A. Chemotherapy

Cancer therapies also include a variety of combination therapies with both chemical and radiation based treatments. Chemotherapies include, but are not limited to, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemo therapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune modulators, immune effector cells and molecules to cure or palliate disease. In certain embodiments, immune modulators, immune effector cells and molecules target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells.

Many tumor markers exist and any of these may be suitable for targeting in the context of the present invention. Common tumor markers include carcino embryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and pi 55.

D. Nucleic Acid-Based Therapy

In yet another embodiment, the secondary treatment is an additional gene therapy in which a therapeutic polynucleotide is administered before, after, or at the same time as the nucleic acid composition of the present invention. Delivery of the SSTR-based therapeutic agent in conjunction with a vector encoding a gene product will have a combined therapeutic effect such as an anti-hyperproliferative effect on target tissues.

RNA interference (RNAi) is a powerful gene-silencing process that holds great promise in the field of cancer therapy. The evolving understanding of the molecular pathways important for carcinogenesis has created opportunities for cancer therapy employing RNAi technology to target the key molecules within these pathways. Major targets for siRNA therapy include oncogenes and genes that are involved in angiogenesis, metastasis, survival, antiapoptosis and resistance to chemotherapy.

Many gene products involved in carcinogenesis have already been explored as targets for RNAi intervention, and RNAi targeting of molecules crucial for tumor-host interactions and tumor resistance to chemo- or radiotherapy has also been investigated. In most of these studies, the silencing of critical gene products by RNAi technology has generated significant antiproliferative and/or proapoptotic effects in cell-culture systems or in preclinical animal models.

siRNA can be introduced into the cells by using either chemically synthesized siRNA oligonucleotides (oligos), or vector-based siRNA (shRNA), which allows long lasting and more stable gene silencing. Nanoparticles and liposomes are commonly used carriers, delivering the siRNA with better transfection efficiency and protecting it from degradation. In combination with standard chemotherapy, siRNA therapy can also reduce the chemoresistance of certain cancers, demonstrating the potential of siRNA therapy for treating many malignant diseases.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

VIII. Nucleic Acids

Aspects of the invention include introducing into a cell with an expression construct comprising at least a first region that is a nucleic acid sequence encoding a somatostatin receptor or its mutant operatively linked to a first promoter sequence. The somatostatin mutant may be constitutively active or signaling defective. In other aspects, expression construct may include one or more additional nucleic acid sequences, such as additional reporters, additional coding regions, or additional promoters The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring or derivatized purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule The term "vector" is used to refer to a carrier into which a nucleic acid sequence can be inserted for introduction into a cell where it can be expressed and/or replicated. The term "expression vector," "expression construct" or "nucleic acid vector" refers to a nucleic acid containing a nucleic acid sequence or "cassette" coding for at least part of a nucleic acid sequence, also referred to herein as a gene, product capable of being transcribed and "regulatory" or "control" sequences, which refer to nucleic acid sequences necessary for the transcription and possibly translation of an operably linked coding sequence in a particular host cell. In addition to control sequences that govern transcription and translation, the expression vectors may contain nucleic acid sequences that serve other functions as well.

The term "promoter" is used interchangeably with "promoter element" and "promoter sequence." Likewise, the term "enhancer" is used interchangeably with "enhancer element" and "enhancer sequence." A promoter, enhancer, or repressor, is said to be "operably linked" to a nucleic acid or transgene, such as a nucleic acid encoding a recombinant seven transmembrane G-protein associated receptor, when such element(s) control(s) or affect(s) nucleic acid or transgene transcription rate or efficiency. For example, a promoter sequence located proximally to the 5' end of a transgene coding sequence is usually operably linked with the transgene. As used herein, term "regulatory elements" is used interchangeably with "regulatory sequences" and refers to promoters, enhancers, polyadenylation sites and other expression control elements, or any combination of such elements.

A. Promoters

Promoters are positioned 5' (upstream) to the genes that they control. Many eukaryotic promoters contain two types of recognition sequences: TATA box and the upstream promoter elements. The TATA box, located 25-30 bp upstream of the transcription initiation site, is thought to be involved in directing RNA polymerase II to begin RNA synthesis at the correct site. In contrast, the upstream promoter elements determine the rate at which transcription is initiated. These elements can act regardless of their orientation, but they must be located within 100 to 200 bp upstream of the TATA box.

Enhancer elements can stimulate transcription up to 1000-fold from linked homologous or heterologous promoters. Enhancer elements often remain active even if their orientation is reversed (Li et al, 1990). Furthermore, unlike promoter elements, enhancers can be active when placed downstream from the transcription initiation site, e.g., within an intron, or even at a considerable distance from the promoter (Yutzey et al, 1989).

As is known in the art, some variation in this distance can be accommodated without loss of promoter function. Similarly, the positioning of regulatory elements with respect to the transgene may vary significantly without loss of function. Multiple copies of regulatory elements can act in concert. Typically, an expression vector comprises one or more enhancer sequences followed by, in the 5' to 3' direction, a promoter sequence, all operably linked to a transgene followed by a polyadenylation sequence. A "promoter" sequence is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence. Together, an appropriate promoter or promoter/enhancer combination, and a gene of interest, comprise an expression cassette. One or more expression cassettes may be present in a given nucleic acid vector or expression vector. In certain aspects, one expression cassette may encode a transactivator that interacts with a promoter of a second expression cassette. The one or more expression cassettes may be present on the same and/or different expression vector.

A promoter may be one naturally associated with a gene or sequence, as may be obtained by isolating a portion the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the nucleic acid segment under the control of a recombinant or heterologous promoter, which refers to a promoter that is not normally associated with a nucleic acid sequence in its natural environment.

In certain aspect of the invention a heterologous promoter may be a chimeric promoter, where elements of two or more endogenous, heterologous or synthetic promoter sequences are operatively coupled to produce a recombinant promoter. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Such promoters may be used to drive reporter expression, which include, but are not limited to GPCRs, f-galactosidase or luciferase to name a few. Furthermore, it is contemplated the control sequences that direct transcription and/or expression of sequences within non-nuclear organelles such as mitochondria, chloroplasts, and the like, can be employed as well.

A promoter and/or enhancer could be used that effectively directs the expression of the DNA segment in a cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-selective, inducible, lineage-specific, or function-specific and/or useful under the appropriate conditions to direct expression of the introduced DNA segment, such as is advantageous in the production of proteins, recombinant proteins and/or peptides. The promoter may be heterologous or endogenous or a combination thereof. The position of the promoter/may be varied. It is contemplated that 1, 2, 3, 4, or more expression cassettes may be present in a particular vector or a particular cell with no general preference as to the order of the cassettes in an expression vector. A first, second, third or fourth promoter of an expression cassette may be a constitutive, tissue selective, lineage specific, or function-specific promoter sequence that drives expression of a gene of interest, such as a protein tag gene, a reporter, a signaling sequence, a trafficking sequence, or a therapeutic gene.

Certain aspects of the invention include promoter sequences that interact with endogenous or exogenous transactivators. In certain aspects a transactivator is a recombinant transactivator. A recombinant transactivator may be expressed in cells into which a nucleic acid of the invention is introduced. Alternatively, a recombinant transactivator or a nucleic acid encoding a recombinant transactivator may be introduced before, with or after a nucleic acid of the invention. In certain aspects, the recombinant transactivator may be encoded in a nucleic acid encoding an imaging or therapeutic agent.

A promoter may be functional in a variety of tissue types and in several different species of organisms, or its function may be restricted to a particular species and/or a particular normal or diseased tissue or cell type. Further, a promoter may be constitutively active, or it may be selectively activated by certain substances (e.g., a tissue-selective factor), under certain conditions (e.g., hypoxia, or the presence of an enhancer element in the expression cassette containing the promoter), or during certain developmental stages of the organism (e.g., active in fetus, silent in adult). A "function-specific promoter sequence" is a control sequence that is a region of a nucleic acid sequence at which initiation and rate of transcription are controlled, wherein the sequence is active in cells and whose products perform a particular function of interest. Examples include insulin, T-cell receptor, immunoglobulin, hormone or paracrine promoters such as vascular endothelial growth factor, structural protein promoters such as dystrophin, intracellular components such as fat or melanin, or extracellular components such as cartilage.

Promoters useful in the practice of the present invention may be tissue-specific—that is, they are capable of driving transcription of a gene in one or a few normal or diseased tissue(s) while remaining largely "silent" or expressed at relatively low levels in other tissue types. It will be understood, however, that tissue-specific or tissue-selective promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the present invention typically has a selectivity ratio of greater than about 1:1.01, 1:1.1, 1:1.5, 1:2, 1:3, 1:4, 1:5 or more. Preferably, the selectivity ratio is greater than about 1:1.5. The promoter may also function in a reverse manner with decreased activity in the normal or diseased tissue(s) of interest. It will be further understood that certain promoters, while not restricted in activity to a single tissue type, may nevertheless show selectivity in that they may be active in one group of tissues, and less active or silent in another group. Such promoters are also termed "tissue specific" or "tissue selective," and are contemplated for use with the present invention. For example, promoters that are active in a particular type of tissue may be therapeutically useful in diseases affecting the tissue that may be amenable to stem cell therapy.

The level of expression of a coding region under the control of a particular promoter can be modulated by manipulating the promoter region. For example, different domains within a promoter region may possess different gene-regulatory activities. The roles of these different regions are typically assessed using vector constructs having different variants of the promoter with specific regions deleted (i.e., deletion analysis) or base pair(s) mutated. Vectors used for such experiments typically contain a reporter sequence, which is used to determine the activity of each promoter variant under different conditions. Application of such a deletion analysis enables the identification of promoter sequences containing desirable activities and thus identifying a particular promoter domain, including core promoter elements, those elements when deleted detrimentally effect characteristics of the promoter, such as but not limited to selectivity or transcription factor binding. This approach may be used to identify, for example, the smallest region capable of conferring tissue specificity, or the smallest region conferring a robust transcriptional response when combined with other promoter elements, such as but not limited to the core CMV promoter or a mini-CMV.

A number of promoters, described herein, may be particularly advantageous in practicing the present invention. In most instances, these promoters may be isolated as convenient restriction digest fragments suitable for cloning into a selected vector. Alternatively, promoter fragments may be isolated using the polymerase chain reaction or by oligonucleotide synthesis. Cloning of these promoter fragments may be facilitated by incorporating restriction sites at the 5' ends of the primers.

The promoter sequence can be any promoter sequence known to those of ordinary skill in the art. Promoter sequences are discussed in detail elsewhere in this specification. For example, the promoter sequence may be a function-specific promoter sequence, a constitutive promoter sequence, or a tissue-selective promoter sequence.

In particular embodiments, the promoter sequence is a function-specific promoter sequence. A "function specific promoter sequence" is a control sequence that is a region of a nucleic acid sequence at which initiation and rate of transcription are controlled, wherein the sequence is active in cells and whose products perform a particular function of interest. Examples of tissue selective promoter sequences include an insulin promoter sequence, T cell receptor promoter sequence, immunoglobulin promoter sequence, hormone or paracrine promoters such as vascular endothelial growth factor promoter sequences, structural protein promoters such as a dystrophin promoter sequence, intracellular component such as fat or melanin promoter sequences, or extracellular component such as cartilage promoter sequences. Other examples include a pBROAD promoter sequence, a c-fos promoter sequence, a c-HA-ras promoter sequence, an intercellular adhesion molecule 2 promoter sequence, and a platelet-derived growth factor (PDGF) promoter sequence.

The promoter sequence may also be a constitutive promoter sequence. A "constitutive promoter sequence" is defined herein to refer to a control sequence that is a region of a nucleic acid sequence at which initiation and rate of transcription are controlled, wherein the sequence is active in cells of most any lineage. For example, the constitutive promoter sequence may be a beta-actin promoter sequence, an elastase I promoter sequence, a metallothionein (MTII) promoter sequence, a 5 S ribosomal promoter sequence, an Elastase promoter sequence, an Elastase I promoter sequence, a polyoma promoter sequence, a Cytomegalovirus promoter sequence, a retrovirus promoter sequence, a papilloma virus promoter sequence, a fibronectin promoter sequence, a ubiquitin promoter, an actin promoter, an elongation factor 1 alpha, an early growth factor response 1, an eukaryotic initiation factor 4A1, a ferritin heavy chain, a ferritin light chain, a glyceraldehyde 3-phosphate dehydrogenase, a glucose-regulated protein 78, a glucose-regulated protein 94, a heat shock protein 70, a heat shock protein 90, a beta-kinesin, a phosphoglycerate kinase, an ubiquitin B, a beta-actin, RNA virus promoter, DNA virus promoter, adenoviral promoter sequence, a baculoviral promoter sequence, a CMV promoter sequence, a parvovirus promoter sequence, a herpesvirus promoter sequence, a poxvirus promoter sequence, an adeno-associated virus promoter sequence, a semiliki forest virus promoter sequence, an SV40 promoter sequence, a vaccinia virus promoter sequence, a lentivirus promoter, a retrovirus promoter sequence, or a minimal viral promoter sequence. One of ordinary skill in the art would be familiar with these and other constitutive promoter sequences.

In some embodiments, the constitutive promoter is a minimal viral promoter sequence. For example, the minimal viral promoter sequence may be a RNA virus promoter, DNA virus promoter, adenoviral promoter sequence, a baculoviral promoter sequence, a CMV promoter sequence, a parvovirus promoter sequence, a herpesvirus promoter sequence, a poxvirus promoter sequence, an adeno-associated virus promoter sequence, a semiliki forest virus promoter sequence, an SV40 promoter sequence, a vaccinia virus promoter sequence, a lentivirus promoter, or a retrovirus promoter sequence.

In further embodiments, the promoter sequence is a tissue selective promoter sequence. A "tissue selective promoter sequence" is defined herein to refer to a control sequence that is a region of a nucleic acid sequence at which initiation and rate of transcription are controlled, wherein the sequence is active in cells of a particular lineage or tissue type. For example, the tissue-selective promoter sequence may be a promoter sequence that is active in normal and/or diseased heart, lung, esophagus, muscle, intestine, breast, prostate, stomach, bladder, liver, spleen, pancreas, kidney, neurons, myocytes, leukocytes, immortalized cells, neoplastic cells, tumor cells, cancer cells, duodenum, jejunum, ileum, cecum, colon, rectum, salivary glands, gall bladder, urinary bladder, trachea, larynx, pharynx, aorta, arteries, capillaries, veins, thymus, lymph nodes, bone marrow, pituitary gland, thyroid gland, parathyroid glands, adrenal glands, brain, cerebrum, cerebellum, medulla, pons, spinal cord, nerves, skeletal muscle, smooth muscle, bone, testes, epidiymides, prostate, seminal vesicles, penis, ovaries, uterus, mammary glands, vagina, skin, eyes, or optic nerve.

In some embodiments, the tissue-selective promoter sequence is an hTR promoter sequence, a hTERT promoter sequence, a CEA promoter sequence, a PSA promoter sequence promoter sequence, a probasin promoter sequence, a ARR2PB promoter sequence, an AFP promoter sequence, a MUC-I promoter sequence, a MUC-4 promoter sequence, a mucin-like glycoprotein promoter sequence, a C-erbB2/neu oncogene promoter sequence, a cyclo-oxygenase promoter sequence, a E2F transcription factor 1 promoter sequence, a tyrosinase related protein promoter sequence, a tyrosinase promoter sequence, a survivin promoter sequence, a Tcf1-alpha promoter sequence, a Ras promoter sequence, a Raf promoter sequence, a cyclin E promoter sequence, a Cdc25A promoter sequence, a HK II promoter sequence, a KRT 19 promoter sequence, a TFF1 promoter sequence, a SEL1L promoter sequence, or a CEL promoter sequence.

Other examples of tissue-selective promoter sequences include an immunoglobulin heavy chain promoter sequence, an immunoglobulin light chain promoter sequence, a T-cell receptor promoter sequence, an HLA DQ a promoter sequence, an HLA DQ beta promoter sequence, a beta-interferon promoter sequence, an interleukin-2 promoter sequence, an interleukin-2 receptor promoter sequence, an MHC Class II 5 promoter sequence, an MHC Class II HLA-Dra promoter sequence, a muscle creatine kinase (MCK) promoter sequence, a prealbumin (transthyretin) promoter sequence, an albumin promoter sequence, an alpha-fetoprotein promoter sequence, a gamma-globin promoter sequence, a beta-globin promoter sequence, a, an insulin promoter sequence, a neural cell adhesion molecule (NCAM) promoter sequence, an alpha-1-antitrypsin promoter sequence, a growth hormone promoter sequence, a human serum amyoid A (SAA) promoter sequence, a troponin I (TN I) promoter sequence, a Duchenne Muscular Dystrophy promoter sequence, an SV40 promoter sequence, a Hepatitis B virus promoter sequence, a Gibbon Ape Leukemia Virus promoter sequence, a somatostatin receptor promoter sequence, a human CD4 promoter sequence, a human alpha-lactalbumin promoter sequence, a human Y promoter sequence, an alpha fetoprotein promoter sequence, a monocyte receptor for bacterial LPS promoter sequence, a leukocyte common antigen promoter sequence, a Desmin promoter sequence, a VEGF receptor promoter sequence, a glial fibrillary acidic protein promoter sequence, an interferon beta promoter sequence, a myoglobin promoter sequence, an osteocalcin 2 promoter sequence, a prostate specific antigen promoter sequence, a prostate specific membrane antigen promoter sequence, a surfactant protein B promoter sequence, a Synapsin promoter sequence, a tyrosinase related protein promoter sequence, a tyrosinase promoter sequence, a functional hybrid, functional portion, or a combination of any of the aforementioned promoter sequences. Some promoters may be both lineage specific and functional (e.g., albumin). Other examples of promoter sequences include a collagenase promoter sequence, an H2B (TH2B) histone promoter sequence, a type I collagen promoter sequence, a GRP94 promoter sequence, a GRP78 promoter sequence, a glucose-regulated protein promoter sequence, a Human Immunodeficiency Virus promoter sequence, a human LIMK2 gene promoter sequence, a murine epididymal retinoic acid-binding gene promoter sequence, a mouse alpha2 (XI) collagen promoter sequence, a D1A dopamine receptor promoter sequence, an insulin-like growth factor II promoter sequence, a human platelet endothelial cell adhesion molecule-1 promoter sequence, a 7SL promoter sequence, a human MRP-7-2 promoter sequence, a leukosialin promoter sequence, a Sialophorin promoter sequence, a Macrosialin or human analogue of macrosialin promoter sequence, and an Endoglin promoter sequence. To overcome weak expression, promoters and nucleic acids of the invention may be included in an amplified promoter system. An amplified promoter system typically includes a nucleic acid sequence encoding a transactivator under the control of a promoter such as a tissue specific promoter or a core promoter. The encoded transactivator is coupled or present in a cell with a second nucleic acid including a nucleic acid(s) of interest, such as a reporter or therapeutic, which is under the control of a promoter activated by the transactivator. In certain embodiments the transactivator is a GalVP 16 transactivator. The GalVP 16 may include a varying number of GAL and/or VP 16 within the construct. The GalVP 16 may include one or more genes linked to the GalVP 16.

The nucleic acids of the amplified promoter system may or may not be operatively coupled to a core promoter sequence. A core promoter sequence is defined herein to refer to a nucleotide sequence that maintains the ability to bind and locate a transactivator or a component of a transcription complex to a particular location in a nucleic acid. In some embodiments, tissue-selective promoter sequence is operatively coupled to a core promoter sequence. The core promoter sequence can be any core promoter sequence known to those of ordinary skill in the art, such as a minimal viral promoter sequence. A minimal viral promoter sequence can be any minimal viral promoter sequence known to those of ordinary skill in the art. For example, the minimal viral promoter sequence may be an RNA virus promoter, DNA virus promoter, adenoviral promoter sequence, a baculoviral promoter sequence, a CMV promoter sequence, a parvovirus promoter sequence, a herpesvirus promoter sequence, a poxvirus promoter sequence, an adeno-associated virus promoter sequence, a semiliki forest virus promoter sequence, an SV40 promoter sequence, a vaccinia virus promoter sequence, a lentivirus promoter, a reovirus promoter, or a retrovirus promoter sequence. In particular embodiments, the minimal viral promoter sequence is a mini-CMV promoter sequence.

B. Internal Ribosome Entry Sites (IRES)

In certain embodiments of the invention, internal ribosome entry site (IRES) elements are used to create multi-gene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991) and further sequences as well as modified versions are envisioned in this application for invention. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; and PCT application PCT/US99/05781) and are envision in this application for invention. The order (upstream or downstream of the IRES) of the reporter and gene(s) of interest is not important for the invention. More than one gene of interest may be linked.

C. Selectable Markers

In certain embodiments of the invention, a nucleic acid construct of the present invention may be isolated or selected for in vitro or in vivo by including a selectable marker in the expression vector. Such selectable markers would confer an identifiable characteristic to the cell permitting easy identification, isolation and/or selection of cells containing the expression vector. A positive selectable marker is one in which the presence of the marker allows for its selection, while a negative selectable marker is one in which its presence prevents its selection. An example of a positive selectable marker is a drug resistance marker. Examples of selectable and screenable markers are well known to one of skill in the art.

D. Other Elements of Expression Cassettes

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (Chandler et al, 1997).

One may include a polyadenylation signal in the expression construct to effect proper polyadenylation of the transcript. The nature of the polyadenylation signal is not believed to be crucial to the successful practice of the invention, and/or any such sequence may be employed. Specific embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences. The vectors or constructs of the present invention may comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, the terminator may comprise a signal for the cleavage of the RNA, and it is more specific that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

IX. Gene Delivery

Aspects of the invention include transferring into a cell an expression construct comprising a nucleic acid sequence encoding a somatostatin receptor or its mutant. Techniques pertaining to the transfer of expression constructs into cells are well-known to those of ordinary skill in the art. Exemplary techniques are discussed below.

A. Viral Vectors

In certain embodiments of the present invention, transfer of an expression construct into a cell is accomplished using a viral vector. Techniques using "viral vectors" are well-known in the art. A viral vector is meant to include those constructs containing viral sequences sufficient to (a) support packaging of the expression cassette and (b) to ultimately express a recombinant gene construct that has been cloned therein.

In particular embodiments, the viral vector is a lentivirus vector. Lentivirus vectors have been successfully used in infecting stem cells and providing long term expression.

Another method for delivery of a nucleic acid involves the use of an adenovirus vector. Adenovirus vectors are known to have a low capacity for integration into genomic DNA. Adenovirus vectors result in highly efficient gene transfer.

Adenoviruses are currently the most commonly used vector for gene transfer in clinical settings. Among the advantages of these viruses is that they are efficient at gene delivery to both nondividing and dividing cells and can be produced in large quantities. The vector comprises a genetically engineered form of adenovirus (Grunhaus et al, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. A person of ordinary skill in the art would be familiar with experimental methods using adenoviral vectors.

The adenovirus vector may be replication defective, or at least conditionally defective, and the nature of the adenovirus vector is not believed to be crucial to the successful practice of the invention. The adenovirus may be of any of the 42 different known serotypes or subgroups A-F and other serotypes or subgroups are envisioned. Adenovirus type 5 of subgroup C is the starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector. Adenovirus growth and manipulation is known to those of skill in the art, and exhibits broad host range in vitro and in vivo. Modified viruses, such as adenoviruses with alteration of the CAR domain, may also be used. Methods for enhancing delivery or evading an immune response, such as liposome encapsulation of the virus, are also envisioned. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains two long terminal repeat (LTR) sequences present at the 5' and 3' ends of the viral genome. These contain strong promoter and enhancer sequences and are also required for integration in the host cell genome (Coffin, 1990).

In order to construct a retroviral vector, a nucleic acid encoding a nucleic acid or gene of interest is inserted into the viral genome in the place of certain viral sequences to produce a virus that is replication-defective. A person of ordinary skill in the art would be familiar with well-known techniques that are available to construct a retroviral vector. Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin et al, 1986; Lebkowski et al, 1988; McLaughlin et al, 1988), which means it is applicable for use with the present invention. Details concerning the generation and use of rAAV vectors are described in U.S. Pat. Nos. 5,139,941 and 4,797,368, each incorporated herein by reference.

Typically, recombinant AAV (rAAV) virus is made by cotransfecting a plasmid containing the gene of interest flanked by the two AAV terminal repeats (McLaughlin et al, 1988; Samulski et al, 1989; each incorporated herein by reference) and an expression plasmid containing the wild-type AAV coding sequences without the terminal repeats, for example pIM45 (McCarty et al., 1991; incorporated herein by reference). A person of ordinary skill in the art would be familiar with techniques available to generate vectors using AAV virus.

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995). A person of ordinary skill in the art would be familiar with well-known techniques for use of HSV as vectors.

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome.

Other viral vectors may be employed as constructs in the present invention. For example, vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and it has been suggested that VEE may be an extremely useful vector for immunizations (Caley et al., 1997). It is contemplated in the present invention, that VEE virus may be useful in targeting dendritic cells.

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Nonviral Gene Transfer

Several non-viral methods for the transfer of nucleic acids into cells also are contemplated by certain aspects of the present invention. These include calcium phosphate precipitation (Graham and Van Der Eb, 1973; Chen and Okayama, 1987; Rippe et al, 1990) DEAE-dextran (Gopal, 1985), electroporation (Tur-Kaspa et al, 1986; Potter et al, 1984), nucleofection (Trompeter et al, 2003), direct microinjection (Harland and Weintraub, 1985), DNA-loaded liposomes (Nicolau and Sene, 1982; Fraley et al, 1979) and lipofectamine-DNA complexes, polyamino acids, cell sonication (Fechheimer et al, 1987), gene bombardment using high velocity microprojectiles (Yang et al, 1990), polycations (Boussif et al, 1995) and receptor-mediated transfection (Wu and Wu, 1987; Wu and Wu, 1988). Some of these techniques may be successfully adapted for in vivo or ex vivo use. A person of ordinary skill in the art would be familiar with the techniques pertaining to use of nonviral vectors, and would understand that other types of nonviral vectors than those disclosed herein are contemplated by the present invention. In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. Also contemplated is a gene construct complexed with Lipofectamine (Gibco BRL). One of ordinary skill in the art would be familiar with techniques utilizing liposomes and lipid formulations.

X. Kits

The present invention provides kits, such as diagnostic and therapeutic kits based on cellular therapy and/or gene therapy. For example, a kit may comprise one or more pharmaceutical compositions as described herein and optionally instructions for their use. Kits may also comprise one or more devices for accomplishing administration of such compositions. For example, a subject kit may comprise a pharmaceutical composition and catheter for accomplishing direct intraarterial injection of the composition into a cancerous tumor. In other embodiments, a subject kit may comprise pre-filled ampoules of a protein isoform specific antibody construct, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

XI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
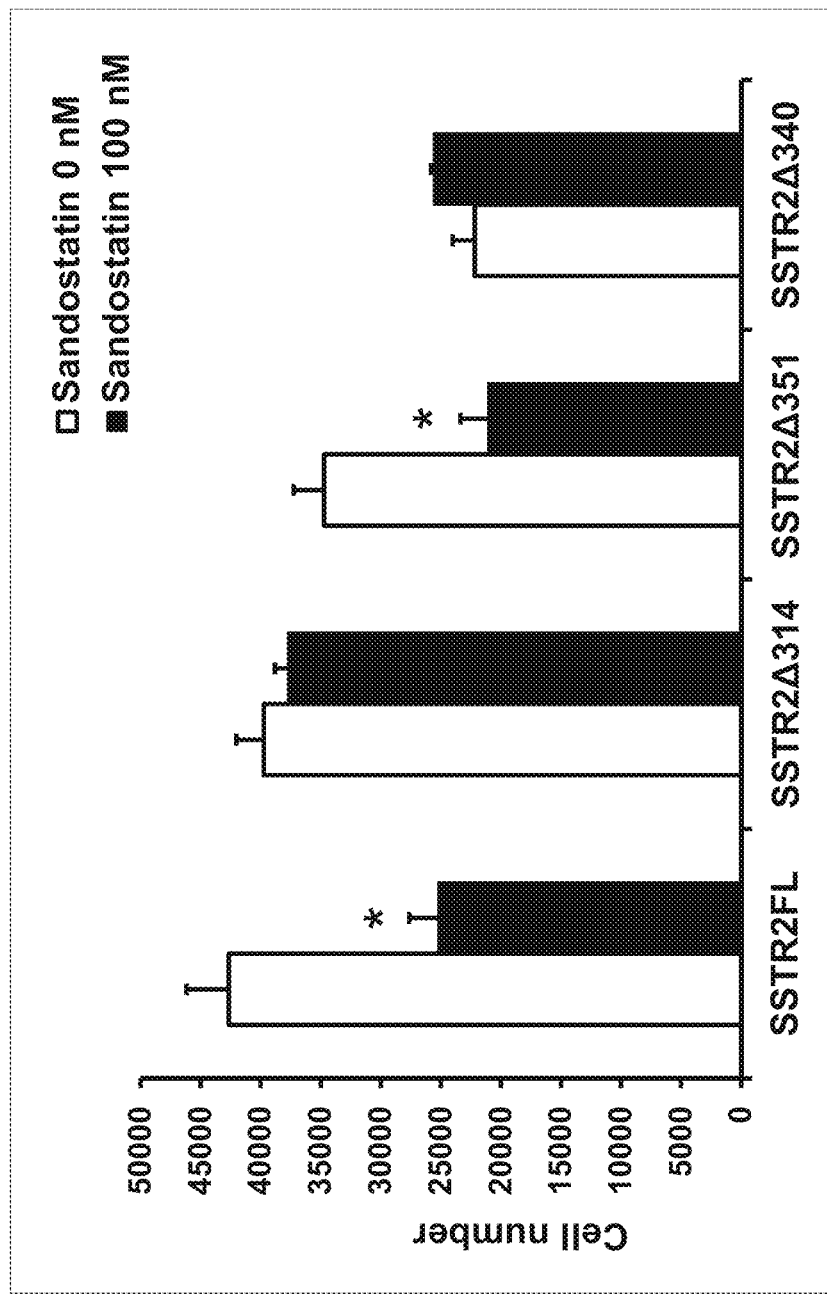
FIG. 1: Human HA-SSTR2D314 does not inhibit cellular growth upon ligand stimulation; whereas HA-SSTR2D340 inhibits growth even without ligand stimulation, similar to Inhibition by wild-type receptor upon activation with ligand. 3000 cells HT1080 cells (fibrosarcoma cells that do not endogenously express SSTR2) stably transfected with HA-SSTR2 wild-type (FL) or C-terminal deletions were grown in the presence of 5% FBS with or without 100 nM of the somatostatin analogue, sandostatin. Three days later, MTT assay was used to determine cell number.

In the following experiments, HA-tagged receptors were used. In vitro experiments demonstrate that the delta340 mutant inhibits cell growth without ligand in both transiently transfected cells and stably transfected cells, whereas cells expressing wild-type SSTR2 require ligand stimulation to inhibit growth and vector control cells do not inhibit growth regardless of ligand presence. Human HA-SSTR2D314 does not inhibit cellular growth upon ligand stimulation, whereas HA-SSTR2D340 inhibits growth even without ligand stimulation, similar to inhibition by wild-type receptor upon activation with ligand (FIG. 1).

Figure 2:
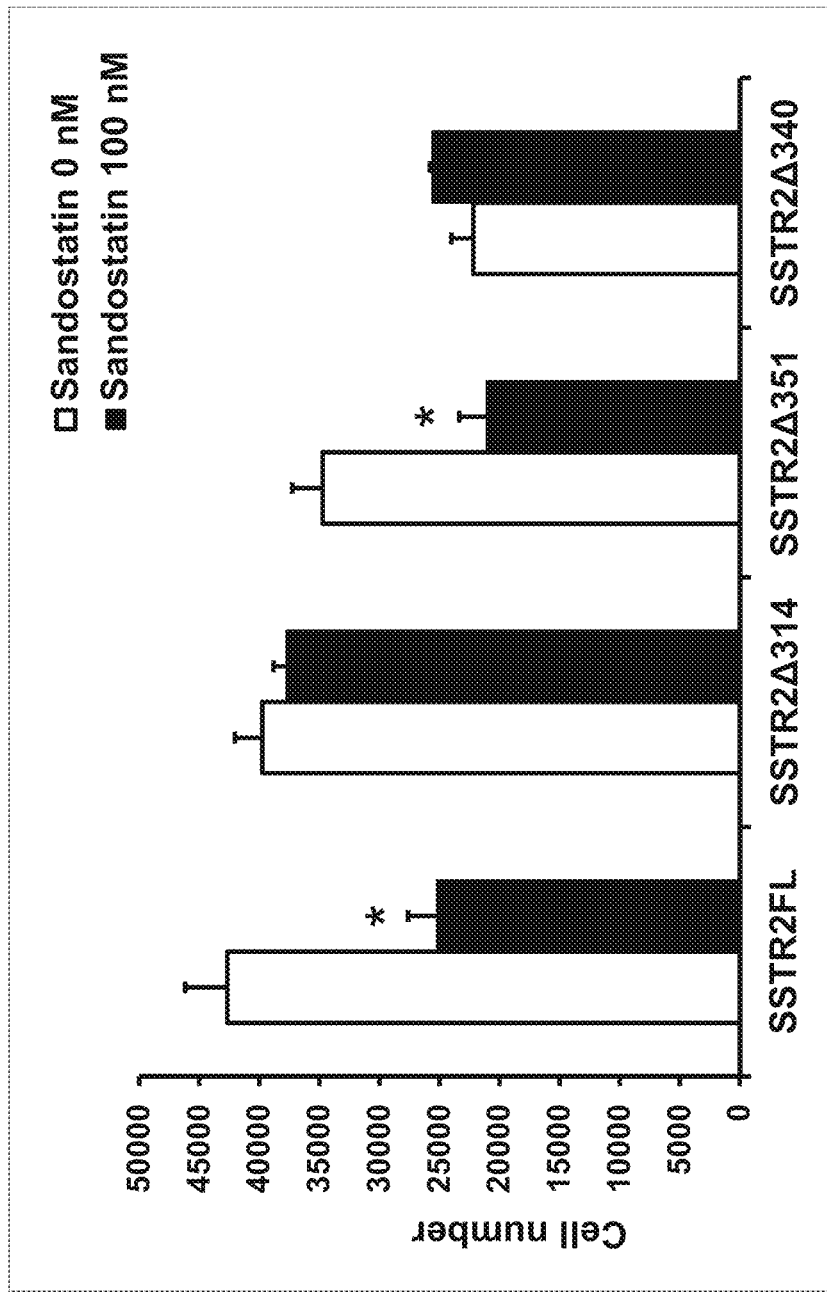
FIG. 2: Human HA-SSTR2D340 Inhibits growth even without ligand stimulation. Two days after transient transfection with HA-SSTR2D351 or HA-SSTR2D340, 3000

Human HA-SSTR2D340 was confirmed to inhibit growth even without ligand stimulation (FIG. 2). Two days after transient transfection with HA-SSTR2D351 or HA-SSTR2D340, 3000 HT1080 cells were grown in the presence of 5% FBS with or without 100 nM of the somatostatin analogue sandostatin. Three days later, MTT assay was used to determine cell number. Stable transfectants, wild-type receptor (SSTR2FL) was used as a positive control for ligand responsive growth inhibition and HA-SSTR2D314 does not inhibit growth upon ligand stimulation. HA-SSTR2D351 or HA-SSTR2D340 demonstrated equivalent amounts of expression (data not shown). As shown in FIG. 12, constitutively active SSTR2delta340 inhibits the growth of tumor cells in vivo.

In vitro experiments demonstrate that in a dose dependent manner, 90-Y-octreotate induces cell kill in cells expressing wild-type and signaling deficient mutant delta314 more than vector-transfected cells (FIGS. 3A-B). Stably transfected HT1080 cells were exposed to different amounts of 90Y-DOTATATE for 1 hour and 72 hours. Dose dependent and time dependent killing was observed in HT1080 cells expressing wild-type or signaling deficient HA-SSTR2 receptors, but not vector transfected cells. Cell death was assessed by trypan blue uptake. *p<0.05 vs Vector.

Mixing mesenchymal stem cells expressing SSTR2 or the signaling deficient mutant delta 314 with untransfected tumor cells results in kill of rosettes of clusters of cells that are not seen if mesenchymal stem cells transfected with vector are used (FIG. 4), consistent with bystander killing. Human mesenchymal stem cells (HS5) stably expressing wild-type or signaling deficient HA-SSTR2 receptors or transfected with vector were admixed with untransfected HT1080 cells and then exposed to 90Y-DOTATATE for 24 hours. Rosettes (clusters) of dead cells were seen in wells containing mesenchymal stem cells stably expressing wild-type or signaling deficient HA-SSTR2 receptors but not in wells containing mesenchymal stem cells transfected with vector.

In vivo, addition of unlabeled somatostatin analogue octreotide inhibited growth of tumors expressing wild-type receptor, but not the signaling deficient receptor (FIG. 5). Stably transfected HT1080 cells were implanted subcutaneously in nude mice (three tumors, HA-wt, HA-D314, vector, per animal). When tumors were palpable, daily injections of the somatostatin analogue sandostatin were initiated and tumors were measured by calipers every two days. Receptor activation by octreotide inhibited growth of tumors expressing wild-type receptor, but no decrease in tumor size was seen with the signaling deficient receptor. Thus, a signaling active receptor can inhibit tumor growth.

The same finding was noted with $^{111}$-In octreotide implying that this imaging agent affects tumor growth via the biologic effect of octreotide and not the radioactivity (FIG. 6A). The imaging agent $^{111}$-In-octreotide inhibited growth of tumors expressing the wild-type receptor, but not the signaling deficient receptor or tumors derived from vector transfected cells. Stably transfected HT1080 cells were implanted subcutaneously in nude mice (three tumors, HA-wt, HA-D314, vector, per animal). When tumors were palpable, 0.9 mCi of $^{111}$-In octreotide was given IV on day 4 and day 6. Tumors were measured by calipers every two days. *p<0.05 SSTR2FL vs Vector. This suggests that tumor growth may be inhibited via activation of SSTR signaling in cells with functional SSTR signaling.

Expression of SSTR2 can be imaged in tumors expressing wild-type or signaling deficient HA-SSTR2 (FIG. 6B). Gamma-camera imaging of mice at 24 hours and 48 hours after the first and 24 hours after the second $^{111}$-In octreotide injection. Uptake (degree of receptor expression) is similar in tumors expressing wild-type or signaling deficient HA-SSTR2 at 24 hours and wanes in both at 48 hours. Increased uptake is again seen 24 hours after the second $^{111}$-In octreotide injection. Minimal uptake is seen in tumors derived from cells transfected with vector. Thus, both wild-type and signaling deficient SSTR2 uptake $^{111}$-In octreotide.

In comparison, 90Y-octreotate inhibited growth of tumors expressing wild-type or signaling deficient receptors (FIGS. 7A-7B). The latter was noted to be dose dependent. Stably transfected HT1080 cells were implanted subcutaneously in nude mice (three tumors, HA-wt, HA-D314, vector, per animal). When tumors were palpable, 90Y-octreotate was given once at a dose of 1 mCi (FIG. 7A) or twice at doses of 2 mCi and 1 mCi (FIG. 7B). Tumors were measured by calipers every two days. *p<0.05 HA-SSTR2FL or HA-D314 vs Vector. Tumors expressing the signaling deficient receptor decreased in size in a dose dependent manner due to the effect of radioactivity on the tumor. Reduction in size of tumors expressing wild-type HA-SSTR2 was due to a combination of effects of receptor activation by the somatoatatin analogue octreotate and effects of radioactivity. This suggests that tumor growth may be inhibited by other mechanisms such as radiation-induced damage in cells without functional SSTR signaling but expressing SSTR's.

Stem cells expressing the signaling deficient mutant SSTR2D314 incorporated into tumor and can be targeted with a therapeutic for inhibiting tumor growth (FIG. 8). 90Y-octreotate (primarily beta emitter) inhibited growth of human tumors incorporating HS5 human mesenchymal stem cells expressing SSTR2D314, but not control HS5 cells. Human ovarian cancer (Hey A8) cells were co-injected subcutaneously in nude mice with HS5 cells expressing or not expressing HA-SSTR2D314. (Previous experiments demonstrated that HS5 cells alone do not form tumors). Once tumors were established, 90Y-octreotate was delivered intravenously. Tumors were measured by calipers every two days. Tumors incorporating HS5 cells expressing the HA-SSTR2D314 mutant were growth inhibited compared to control (*p<0.05, HeyA8+HS5-SSTR2D314 vs HeyA8+HS5vector). The incorporated stem cells, but not the tumor cells, serve as a target for the therapeutic. Data suggest that human stem cells expressing a signaling deficient SSTR2 mutant that were incorporated into human tumor and can serve as a therapeutic target for inhibiting established tumor growth.

Stem cells expressing the signaling deficient mutant SSTR2D314 home to and incorporate into tumor and can be targeted with a therapeutic for inhibiting tumor growth (FIG. 9). 90Y-octreotate (primarily beta emitter) inhibited growth of human tumors to which human mesenchymal stem cells expressing HA-SSTR2D314 homed and incorporated, but not control HS5 cells. Human ovarian cancer (Hey A8) cells on one side and vehicle on the other side were injected subcutaneously in nude. Two days later, human mesenchymal stem cells (HS5 cells) expressing or not expressing HA-SSTR2D314 were injected systemically (intracardiac). No tumors were seen in the side injected with vehicle. Tumors were seen on the side injected with HeyA8 cells. Once tumors were established, 90Y-octreotate was delivered intravenously. Tumors were measured by calipers every two days. Tumors to which HS5 cells expressing the HA-SSTR2D314 mutant homed and incorporated were growth inhibited compared to control (*p<0.05, HeyA8+HS5-SSTR2D314 vs HeyA8+HS5vector). The incorporated stem cells not the tumor cells serve as a target for the therapeutic. Data suggest that systemically delivered human stem cells expressing a signaling deficient SSTR2 mutant home to and incorporate into human tumors and can serve as a therapeutic target for inhibiting established tumor growth. This suggests that established tumors and likely (micro) metastases can be targeted by this method.

After intracardiac injection, human MSC's traffic to HeyA8 tumors; and expression of the signaling deficient SSTR2 mutant in such MSC's can be distinguished (FIG. 10). As can be seen in FIG. 10, left panel, the 111-In-octreotate signal could be visualized in the "HS5-HA-hSSTRs-SD" treated panel, above left, whereas no such signal could be seen in the control vector panel, below left. In particular, HS5 cells expressing signaling deficient human SSTR2 (HS5-HA-hSSTR2-SD) injected intracardiac localized to Hey A8 tumors in mice and could be visualized one day after 111-In-octreotide injection (arrow, middle panel, top) whereas background signal was seen with control HS5 cells transfected with vector (arrow, middle panel, bottom). After imaging, tumors were removed and evaluated, confirming the imaging findings. Right panel: Biodistribution demonstrated increased uptake of 111-In-octreotide in tumors from animals injected intracardiac with HS5 cells expressing signaling deficient human SSTR2 (HA-hSSTR2-SD) compared to injected with HS5 cells transfected with vector. Inset: Western blot using an antibody to the HA domain of signaling deficient HA-SSTR2 demonstrated expression of the reporter by HS5 cells in tumors from animals injected intracardiac with HS5 cells expressing signaling deficient human SSTR2 (top arrow, left, Anti-HA-11) but not with HS5 cells transfected with vector (top arrow, right, Anti-HA-li). Beta-actin, a control house-keeping protein expected to be found in all tumors, was seen in both tumor lysates (bottom arrow, Anti-beta-actin) as expected.

After tumors were present in three locations per mouse in all 8 mice, the animals were injected i.v. with 90-Y labeled octreotate two days and 5 days later as on the chart. Tumor size was measured by calipers. Unlike many stem cells, embryonic stem cells (ES) more commonly form teratomas. Inhibition of growth of established teratomas was assessed. Growth of teratomas expressing HA-SSTR2 (ES-FL) or signaling deficient HA-SSTR2-delta 314 (ES+delta314) was inhibited, compared to wild type teratomas (FIG. 11). This adds a safety factor and suggests that if delivered cells become neoplastic, their growth may be inhibited by targeting SSTR or their mutants or chimeras.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 4,797,368
U.S. Pat. No. 5,139,941
U.S. Pat. No. 5,670,148
U.S. Pat. No. 5,925,565
U.S. Pat. No. 5,928,906
U.S. Pat. No. 5,935,819
U.S. Pat. No. 6,927,060
U.S. Pat. No. 7,078,032

U.S. Patent Publn. 20020173626
Alam and Cook, *Anal. Biochem.*, 188:245-254, 1990.
Bell et al., *Trends Neurosciences*, 16:34-38, 1993.
Boussif et al., *Proc. Natl. Acad. Sci. USA*, 92(16):7297-7301, 1995.
Caley et al., *J. Virology*, 71(4):3031-3038, 1997.
Chandler et al., *Proc. Natl. Acad. Sci. USA*, 94(8):3596-601, 1997.
Chen and Okayama, *Mol. Cell Biol.*, 7(8):2745-2752, 1987.
Coffin, In: *Virology*, Fields et al. (Eds.), Raven Press, NY, 1437-1500, 1990.
Davis et al, *Curr. Biol.*, 6:146-148, 1996.
Dubey et al., *Proc. Natl. Acad. Sci. USA*, 100(3):1232-1237, 2003.
Ducreux et al., *Am. J. Gastroenterol.*, 95:3276-3281, 2000.
Fechheimer, et al., *Proc Natl. Acad. Sci. USA*, 84:8463-8467, 1987.
Fraley et al., *Proc. Natl. Acad. Sci. USA*, 76:3348-3352, 1979.
Gambhir et al., *Nucl. Med. Biol.*, 26:481-490, 1999.
Glorioso et al., *Mol. Biotechnol.*, 4(1):87-99, 1995.
Graham and Van Der Eb, *Virology*, 52:456-467, 1973.
Grunhaus and Horwitz, *Seminar in Virology*, 3:237-252, 1992.
Harland and Weintraub, *J. Cell Biol.*, 101(3):1094-1099, 1985.
Henson et al., *AJNR Am. J. Neuroradiol.*, 25(6):969-972, 2004.
John et al., *Gut.*, 38(1):33-39, 1996.
Kluxen et al., *Proc. Natl. Acad. Sci. USA*, 89:4618-4622, 1992.
Koehne et al., *Nat. Biotechnol.*, 21(4):405-413, 2003.
Kundra et al., *J. Nucl. Med.*, 43(3):406-412, 2002.
Kwekkeboom et al., *J. Nucl. Med.*, 41:1704-1713, 2000.
Lamberts et al., *Front Neuroendoc.*, 22:309-339, 2001.
Laughlin et al., *J. Virol.*, 60(2):515-524, 1986.
Lebkowski et al., *Mol. Cell. Biol.*, 8(10):3988-3996, 1988.
Li et al., *J. Bio. Chem.*, 266:6562-6570, 1990.
Lopez et al., *FASEB. J.*, 15:2300-2302, 2001.
Macejak and Sarnow, *Nature*, 353:90-94, 1991.
McCarty et al., *J. Virol.*, 65(6):2936-2945, 1991.
McLaughlin et al., *J. Virol.*, 62(6): 1963-1973, 1988.
Muzyczka, *Curr. Topics Microbiol. Immunol.*, 158:97-129, 1992.
Nikou et al., *Hepatogastroenterology*, 52:731-741, 2005.
Nicolau and Sene, *Biochim. Biophys. Acta*, 721:185-190, 1982.
O'Carroll et al., *Mol. Pharmacol.*, 42:939-946, 1993.
O'Carroll et al., *Molec. Pharmacology*, 44:1278, 1993.
Panetta et al., *Molec. Pharmacology*, 45:417-427, 1994.
PCT Appln. PCT/US99/05781
Pelletier and Sonenberg, *Nature*, 334(6180):320-325, 1988.
Petersenn et al., *Molec. Cell. Endocrinology*, 157:75-85, 1999.
Potter et al., *Proc. Natl. Acad. Sci. USA*, 81:7161-7165, 1984.
Remington's Pharmaceutical Sciences, 18th Ed. Mack Printing Company, 1990, pp. 1289-1329
Rippe, et al., *Mol. Cell Biol.*, 10:689-695, 1990.
Roux et al., *Proc. Natl. Acad. Sci. USA*, 86:9079-9083, 1989.
Sambrook and Russell, *Molecular Cloning: A Laboratory Manual* 3$^{rd}$ Ed., Cold Spring Harbor Laboratory Press, 2001.
Samulski et al., *J. Virol.*, 63:3822-3828, 1989.
Schwartkop et al., *J. Neurochem.*, 72:1275-1282, 1999.
Strunk and Schild, *Eur. Radiol.*, 14(6):1055-1062, 2004.
Termanini et al., *Gastroenterology*, 112:335-347, 1997.
Tratschin et al., *Mol. Cell. Biol.*, 4:2072-2081, 1984.
Trinklein et al., *Genome Res.*, 14(1):62-66, 2004.
Trompeter et al, *J. Immunol. Methods*, 274(1-2):245-56, 2003.
Tur-Kaspa et al., *Mol. Cell Biol.*, 6:716-718, 1986.
Vanetti et al., *FEBS*, 311(3):290-294, 1992.
Wu and Wu, *Biochemistry*, 27: 887-892, 1988.
Wu and Wu, *J. Biol. Chem.*, 262:4429-4432, 1987.
Wymenga et al., *J. Clin. Oncol.*, 17:1111, 1999.
Yamada et al., *Molec. Endocrinol.*, 6:2136-2142, 1992.
Yamada et al., *Proc. Natl. Acad. Sci. USA*, 89:251-255, 1992.
Yang and Russell, *Proc. Natl. Acad. Sci. USA*, 87:4144-4148, 1990.
Yang et al., *Radiology*, 235:950-958, 2005.
Yutzey et al., *Mol. and Cell. Bio.*, 9:1397-1405, 1989.

The invention claimed is:

1. A method of treating a tumor, comprising the steps of:
   a) providing cells comprising stem cells, progeny of stem cells, or fibroblasts, wherein the cells are capable of localizing to a tumor;
   b) introducing the stem cells, progeny of stem cells or fibroblasts to a subject having a tumor wherein said introduced cells localize to the tumor; and
   c) administering to the subject an anti-tumor radiotherapeutic or thermal therapeutic that binds the cells and effects a damage on the tumor.

2. The method of claim 1, wherein the stem cells, the progeny of stem cells or the fibroblasts comprise a nucleic acid molecule, wherein the nucleic acid molecule or its encoded protein is capable of binding a radiotherapeutic or thermal therapeutic.

3. The method of claim 2, wherein the stem cell, the progeny of stem cells or the fibroblasts comprise a nucleic acid encoding a protein sequence selected from the group consisting of a protein tag gene, a reporter gene, a therapeutic gene, a signaling sequence, and a trafficking sequence.

4. The method of claim 1, wherein the stem cells, the progeny of stems cells or the fibroblasts comprise a nucleic acid molecule encoding a somatostatin receptor.

5. The method of claim 1, wherein the stem cells are induced pluripotent stem cells, embryonic stem cells, somatic stem cells, germ stem cells, epidermal stem cells, and/or tissue-specific stem cells.

6. The method of claim 1, wherein the stem cells are mesenchymal stem cells.

7. The method of claim 1, wherein the stem cells are pluripotent stem cells.

8. The method of claim 1, wherein an anti-tumor radiotherapeutic is administered to the subject.

9. The method of claim 8, wherein the radiotherapeutic comprises a therapeutic radionuclide.

10. The method of claim 9, wherein the therapeutic radionuclide is a $\beta^-$ particle emitter.

11. The method of claim 10, wherein the therapeutic radionuclide comprises $^{177}$Lu or $^{90}$Y.

12. The method of claim 1, wherein a thermal therapeutic is administered to the patient.

13. The method of claim 1, wherein the tumor is neuroendocrine tumor, breast tumor, lung tumor, prostate tumor, ovarian tumor, brain tumor, liver tumor, cervical tumor, colon tumor, renal tumor, skin tumor, head and neck tumor, bone tumor, esophageal tumor, bladder tumor, uterine tumor, lymphatic tumor, stomach tumor, pancreatic tumor, testicular tumor, or lymphoma.

* * * * *

SEQUENCE LISTING

```
<160> NUMBER OF SEQ ID NOS: 22

<210> SEQ ID NO 1
<211> LENGTH: 4000
<212> TYPE: DNA
<213> ORGANISM: Homo sapiens
<220> FEATURE:
<221> NAME/KEY: CDS
<222> LOCATION: (275)..(1450)

<400> SEQUENCE: 1
tgcggtgctc ccacatcctg gcctctcctc tccacagtcg cctgtgcccg ggcaccccgg      60
agctgcaaac tgcagagccc aggcaaccgc tgggctgtgc gccccgccgg cgccggtagg     120
agccgcgctc cccgcagcgg ttgcgctcta cccggaggcg ctgggcggct gcgggctgca     180
ggcaagcggt cgggtgggga gggagggcgc aggcggcggg tgcgcgagga gaaagcccca     240
gccctggcag ccccactggc cccctcagc tggg atg ttc ccc aat ggc acc gcc     295
                                 Met Phe Pro Asn Gly Thr Ala
                                   1               5
```

-continued

| | | |
|---|---|---|
| tcc tct cct tcc tcc tct cct agc ccc agc ccg ggc agc tgc ggc gaa<br>Ser Ser Pro Ser Ser Ser Pro Ser Pro Ser Pro Gly Ser Cys Gly Glu<br>10                              15                  20 | 343 |
| ggc ggc ggc agc agg ggc ccc ggg gcc ggc gct gcg gac ggc atg gag<br>Gly Gly Gly Ser Arg Gly Pro Gly Ala Gly Ala Ala Asp Gly Met Glu<br>25                              30                  35 | 391 |
| gag cca ggg cga aat gcg tcc cag aac ggg acc ttg agc gag ggc cag<br>Glu Pro Gly Arg Asn Ala Ser Gln Asn Gly Thr Leu Ser Glu Gly Gln<br>40                              45                  50                  55 | 439 |
| ggc agc gcc atc ctg atc tct ttc atc tac tcc gtg gtg tgc ctg gtg<br>Gly Ser Ala Ile Leu Ile Ser Phe Ile Tyr Ser Val Val Cys Leu Val<br>60                              65                  70 | 487 |
| ggg ctg tgt ggg aac tct atg gtc atc tac gtg atc ctg cgc tat gcc<br>Gly Leu Cys Gly Asn Ser Met Val Ile Tyr Val Ile Leu Arg Tyr Ala<br>75                              80                  85 | 535 |
| aag atg aag acg gcc acc aac atc tac atc cta aat ctg gcc att gct<br>Lys Met Lys Thr Ala Thr Asn Ile Tyr Ile Leu Asn Leu Ala Ile Ala<br>90                              95                  100 | 583 |
| gat gag ctg ctc atg ctc agc gtg ccc ttc cta gtc acc tcc acg ttg<br>Asp Glu Leu Leu Met Leu Ser Val Pro Phe Leu Val Thr Ser Thr Leu<br>105                             110                  115 | 631 |
| ttg cgc cac tgg ccc ttc ggt gcg ctg ctc tgc cgc ctc gtg ctc agc<br>Leu Arg His Trp Pro Phe Gly Ala Leu Leu Cys Arg Leu Val Leu Ser<br>120                            125                  130                  135 | 679 |
| gtg gac gcg gtc aac atg ttc acc agc atc tac tgt ctg act gtg ctc<br>Val Asp Ala Val Asn Met Phe Thr Ser Ile Tyr Cys Leu Thr Val Leu<br>140                            145                  150 | 727 |
| agc gtg gac cgc tac gtg gcc gtg gtg cat ccc atc aag gcg gcc cgc<br>Ser Val Asp Arg Tyr Val Ala Val Val His Pro Ile Lys Ala Ala Arg<br>155                            160                  165 | 775 |
| tac cgc cgg ccc acc gtg gcc aag gta gta aac ctg ggc gtg tgg gtg<br>Tyr Arg Arg Pro Thr Val Ala Lys Val Val Asn Leu Gly Val Trp Val<br>170                            175                  180 | 823 |
| cta tcg ctg ctc gtc atc ctg ccc atc gtg gtc ttc tct cgc acc gcg<br>Leu Ser Leu Leu Val Ile Leu Pro Ile Val Val Phe Ser Arg Thr Ala<br>185                            190                  195 | 871 |
| gcc aac agc gac ggc acg gtg gct tgc aac atg ctc atg cca gag ccc<br>Ala Asn Ser Asp Gly Thr Val Ala Cys Asn Met Leu Met Pro Glu Pro<br>200                            205                  210                  215 | 919 |
| gct caa cgc tgg ctg gtg ggc ttc gtg ttg tac aca ttt ctc atg ggc<br>Ala Gln Arg Trp Leu Val Gly Phe Val Leu Tyr Thr Phe Leu Met Gly<br>220                            225                  230 | 967 |
| ttc ctg ctg ccc gtg ggg gct atc tgc ctg tgc tac gtg ctc atc att<br>Phe Leu Leu Pro Val Gly Ala Ile Cys Leu Cys Tyr Val Leu Ile Ile<br>235                            240                  245 | 1015 |
| gct aag atg cgc atg gtg gcc ctc aag gcc ggc tgg cag cag cgc aag<br>Ala Lys Met Arg Met Val Ala Leu Lys Ala Gly Trp Gln Gln Arg Lys<br>250                            255                  260 | 1063 |
| cgc tcg gag cgc aag atc acc tta atg gtg atg atg gtg gtg atg gtg<br>Arg Ser Glu Arg Lys Ile Thr Leu Met Val Met Met Val Val Met Val<br>265                            270                  275 | 1111 |
| ttt gtc atc tgc tgg atg cct ttc tac gtg gtg cag ctg gtc aac gtg<br>Phe Val Ile Cys Trp Met Pro Phe Tyr Val Val Gln Leu Val Asn Val<br>280                            285                  290                  295 | 1159 |
| ttt gct gag cag gac gac gcc acg gtg agt cag ctg tcg gtc atc ctc<br>Phe Ala Glu Gln Asp Asp Ala Thr Val Ser Gln Leu Ser Val Ile Leu<br>300                            305                  310 | 1207 |
| ggc tat gcc aac agc tgc gcc aac ccc atc ctc tat ggc ttt ctc tca<br>Gly Tyr Ala Asn Ser Cys Ala Asn Pro Ile Leu Tyr Gly Phe Leu Ser<br>315                            320                  325 | 1255 |

-continued

```
gac aac ttc aag cgc tct ttc caa cgc atc cta tgc ctc agc tgg atg     1303
Asp Asn Phe Lys Arg Ser Phe Gln Arg Ile Leu Cys Leu Ser Trp Met
            330                 335                 340 gac aac gcc gcg gag gag ccg gtt gac tat tac gcc acc gcg ctc aag     1351
Asp Asn Ala Ala Glu Glu Pro Val Asp Tyr Tyr Ala Thr Ala Leu Lys
345                 350                 355 agc cgt gcc tac agt gtg gaa gac ttc caa cct gag aac ctg gag tcc     1399
Ser Arg Ala Tyr Ser Val Glu Asp Phe Gln Pro Glu Asn Leu Glu Ser
360                 365                 370                 375 ggc ggc gtc ttc cgt aat ggc acc tgc acg tcc cgg atc acg acg ctc     1447
Gly Gly Val Phe Arg Asn Gly Thr Cys Thr Ser Arg Ile Thr Thr Leu
                380                 385                 390 tga gcccgggcca cgcaggggct ctgagcccgg gccacgcagg ggccctgagc           1500
caaaagaggg ggagaatgag aagggaaggc cgggtgcgaa aggacggta tccagggcgc     1560 cagggtgctg tcgggataac gtggggctag acactgaca gcctttgatg gaggaaccca    1620
agaaaggcgc gcgacaatgg tagaagtgag agctttgctt ataaactggg aaggctttca   1680
ggctaccttt ttctgggtct cccactttct gttccttcct ccactgcgct tactcctctg   1740
accctccttc tattttccct accctgcaac ttctatcctt tcttccgcac cgtcccgcca   1800
gtgcagatca cgaactcatt aacaactcat tctgatcctc agcccctcca gtcgttattt   1860
ctgtttgttt aagctgagcc acggataccg ccacggggttt ccctcggcgt tagtccctag  1920
ccgcgcgggg ccgctgtcca ggttctgtct ggtgccccta ctggagtccc gggaatgacc   1980
gctctccctt tgcgcagccc taccttaagg aaagttggac ttgagaaaga tctaagcagc   2040
tggtcttttc tcctactctt gggtgaaggt gcatctttcc ctgccctccc ctgtcccct    2100 ctcgccgccc gccgccacc accactctca ctccacccag agtagagcca ggtgcttagt   2160
aaaataggtc ccgcgcttcg aactccaggc tttctggagt tcccacccaa gccctccttt   2220
ggagcaaaga aggagctgag aacaagccga atgaggagtt tttataagat tgcggggtcg   2280
gagtgtgggc gcgtaatagg aatcaccctc ctactgcgcg ttttcaaaga ccaagcgctg   2340
ggcgctcccg ggccgcgcgt ctgcgttagg cagggcaggg tagtgcaggg cacaccttcc   2400
ccggggttcg gggttcgggg ttcggttgca gggctgcagc ccgccttggc tttctccctc   2460
acccaagttt ccggaggagc cgacctaaaa gtaacaatag ataaggtttc ctgctccagt   2520
gtatctcaaa agaccgggcg ccaggggcgg gggacctagg gcgacgtctt cagagtccgc   2580
cagtgttggc ggtgtcgccg caacctgcag gctcccgagt ggggcctgcc tggtctctag   2640
agggttgctg cctttcaagc ggtgcctaag aagttatttt cttgtttaac atatatattt   2700
attaatttat ttgtcgtgtt ggaaaatgtg tctctgcttt ccttttctct gcttgcctag   2760
ccccaggtct tttctttggg acctggggg cgggcatgga agtggaagta ggggcaagct    2820
cttgccccac tccctggcca tctcaacgcc tctcctcaat gctgggccct cttatctcat   2880
cctttcctct agcttttcta tttttgattg tgttgagtga agtttggaga ttttcatac    2940 ttttcttact atagtctctt gtttgtctta ttaggataat acataaatga taatgtgggt   3000
tatcctcctc tccatgcaca gtggaaagtc ctgaactcct ggctttccag gagacatata   3060 tagggggaaca tcaccctata tataaatttga gtgtatatat atttatatat atgatgtgga   3120
catatgtata cttatcttgc tccattgtca tgagtccatg agtctaagta tagccactga   3180
tggtgacagg tgtgagtctg gctggaacac tttcagtttc aggagtgcaa gcagcactca   3240
aacctggagc tgaggaatct aattcagaca gagactttaa tcactgctga agatgcccct   3300
```

```
gctccctctg ggttccagca gaggtgattc ttacatatga tccagttaac atcatcactt  3360
tttttgagga cattgaaagt gaaataattt gtgtctgtgt ttaatattac caactacatt  3420
ggaagcctga gcagggcgag gaccaataat tttaattatt tatatttcct gtattgcttt  3480
agtatgctgg cttgtacata gtaggcacta aatacatgtt tgttggttga ttgtttaagc  3540
cagagtgtat tacaacaatc tggagatact aaatctgggg ttctcaggtt cactcattga  3600
catgatatac aatggttaaa atcactattg aaaaatacgt tttgtgtata tttgcttcaa  3660
caactttgtg ctttcctgaa agcagtaacc aagagttaag atatccctaa tgttttgctt  3720
aaactaatga acaaatatgc tttgggtcat aaatcagaaa gtttagatct gtcccttaat  3780
aaaaatatat attactactc ctttggaaaa tagattttta atggttaaga actgtgaaat  3840
ttacaaatca aaatcttaat cattatcctt ctaagaggat acaaatttag tgctcttaac  3900
ttgttaccat tgtaatatta actaaataaa cagatgtatt atgctgttaa aaaaaaaaa  3960
aaaaaaaaaa aaaaaaaaaa aaaaaaaaaa aaaaaaaaa                        4000
```

<210> SEQ ID NO 2
<211> LENGTH: 391
<212> TYPE: PRT
<213> ORGANISM: Homo sapiens

<400> SEQUENCE: 2

```
Met Phe Pro Asn Gly Thr Ala Ser Ser Pro Ser Ser Pro Ser Pro
1               5                   10                  15

Ser Pro Gly Ser Cys Gly Glu Gly Gly Ser Arg Gly Pro Gly Ala
            20                  25                  30

Gly Ala Ala Asp Gly Met Glu Glu Pro Gly Arg Asn Ala Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255
```

```
Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Thr Ser Arg Ile Thr Thr Leu
385                 390

<210> SEQ ID NO 3
<211> LENGTH: 2014
<212> TYPE: DNA
<213> ORGANISM: Mus musculus
<220> FEATURE:
<221> NAME/KEY: CDS
<222> LOCATION: (426)..(1601)

<400> SEQUENCE: 3
gagacatcat tgacttgggg atctgaaggc ctgaaatctc caggtacagg tttaaagaac      60
tggcaagcag gaaaggagct gctgacgcga tggtgccgct tattaatcat tcatcagtcc     120
agagcctttc cacttaatgg atgtgccgcg ctgggctcta gcctcttggc ctctcctctc     180
cactctccag tgtgcccagg accccggag ctgcaagaga cagcgctc aagcaagctg        240 ccgctgggtg atgctcccgg cggcctcagt cggagccgcg ctcgccacag ctgctgcgct     300
ctgccgggtg gcgccaggcg gcggtgagct gtgagcttgg ggccttgagc ctagggaggg     360
cgcagacagc aagggcgcaa ggtgagcgcc ccagccggca gccgcaccgg cccacttcag     420 ctggg atg ttc ccc aat ggc acc gcc tcc tct ccc tcc tct tct cca agc    470
      Met Phe Pro Asn Gly Thr Ala Ser Ser Pro Ser Ser Ser Pro Ser
      1               5                  10                  15 ccc agc cca ggc agc tgc ggg gaa gga gcc tgc agc agg ggt ccg ggg      518
Pro Ser Pro Gly Ser Cys Gly Glu Gly Ala Cys Ser Arg Gly Pro Gly
                20                  25                  30 tcc ggc gct gcg gac ggc atg gaa gag cct gga cga aac gct tcc cag      566
Ser Gly Ala Ala Asp Gly Met Glu Glu Pro Gly Arg Asn Ala Ser Gln
            35                  40                  45 aat ggg acc tta agc gag gga cag ggt agc gcc att ctc atc tct ttc      614
Asn Gly Thr Leu Ser Glu Gly Gln Gly Ser Ala Ile Leu Ile Ser Phe
        50                  55                  60 atc tac tcc gtg gta tgc ttg gtg gga ctg tgt ggg aac tct atg gtc      662
Ile Tyr Ser Val Val Cys Leu Val Gly Leu Cys Gly Asn Ser Met Val
65                  70                  75 atc tat gtg atc ctg cgc tac gcc aag atg aag acc gct acc aac atc      710
Ile Tyr Val Ile Leu Arg Tyr Ala Lys Met Lys Thr Ala Thr Asn Ile
    80                  85                  90                  95 tac att cta aac ctg gct att gct gat gag ctg ctc atg ctc agc gtg      758
Tyr Ile Leu Asn Leu Ala Ile Ala Asp Glu Leu Leu Met Leu Ser Val
```

-continued

```
                        100                 105                 110
ccc ttt ctg gtc act tcc acg ctg ttg cgc cac tgg ccc ttc ggc gcg       806
Pro Phe Leu Val Thr Ser Thr Leu Leu Arg His Trp Pro Phe Gly Ala
            115                 120                 125 cta ctt tgc cgc ctg gtg ctc agc gtg gat gcg gtc aac atg ttc acc       854
Leu Leu Cys Arg Leu Val Leu Ser Val Asp Ala Val Asn Met Phe Thr
        130                 135                 140 agc atc tac tgt ctg act gtg ctt agt gtg gac cgc tat gtg gct gtg       902
Ser Ile Tyr Cys Leu Thr Val Leu Ser Val Asp Arg Tyr Val Ala Val
    145                 150                 155 gtg cac ccg atc aag gca gcg cgc tac cgt cgg ccc act gtg gcc aaa       950
Val His Pro Ile Lys Ala Ala Arg Tyr Arg Arg Pro Thr Val Ala Lys
160                 165                 170                 175 gta gtg aac ctg ggc gtg tgg gtc ctg tca tta ctg gtt atc ttg ccc       998
Val Val Asn Leu Gly Val Trp Val Leu Ser Leu Leu Val Ile Leu Pro
                180                 185                 190 atc gtg gtc ttc tca cgc acc gca gcc aac agc gat ggc acg gta gcc      1046
Ile Val Val Phe Ser Arg Thr Ala Ala Asn Ser Asp Gly Thr Val Ala
            195                 200                 205 tgc aac atg ctc atg ccc gag ccc gcc cag cgc tgg ttg gtg ggc ttc      1094
Cys Asn Met Leu Met Pro Glu Pro Ala Gln Arg Trp Leu Val Gly Phe
        210                 215                 220 gtc tta tac aca ttt ctc atg ggc ttc ctg ctg cct gtc ggg gcc att      1142
Val Leu Tyr Thr Phe Leu Met Gly Phe Leu Leu Pro Val Gly Ala Ile
    225                 230                 235 tgc ctg tgt tat gtg ctc atc att gcc aag atg cgc atg gtg gcc ctc      1190
Cys Leu Cys Tyr Val Leu Ile Ile Ala Lys Met Arg Met Val Ala Leu
240                 245                 250                 255 aag gct ggc tgg cag cag cgc aag cgc tca gag cgc aag atc act cta      1238
Lys Ala Gly Trp Gln Gln Arg Lys Arg Ser Glu Arg Lys Ile Thr Leu
                260                 265                 270 atg gtg atg atg gtg gtg atg gtt ttt gtc atc tgc tgg atg cct ttc      1286
Met Val Met Met Val Val Met Val Phe Val Ile Cys Trp Met Pro Phe
            275                 280                 285 tac gtg gta cag ctg gtc aac gtg ttc gcc gag caa gac gac gcc acc      1334
Tyr Val Val Gln Leu Val Asn Val Phe Ala Glu Gln Asp Asp Ala Thr
        290                 295                 300 gtg agc cag ttg tct gtc atc ctg ggc tat gcc aac agc tgt gcc aac      1382
Val Ser Gln Leu Ser Val Ile Leu Gly Tyr Ala Asn Ser Cys Ala Asn
    305                 310                 315 ccc atc ctc tac ggc ttc ctg tcg gac aac ttc aag cgc tct ttc cag      1430
Pro Ile Leu Tyr Gly Phe Leu Ser Asp Asn Phe Lys Arg Ser Phe Gln
320                 325                 330                 335 cgc atc ctg tgc ctc agc tgg atg gat aac gct gcg gag gaa cca gtc      1478
Arg Ile Leu Cys Leu Ser Trp Met Asp Asn Ala Ala Glu Glu Pro Val
                340                 345                 350 gac tac tat gcc act gcc ctg aag agt cga gcc tac agc gtg gag gac      1526
Asp Tyr Tyr Ala Thr Ala Leu Lys Ser Arg Ala Tyr Ser Val Glu Asp
            355                 360                 365 ttc cag ccc gag aat ctg gag tct gga ggc gtt ttc cgt aat ggc acc      1574
Phe Gln Pro Glu Asn Leu Glu Ser Gly Gly Val Phe Arg Asn Gly Thr
        370                 375                 380 tgc gct tcc agg atc agc acg ctt tga ggccgggcac tgccggagg             1621
Cys Ala Ser Arg Ile Ser Thr Leu
    385                 390 gggggagtgg tcagaaagat ggagctggga agcgggtggg agggaatggt aacccgacac    1681
caggtgctga agtcatagtg catgacacg atgcagcgcc cctgcgctga acctgttcc      1741 gctgcgcagg tcagcgggcc agactctttt cagagtggct acaagacagt ccctaatcac   1801
```

```
cgctctcctt tcgcagagcc ttactgtcaa ggaagcacag ctcgaggatg tctaggcaac    1861
ttgtcttttc tactctcaga gaaggaaggc acattttccc ttgggccctt cctctgctcc    1921
actccatccc gagcagagct aggcgcttaa gaaaaagttc tgtgccctga tctccagtct    1981
tggtatagta ccacacatat gcttctttgg agc                                 2014
```

<210> SEQ ID NO 4
<211> LENGTH: 391
<212> TYPE: PRT
<213> ORGANISM: Mus musculus

<400> SEQUENCE: 4

```
Met Phe Pro Asn Gly Thr Ala Ser Ser Pro Ser Ser Pro Ser Pro
1               5                   10                  15

Ser Pro Gly Ser Cys Gly Glu Gly Ala Cys Ser Arg Gly Pro Gly Ser
            20                  25                  30

Gly Ala Ala Asp Gly Met Glu Glu Pro Gly Arg Asn Ala Ser Gln Asn
            35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335
```

```
Ile Leu Cys Leu Ser Trp Met Asp Asn Ala Glu Glu Pro Val Asp
            340                 345                 350
Tyr Tyr Ala Thr Ala Leu Lys Ser Arg Ala Tyr Ser Val Glu Asp Phe
            355                 360                 365
Gln Pro Glu Asn Leu Glu Ser Gly Gly Val Phe Arg Asn Gly Thr Cys
370                 375                 380
Ala Ser Arg Ile Ser Thr Leu
385                 390

<210> SEQ ID NO 5
<211> LENGTH: 1769
<212> TYPE: DNA
<213> ORGANISM: Homo sapiens
<220> FEATURE:
<221> NAME/KEY: CDS
<222> LOCATION: (361)..(1470)

<400> SEQUENCE: 5
cgcagccacc catgcgcgcg cgctcgcaag accaccagcg cccagagccc cagtctgagg      60
cttggcgccg ggggtctgcg ggcgagggga gctctctacg tgcgaggggc tagcgggagc    120
cggcacaaga gggtcgagga ccaggaacc ccaaacgtcc ggcgccaggc gctagccaag     180
ctgctgcgcg ccccggcgcc cagctggctc ggggacagcc gctgggtgtc ggagaccgga    240
gctagcggat tgcagcggaa aagcaaagat gtcacactgg atccttggcc tccagggtcc    300
attaaggtga gaataagatc tctgggctgg ctggaactag cctaagactg aaaagcagcc    360 atg gac atg gcg gat gag cca ctc aat gga agc cac aca tgg cta tcc       408
Met Asp Met Ala Asp Glu Pro Leu Asn Gly Ser His Thr Trp Leu Ser
1                 5                   10                  15 att cca ttt gac ctc aat ggc tct gtg gtg tca acc aac acc tca aac       456
Ile Pro Phe Asp Leu Asn Gly Ser Val Val Ser Thr Asn Thr Ser Asn
                20                  25                  30 cag aca gag ccg tac tat gac ctg aca agc aat gca gtc ctc aca ttc       504
Gln Thr Glu Pro Tyr Tyr Asp Leu Thr Ser Asn Ala Val Leu Thr Phe
            35                  40                  45 atc tat ttt gtg gtc tgc atc att ggg ttg tgt ggc aac aca ctt gtc       552
Ile Tyr Phe Val Val Cys Ile Ile Gly Leu Cys Gly Asn Thr Leu Val
        50                  55                  60 att tat gtc atc ctc cgc tat gcc aag atg aag acc atc acc aac att       600
Ile Tyr Val Ile Leu Arg Tyr Ala Lys Met Lys Thr Ile Thr Asn Ile
65                  70                  75                  80 tac atc ctc aac ctg gcc atc gca gat gag ctc ttc atg ctg ggt ctg       648
Tyr Ile Leu Asn Leu Ala Ile Ala Asp Glu Leu Phe Met Leu Gly Leu
                85                  90                  95 cct ttc ttg gct atg cag gtg gct ctg gtc cac tgg ccc ttt ggc aag       696
Pro Phe Leu Ala Met Gln Val Ala Leu Val His Trp Pro Phe Gly Lys
            100                 105                 110 gcc att tgc cgg gtg gtc atg act gtg gat ggc atc aat cag ttc acc       744
Ala Ile Cys Arg Val Val Met Thr Val Asp Gly Ile Asn Gln Phe Thr
        115                 120                 125 agc atc ttc tgc ctg aca gtc atg agc atc gac cga tac ctg gct gtg       792
Ser Ile Phe Cys Leu Thr Val Met Ser Ile Asp Arg Tyr Leu Ala Val
    130                 135                 140 gtc cac ccc atc aag tcg gcc aag tgg agg aga ccc cgg acg gcc aag       840
Val His Pro Ile Lys Ser Ala Lys Trp Arg Arg Pro Arg Thr Ala Lys
145                 150                 155                 160 atg atc acc atg gct gtg tgg gga gtc tct ctg ctg gtc atc ttg ccc       888
Met Ile Thr Met Ala Val Trp Gly Val Ser Leu Leu Val Ile Leu Pro
                165                 170                 175
```

| | | | | | | | | | | | | | | | |
|---|---|---|---|---|---|---|---|---|---|---|---|---|---|---|---|
| atc | atg | ata | tat | gct | ggg | ctc | cgg | agc | aac | cag | tgg | ggg | aga | agc | agc | 936 |
| Ile | Met | Ile | Tyr | Ala | Gly | Leu | Arg | Ser | Asn | Gln | Trp | Gly | Arg | Ser | Ser | |
| | | | 180 | | | | | 185 | | | | | 190 | | | |

```
atc atg ata tat gct ggg ctc cgg agc aac cag tgg ggg aga agc agc      936
Ile Met Ile Tyr Ala Gly Leu Arg Ser Asn Gln Trp Gly Arg Ser Ser
            180                 185                 190 tgc acc atc aac tgg cca ggt gaa tct ggg gct tgg tac aca ggg ttc      984
Cys Thr Ile Asn Trp Pro Gly Glu Ser Gly Ala Trp Tyr Thr Gly Phe
        195                 200                 205 atc atc tac act ttc att ctg ggg ttc ctg gta ccc ctc acc atc atc     1032
Ile Ile Tyr Thr Phe Ile Leu Gly Phe Leu Val Pro Leu Thr Ile Ile
    210                 215                 220 tgt ctt tgc tac ctg ttc att atc atc aag gtg aag tcc tct gga atc     1080
Cys Leu Cys Tyr Leu Phe Ile Ile Ile Lys Val Lys Ser Ser Gly Ile
225                 230                 235                 240 cga gtg ggc tcc tct aag agg aag aag tct gag aag aag gtc acc cga     1128
Arg Val Gly Ser Ser Lys Arg Lys Lys Ser Glu Lys Lys Val Thr Arg
                245                 250                 255 atg gtg tcc atc gtg gtg gct gtc ttc atc ttc tgc tgg ctt ccc ttc     1176
Met Val Ser Ile Val Val Ala Val Phe Ile Phe Cys Trp Leu Pro Phe
            260                 265                 270 tac ata ttc aac gtt tct tcc gtc tcc atg gcc atc agc ccc acc cca     1224
Tyr Ile Phe Asn Val Ser Ser Val Ser Met Ala Ile Ser Pro Thr Pro
        275                 280                 285 gcc ctt aaa ggc atg ttt gac ttt gtg gtg gtc ctc acc tat gct aac     1272
Ala Leu Lys Gly Met Phe Asp Phe Val Val Val Leu Thr Tyr Ala Asn
    290                 295                 300 agc tgt gcc aac cct atc cta tat gcc ttc ttg tct gac aac ttc aag     1320
Ser Cys Ala Asn Pro Ile Leu Tyr Ala Phe Leu Ser Asp Asn Phe Lys
305                 310                 315                 320 aag agc ttc cag aat gtc ctc tgc ttg gtc aag gtg agc ggc aca gat     1368
Lys Ser Phe Gln Asn Val Leu Cys Leu Val Lys Val Ser Gly Thr Asp
                325                 330                 335 gat ggg gag cgg agt gac agt aag cag gac aaa tcc cgg ctg aat gag     1416
Asp Gly Glu Arg Ser Asp Ser Lys Gln Asp Lys Ser Arg Leu Asn Glu
            340                 345                 350 acc acg gag acc cag agg acc ctc ctc aat gga gac ctc caa acc agt     1464
Thr Thr Glu Thr Gln Arg Thr Leu Leu Asn Gly Asp Leu Gln Thr Ser
        355                 360                 365 atc tga actgcttggg gggtgggaaa gaaccaagcc atgctctgtc tactggcaat     1520
Ile gggctcccta cccacactgg cttcctgcct cccaccctc acacctggct tctagaatag      1580
aggattgctc agcatgagtc cagttcagag aacggtgttt gagtcagctt gtctgattga     1640
atgataatgt gctaaattga ttacctcccc cttaaagcga acactgaaat gcaggtagac     1700
aattcaaagt ctggagaaga gggatcatgc ctggatatga tctttagaaa caacaaaaaa     1760
aaaaaaaaa                                                             1769
```

<210> SEQ ID NO 6
<211> LENGTH: 369
<212> TYPE: PRT
<213> ORGANISM: Homo sapiens

<400> SEQUENCE: 6

```
Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
            20                  25                  30

Gln Thr Glu Pro Tyr Tyr Asp Leu Thr Ser Asn Ala Val Leu Thr Phe
        35                  40                  45
```

```
Ile Tyr Phe Val Val Cys Ile Ile Gly Leu Cys Gly Asn Thr Leu Val
     50                  55                  60
Ile Tyr Val Ile Leu Arg Tyr Ala Lys Met Lys Thr Ile Thr Asn Ile
 65                  70                  75                  80
Tyr Ile Leu Asn Leu Ala Ile Ala Asp Glu Leu Phe Met Leu Gly Leu
                 85                  90                  95
Pro Phe Leu Ala Met Gln Val Ala Leu Val His Trp Pro Phe Gly Lys
            100                 105                 110
Ala Ile Cys Arg Val Val Met Thr Val Asp Gly Ile Asn Gln Phe Thr
        115                 120                 125
Ser Ile Phe Cys Leu Thr Val Met Ser Ile Asp Arg Tyr Leu Ala Val
130                 135                 140
Val His Pro Ile Lys Ser Ala Lys Trp Arg Arg Pro Arg Thr Ala Lys
145                 150                 155                 160
Met Ile Thr Met Ala Val Trp Gly Val Ser Leu Leu Val Ile Leu Pro
                165                 170                 175
Ile Met Ile Tyr Ala Gly Leu Arg Ser Asn Gln Trp Gly Arg Ser Ser
            180                 185                 190
Cys Thr Ile Asn Trp Pro Gly Glu Ser Gly Ala Trp Tyr Thr Gly Phe
        195                 200                 205
Ile Ile Tyr Thr Phe Ile Leu Gly Phe Leu Val Pro Leu Thr Ile Ile
210                 215                 220
Cys Leu Cys Tyr Leu Phe Ile Ile Lys Val Lys Ser Ser Gly Ile
225                 230                 235                 240
Arg Val Gly Ser Ser Lys Arg Lys Ser Glu Lys Lys Val Thr Arg
                245                 250                 255
Met Val Ser Ile Val Val Ala Val Phe Ile Phe Cys Trp Leu Pro Phe
            260                 265                 270
Tyr Ile Phe Asn Val Ser Ser Val Ser Met Ala Ile Ser Pro Thr Pro
        275                 280                 285
Ala Leu Lys Gly Met Phe Asp Phe Val Val Leu Thr Tyr Ala Asn
290                 295                 300
Ser Cys Ala Asn Pro Ile Leu Tyr Ala Phe Leu Ser Asp Asn Phe Lys
305                 310                 315                 320
Lys Ser Phe Gln Asn Val Leu Cys Leu Val Lys Val Ser Gly Thr Asp
                325                 330                 335
Asp Gly Glu Arg Ser Asp Ser Lys Gln Asp Lys Ser Arg Leu Asn Glu
            340                 345                 350
Thr Thr Glu Thr Gln Arg Thr Leu Leu Asn Gly Asp Leu Gln Thr Ser
        355                 360                 365
Ile

<210> SEQ ID NO 7
<211> LENGTH: 1110
<212> TYPE: DNA
<213> ORGANISM: Mus musculus
<220> FEATURE:
<221> NAME/KEY: CDS
<222> LOCATION: (1)..(1110)

<400> SEQUENCE: 7 atg gag atg agc tct gag cag ttg aat ggg agc caa gta tgg gtg tcc    48
Met Glu Met Ser Ser Glu Gln Leu Asn Gly Ser Gln Val Trp Val Ser
 1               5                  10                  15 tct cca ttt gac ctc aac ggc tca ctg ggg cca agc aat ggc tcc aac    96
Ser Pro Phe Asp Leu Asn Gly Ser Leu Gly Pro Ser Asn Gly Ser Asn
```

```
                  20                  25                  30
cag acc gag cca tac tac gac atg aca agc aac gcc gtc ctc acg ttc       144
Gln Thr Glu Pro Tyr Tyr Asp Met Thr Ser Asn Ala Val Leu Thr Phe
         35                  40                  45 atc tac ttc gtg gtg tgt gtt gtc ggg ctg tgc ggc aac acg ctg gtc       192
Ile Tyr Phe Val Val Cys Val Val Gly Leu Cys Gly Asn Thr Leu Val
 50                  55                  60 att tat gtc atc ctc cgc tat gcc aag atg aag acc atc acc aac atc       240
Ile Tyr Val Ile Leu Arg Tyr Ala Lys Met Lys Thr Ile Thr Asn Ile
 65                  70                  75                  80 tac atc ctt aac ctg gcc att gca gat gaa ctc ttc atg cta ggg ctg       288
Tyr Ile Leu Asn Leu Ala Ile Ala Asp Glu Leu Phe Met Leu Gly Leu
             85                  90                  95 ccc ttc ttg gcc atg cag gtg gcg cta gtc cac tgg cct ttt ggc aag       336
Pro Phe Leu Ala Met Gln Val Ala Leu Val His Trp Pro Phe Gly Lys
        100                 105                 110 gcc atc tgc cgg gtg gtc atg act gta gat ggc atc aat cag ttc acc       384
Ala Ile Cys Arg Val Val Met Thr Val Asp Gly Ile Asn Gln Phe Thr
        115                 120                 125 agt atc ttc tgc ttg acg gtc atg agc atc gac cgc tac ctg gcc gtg       432
Ser Ile Phe Cys Leu Thr Val Met Ser Ile Asp Arg Tyr Leu Ala Val
130                 135                 140 gtg cac ccc att aag tca gcc aaa tgg agg cga ccc cgg aca gcc aag       480
Val His Pro Ile Lys Ser Ala Lys Trp Arg Arg Pro Arg Thr Ala Lys
145                 150                 155                 160 atg atc aat gta gct gtg tgg tgt gtg tct ctc ctc gtc att ttg ccc       528
Met Ile Asn Val Ala Val Trp Cys Val Ser Leu Leu Val Ile Leu Pro
                165                 170                 175 atc atg ata tac gcc ggc ctc cgg agc aac cag tgg ggc agg agc agc       576
Ile Met Ile Tyr Ala Gly Leu Arg Ser Asn Gln Trp Gly Arg Ser Ser
        180                 185                 190 tgt acc atc aac tgg cca ggc gaa tcc ggg gcg tgg tac aca ggt ttc       624
Cys Thr Ile Asn Trp Pro Gly Glu Ser Gly Ala Trp Tyr Thr Gly Phe
        195                 200                 205 att atc tac gcc ttc atc ctg ggg ttc ctg gta ccc ctt acc atc att       672
Ile Ile Tyr Ala Phe Ile Leu Gly Phe Leu Val Pro Leu Thr Ile Ile
210                 215                 220 tgt ctc tgc tac ctg ttc atc atc atc aag gtg aag tcc tct gga atc       720
Cys Leu Cys Tyr Leu Phe Ile Ile Ile Lys Val Lys Ser Ser Gly Ile
225                 230                 235                 240 cga gtg gga tca tcc aag agg aaa aag tca gag aaa aag gtg acc cgc       768
Arg Val Gly Ser Ser Lys Arg Lys Lys Ser Glu Lys Lys Val Thr Arg
                245                 250                 255 atg gtg tcc atc gta gtg gct gtc ttc atc ttc tgc tgg ctc ccc ttc       816
Met Val Ser Ile Val Val Ala Val Phe Ile Phe Cys Trp Leu Pro Phe
        260                 265                 270 tac atc ttc aac gtc tct tcc gtg tct gtg gcc atc agt ccc acc cca       864
Tyr Ile Phe Asn Val Ser Ser Val Ser Val Ala Ile Ser Pro Thr Pro
        275                 280                 285 gcc ctg aaa ggc atg ttt gac ttt gtg gtg atc ctc acc tat gcc aac       912
Ala Leu Lys Gly Met Phe Asp Phe Val Val Ile Leu Thr Tyr Ala Asn
        290                 295                 300 agc tgc gcc aac ccc atc ctg tac gcc ttc ttg tct gac aac ttc aag       960
Ser Cys Ala Asn Pro Ile Leu Tyr Ala Phe Leu Ser Asp Asn Phe Lys
305                 310                 315                 320 aag agc ttc cag aat gtt ctt tgc ttg gtc aag gtg agt ggt acg gag      1008
Lys Ser Phe Gln Asn Val Leu Cys Leu Val Lys Val Ser Gly Thr Glu
                325                 330                 335 gat ggg gag agg agc gac agt aag cag gac aaa tcc cgg ctg aat gag      1056
```

```
Asp Gly Glu Arg Ser Asp Ser Lys Gln Asp Lys Ser Arg Leu Asn Glu
                340                 345                 350 acc acg gag acc cag agg acc ctc ctc aat gga gac ctc caa acc agt     1104
Thr Thr Glu Thr Gln Arg Thr Leu Leu Asn Gly Asp Leu Gln Thr Ser
                355                 360                 365 atc tga                                                             1110
Ile
```

<210> SEQ ID NO 8
<211> LENGTH: 369
<212> TYPE: PRT
<213> ORGANISM: Mus musculus

<400> SEQUENCE: 8

```
Met Glu Met Ser Ser Glu Gln Leu Asn Gly Ser Gln Val Trp Val Ser
1               5                   10                  15

Ser Pro Phe Asp Leu Asn Gly Ser Leu Gly Pro Ser Asn Gly Ser Asn
                20                  25                  30

Gln Thr Glu Pro Tyr Tyr Asp Met Thr Ser Asn Ala Val Leu Thr Phe
            35                  40                  45

Ile Tyr Phe Val Val Cys Val Val Gly Leu Cys Gly Asn Thr Leu Val
50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
130                 135                 140

Val His Pro Ile Lys Ser Ala Lys Trp Arg Arg Pro Arg Thr Ala Lys
145                 150                 155                 160

Met Ile Asn Val Ala Val Trp Cys Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Ala Phe Ile Leu Gly Phe Leu Val Pro Leu Thr Ile Ile
210                 215                 220

Cys Leu Cys Tyr Leu Phe Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Val Ala Ile Ser Pro Thr Pro
        275                 280                 285

Ala Leu Lys Gly Met Phe Asp Phe Val Val Ile Leu Thr Tyr Ala Asn
        290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Glu
```

|  | 325 |  |  |  | 330 |  |  |  | 335 |  |  |
|---|---|---|---|---|---|---|---|---|---|---|---|
| Asp | Gly | Glu | Arg | Ser | Asp | Ser | Lys | Gln | Asp | Lys | Ser | Arg | Leu | Asn | Glu |
|  |  |  | 340 |  |  |  |  | 345 |  |  |  | 350 |

| Thr | Thr | Glu | Thr | Gln | Arg | Thr | Leu | Leu | Asn | Gly | Asp | Leu | Gln | Thr | Ser |
|---|---|---|---|---|---|---|---|---|---|---|---|---|---|---|---|
|  |  | 355 |  |  |  |  | 360 |  |  |  |  | 365 |

Ile

<210> SEQ ID NO 9
<211> LENGTH: 4730
<212> TYPE: DNA
<213> ORGANISM: Mus musculus
<220> FEATURE:
<221> NAME/KEY: CDS
<222> LOCATION: (2091)..(3200)

<400> SEQUENCE: 9

```
ggtaccagcc accagcttcg acccactgag catcagctgg gacatggtga aaatcacaga      60
agacttgggg ccagctggtt ctcgtccaag tgctcactcc accaagcact ttaactctct     120
aagcctcagt ttccactgag ggaggacgga atcctcacct cctggggaca atggggacaa     180
tgggtgtgac tagactccat ccggtttttt attttattta tttatttatt tatttatctg     240
tttatttatt tatttatttc gtgtatgtga gtacaccatt gttctcttca tacataccag     300
aagaggcacc ggatcccatt acaaatggtt gtgagccacc atgtggttgc tgggaattga     360
actcaggacc tctaaaagag tagtcagagc tcttaaccat ctctccagcc caagaaacac     420
tttaattctt gatagataaa taataaata aataaataaa taaaagcatc tttgacattc     480
atgaaaagcc tacatccctc ccctagttcc ctgggttttt tttttttttt tttttttttg     540
tcctaagtca gagaactgca ggcaaaaggt ctttaggaga gagccttccc aagcagagat     600
ggagtggaga atggagaaca ttgatgttac aaaatcagaa ccaggaggag agaagagaa     660
agagggggaa gagaagaggg aggaagagga gaggcctaa agcatcatta aaaaaaaaa     720
aagccagact cttacttttta atattgaaga ctataacttg attcactgtg taggcaggct     780
tcaataaatt agagataatg agacagtaga cgggggagg taacgtttat gaggctctga     840
ttataagcct gcacaatgct aggatttgca cacactttct cttgtttaac cttcatgaca     900
cccctgtgtt gacaaaggag agttacagca gttaagggct gggcatgggg tcacgtgggg     960
ctcaactctg gagccaaagt ttgttctccc tttaacttct tgagttttcc caccacgggg    1020
gcggggtat ctctgatggt ggcagacatc aagccagcat agagttgttc ttggggtccc    1080
caaatgctgg tgtcagactc ctccagggac aggggttgaa accctccaag atctgccttt    1140
ttccagtctg gatcggtcaa ttccttaggg gtcaaagtct atgtgtttga agccatagcc    1200
gtctgccaca tgtgtgtcat ctaggatgat ggtttaactc aaacccttcc cccaccattg    1260
aaaaaaagac ctcaaaaagt cttcaggctg acaggtgggc tggcagctag acagaaaaaa    1320
aaaaaaagaa aacttgcttt tcaattgaaa aatgcataga aggggaacaa gggattggta    1380
gctcactgtg actccaaaca gcagaggccc aggcatggga gtgctacgca tgaaagtcag    1440
ctaaggctac atagtgagct ccaggctagc tcagctcaag gaagaaggag gaggggaaag    1500
ggaggaggga gagaggggag gaggaggagg aagaagagag gaggaagaag aaggaagaga    1560
gggagtgatg tgggagggaa agaaaagaag gaaggaggga ggaagagggg gagatggctc    1620
cgtcaataaa gcacctgact tgcaagcaag aagacctgag ttcaacctcc agaaccacat    1680
aaaactgccg gtatatttga tacatatctg taatcacagc cgtgggggag gcagacacag    1740
```

```
gtggatctct gcagctcact gaacagctag cccaagctac atggtgaaac atcatgactc    1800
aaaaaagggt gaggctatca aacctatgta aacacacaca cacaaacaca cacatacacc    1860
atgcagcagc acacatgaat acatgaaaaa aaaagaggaa ttggggggc atggaacgtg     1920 aaactaagaa gatgaacaag aaacagaggg agcctaagta gcctgggact gacggctact    1980
ttttctgctt cttttcccag atgtcacagt agactcttgg cccccagagc cctgtgaggc    2040
gagaggaaga tctctaggca gcttggttct agacggagtg gaaagcagcc atg gag       2096
                                                        Met Glu
                                                          1 atg agc tct gag cag ttg aat ggg agc caa gta tgg gtg tcc tct cca     2144
Met Ser Ser Glu Gln Leu Asn Gly Ser Gln Val Trp Val Ser Ser Pro
        5                   10                  15 ttt gac ctc aac ggc tca ctg ggg cca agc aat ggc tcc aac cag acc     2192
Phe Asp Leu Asn Gly Ser Leu Gly Pro Ser Asn Gly Ser Asn Gln Thr
 20                  25                  30 gag cca tac tac gac atg aca agc aac gcc gtc ctc acg ttc atc tac     2240
Glu Pro Tyr Tyr Asp Met Thr Ser Asn Ala Val Leu Thr Phe Ile Tyr
 35                  40                  45                  50 ttc gtg gtg tgt gtt gtc ggg ctg tgc ggc aac acg ctg gtc att tat     2288
Phe Val Val Cys Val Val Gly Leu Cys Gly Asn Thr Leu Val Ile Tyr
                 55                  60                  65 gtc atc ctc cgc tat gcc aag atg aag acc atc acc aac atc tac atc     2336
Val Ile Leu Arg Tyr Ala Lys Met Lys Thr Ile Thr Asn Ile Tyr Ile
         70                  75                  80 ctt aac ctg gcc att gca gat gaa ctc ttc atg cta ggg ctg ccc ttc     2384
Leu Asn Leu Ala Ile Ala Asp Glu Leu Phe Met Leu Gly Leu Pro Phe
             85                  90                  95 ttg gcc atg cag gtg gcg cta gtc cac tgg cct ttt ggc aag gcc atc     2432
Leu Ala Met Gln Val Ala Leu Val His Trp Pro Phe Gly Lys Ala Ile
100                 105                 110 tgc cgg gtg gtc atg act gta gat ggc atc aat cag ttc acc agt atc     2480
Cys Arg Val Val Met Thr Val Asp Gly Ile Asn Gln Phe Thr Ser Ile
115                 120                 125                 130 ttc tgc ttg acg gtc atg agc atc gac cgc tac ctg gcc gtg gtg cac     2528
Phe Cys Leu Thr Val Met Ser Ile Asp Arg Tyr Leu Ala Val Val His
                135                 140                 145 ccc att aag tca gcc aaa tgg agg cga ccc cgg aca gcc aag atg atc     2576
Pro Ile Lys Ser Ala Lys Trp Arg Arg Pro Arg Thr Ala Lys Met Ile
            150                 155                 160 aat gta gct gtg tgg tgt gtg tct ctc gtc att ttg ccc atc atg         2624
Asn Val Ala Val Trp Cys Val Ser Leu Leu Val Ile Leu Pro Ile Met
                165                 170                 175 ata tac gcc ggc ctc cgg agc aac cag tgg ggc agg agc agc tgt acc     2672
Ile Tyr Ala Gly Leu Arg Ser Asn Gln Trp Gly Arg Ser Ser Cys Thr
180                 185                 190 atc aac tgg cca ggc gaa tcc ggg gcg tgg tac aca ggt ttc att atc     2720
Ile Asn Trp Pro Gly Glu Ser Gly Ala Trp Tyr Thr Gly Phe Ile Ile
195                 200                 205                 210 tac gcc ttc atc ctg ggg ttc ctg gta ccc ctt acc atc att tgt ctc     2768
Tyr Ala Phe Ile Leu Gly Phe Leu Val Pro Leu Thr Ile Ile Cys Leu
                215                 220                 225 tgc tac ctg ttc atc atc atc aag gtg aag tcc tct gga atc cga gtg    2816
Cys Tyr Leu Phe Ile Ile Ile Lys Val Lys Ser Ser Gly Ile Arg Val
                230                 235                 240 gga tca tcc aag agg aaa aag tca gag aaa aag gtg acc cgc atg gtg    2864
Gly Ser Ser Lys Arg Lys Lys Ser Glu Lys Lys Val Thr Arg Met Val
                245                 250                 255 tcc atc gta gtg gct gtc ttc atc ttc tgc tgg ctc ccc ttc tac atc    2912
```

```
Ser Ile Val Val Ala Val Phe Ile Phe Cys Trp Leu Pro Phe Tyr Ile
    260                 265                 270 ttc aac gtc tct tcc gtg tct gtg gcc atc agt ccc acc cca gcc ctg   2960
Phe Asn Val Ser Ser Val Ser Val Ala Ile Ser Pro Thr Pro Ala Leu
275                 280                 285                 290 aaa ggc atg ttt gac ttt gtg gtg atc ctc acc tat gcc aac agc tgc   3008
Lys Gly Met Phe Asp Phe Val Val Ile Leu Thr Tyr Ala Asn Ser Cys
                295                 300                 305 gcc aac ccc atc ctg tac gcc ttc ttg tct gac aac ttc aag aag agc   3056
Ala Asn Pro Ile Leu Tyr Ala Phe Leu Ser Asp Asn Phe Lys Lys Ser
            310                 315                 320 ttc cag aat gtt ctt tgc ttg gtc aag gtg agt ggt acg gag gat ggg   3104
Phe Gln Asn Val Leu Cys Leu Val Lys Val Ser Gly Thr Glu Asp Gly
        325                 330                 335 gag agg agc gac agt aag cag gac aaa tcc cgg ctg aat gag acc acg   3152
Glu Arg Ser Asp Ser Lys Gln Asp Lys Ser Arg Leu Asn Glu Thr Thr
    340                 345                 350 gag acc cag agg acc ctc ctc aat gga gac ctc caa acc agt atc tga   3200
Glu Thr Gln Arg Thr Leu Leu Asn Gly Asp Leu Gln Thr Ser Ile
355                 360                 365 acaacccagg aacgcaacat gcacacacac tagccaagcc ctgactcctg tcagtgtgtc   3260
tcccattccc tggcttcccg cctcccctat ccatcacacc cggcttctag aacagagctg   3320
tgttctacac gcgccccgtt cagagaacag gatttgagtc tggcttgtcc gaaagtatac   3380
ccctctggtc acgtctcccc taaagtgaac gttttcgtgc aggcagacaa ttcacaatcc   3440
ggagcggaag acatcattgc ctgggtgtga cctggtggaa acagctgcc cggcagaaac   3500 cggaaaaacc aaaactaaat caaagtcctg tgtgtatgtg tgctaacacg ttacgtaaat   3560
cttgtgatct gatatttaca tttgtatatt ctccctccc cggtcacaca acatgtccc   3620 gtgtttgtaa gcccaagtag ctagttcgtg tgcgtctagt ataggtggac agttaccaca   3680
acgctgaacc tgaagaaaag gactcgccac gtcacagtca gtccaatcta agcttccagc   3740
atctgtcttg catgggccat ccccagacac tggaggagca tgagcagtat gtatgttcat   3800
aggataatat aataatatgt tcgtagaata atataataat atgttttgt aaaaaaaaaa   3860 ttgaaagtaa ggtggttttg tattctttat cctagagggc ccctgtcata tatatggtcc   3920
tagcctcgca ggcgctgcac ctgcgccagg aagggtattt catcaatttc aaacatgtga   3980
agttggagta agaagagaca gtgagaatat tctgtgagag tcagaatgta aactcgggtt   4040
tgaatgtaac tctcagatac gatcagttat tcatttaccc aaaaggactt taagggttgt   4100
ggccatagag catgccattt atcaggacga agcctgcttt gagatcagat tatagatttc   4160
tctcctcaaa ttcctttcgc ttcggaaacc attggggaag ggaggggtca ggagcctgag   4220
aggcaaaaac cagactatga ttcccatggg gaaacaaatt ttctcctcaa cacatacctg   4280
tgcctgtgtg agttcataca cacacacaca cacacacaca cacacacaca cacacacaca   4340
caaataataa tgaaaagaaa aaagaagtag aattatgcct ttaagggcaa ccatgaagtt   4400
gtcttgtttt taatgccagg taggatttct taatgaaaga aaacagaact gtaattccac   4460
aactccttaa aggtgctttg ggttggcttg tccttggttg gtttgttctt ggggacaggt   4520
ggttgttgtt tcttcctgtc ttatgtgtat gcagtgggta tgtgtgttta tgcctctgtg   4580
tgtgtgtgtg tgcgctcgtg tacttatgtg tgtgcaggct ggaggctgat actgctacct   4640
ccctacatca ttgactaact ttactgagac agggtctctt gctgaacgtg aagccttctg   4700
gtcaagtgag ccggcttgcc tcgaggatcc                                   4730
```

```
<210> SEQ ID NO 10
<211> LENGTH: 369
<212> TYPE: PRT
<213> ORGANISM: Mus musculus

<400> SEQUENCE: 10

Met Glu Met Ser Ser Glu Gln Leu Asn Gly Ser Gln Val Trp Val Ser
1               5                   10                  15

Ser Pro Phe Asp Leu Asn Gly Ser Leu Gly Pro Ser Asn Gly Ser Asn
            20                  25                  30

Gln Thr Glu Pro Tyr Tyr Asp Met Thr Ser Asn Ala Val Leu Thr Phe
        35                  40                  45

Ile Tyr Phe Val Val Cys Val Val Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160

Met Ile Asn Val Ala Val Trp Cys Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Ala Phe Ile Leu Gly Phe Leu Val Pro Leu Thr Ile Ile
    210                 215                 220

Cys Leu Cys Tyr Leu Phe Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Val Ala Ile Ser Pro Thr Pro
        275                 280                 285

Ala Leu Lys Gly Met Phe Asp Phe Val Val Ile Leu Thr Tyr Ala Asn
    290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Glu
                325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Ser
        355                 360                 365

Ile
```

```
<210> SEQ ID NO 11
<211> LENGTH: 1266
<212> TYPE: DNA
<213> ORGANISM: Homo sapiens
<220> FEATURE:
<221> NAME/KEY: CDS
<222> LOCATION: (10)..(1266)

<400> SEQUENCE: 11 gcccttacc atg gac atg ctt cat cca tca tcg gtg tcc acg acc tca gaa      51
          Met Asp Met Leu His Pro Ser Ser Val Ser Thr Thr Ser Glu
          1               5                  10 cct gag aat gcc tcc tcg gcc tgg ccc cca gat gcc acc ctg ggc aac        99
Pro Glu Asn Ala Ser Ser Ala Trp Pro Pro Asp Ala Thr Leu Gly Asn
15                  20                  25                  30 gtg tcg gca ggc cca agc ccg gca ggg ctg gcc gtc agt ggc gtt ctg       147
Val Ser Ala Gly Pro Ser Pro Ala Gly Leu Ala Val Ser Gly Val Leu
                35                  40                  45 atc ccc ctg gtc tac ctg gtg gtg tgc gtg gtg ggc ctg ctg ggt aac       195
Ile Pro Leu Val Tyr Leu Val Val Cys Val Val Gly Leu Leu Gly Asn
            50                  55                  60 tcg ctg gtc atc tat gtg gtc ctg cgg cac acg gcc agc cct tca gtc       243
Ser Leu Val Ile Tyr Val Val Leu Arg His Thr Ala Ser Pro Ser Val
        65                  70                  75 acc aac gtc tac atc ctc aac ctg gcg ctg gcc gac gag ctc ttc atg       291
Thr Asn Val Tyr Ile Leu Asn Leu Ala Leu Ala Asp Glu Leu Phe Met
80                  85                  90 ctg ggg ctg ccc ttc ctg gcc gcc cag aac gcc ctg tcc tac tgg ccc       339
Leu Gly Leu Pro Phe Leu Ala Ala Gln Asn Ala Leu Ser Tyr Trp Pro
95                  100                 105                 110 ttc ggc tcc ctc atg tgc cgc ctg gtc atg gcg gtg gat ggc atc aac       387
Phe Gly Ser Leu Met Cys Arg Leu Val Met Ala Val Asp Gly Ile Asn
                115                 120                 125 cag ttc acc agc ata ttc tgc ctg act gtc atg agc gtg gac cgc tac       435
Gln Phe Thr Ser Ile Phe Cys Leu Thr Val Met Ser Val Asp Arg Tyr
            130                 135                 140 ctg gcc gtg gta cat ccc acc cgc tca gcc cgc tgg cgc aca gct ccg       483
Leu Ala Val Val His Pro Thr Arg Ser Ala Arg Trp Arg Thr Ala Pro
        145                 150                 155 gtg gcc cgc acg gtc agc gcg gct gtg tgg gtg gcc tca gcc gtg gtg       531
Val Ala Arg Thr Val Ser Ala Ala Val Trp Val Ala Ser Ala Val Val
160                 165                 170 gtg ctg ccc gtg gtg gtc ttc tcg gga gtg ccc cgc ggc atg agc acc       579
Val Leu Pro Val Val Val Phe Ser Gly Val Pro Arg Gly Met Ser Thr
175                 180                 185                 190 tgc cac atg cag tgg ccc gag ccg gcg gcg gcc tgg cga gcc ggc ttc       627
Cys His Met Gln Trp Pro Glu Pro Ala Ala Ala Trp Arg Ala Gly Phe
                195                 200                 205 atc atc tac acg gcc gca ctg ggc ttc ttc ggg ccg ctg ctg gtc atc       675
Ile Ile Tyr Thr Ala Ala Leu Gly Phe Phe Gly Pro Leu Leu Val Ile
            210                 215                 220 tgc ctc tgc tac ctg ctc atc gtg gtg aag gtg cgc tca gct ggg cgc       723
Cys Leu Cys Tyr Leu Leu Ile Val Val Lys Val Arg Ser Ala Gly Arg
        225                 230                 235 cgg gtg tgg gca ccc tcg tgc cag cgg cgg cgc gcc tcc gaa cgc agg       771
Arg Val Trp Ala Pro Ser Cys Gln Arg Arg Arg Ala Ser Glu Arg Arg
240                 245                 250 gtc acg cgc atg gtg gtg gcc gtg gtg gca ctc ttc gtg ctc tgc tgg       819
Val Thr Arg Met Val Val Ala Val Val Ala Leu Phe Val Leu Cys Trp
255                 260                 265                 270
```

| | | | | | | | | | | | | | | | | |
|---|---|---|---|---|---|---|---|---|---|---|---|---|---|---|---|---|
| atg | ccc | ttc | tat | gtg | ctc | aac | atc | gtc | aac | gtg | gtg | tgc | cca | ctg | ccc | 867 |
| Met | Pro | Phe | Tyr | Val | Leu | Asn | Ile | Val | Asn | Val | Val | Cys | Pro | Leu | Pro | |
| | | | | 275 | | | | 280 | | | | | | 285 | | |
| gag | gag | cct | gcc | ttc | ttt | ggg | ctc | tac | ttc | ctg | gtg | gtg | gcg | ctg | ccc | 915 |
| Glu | Glu | Pro | Ala | Phe | Phe | Gly | Leu | Tyr | Phe | Leu | Val | Val | Ala | Leu | Pro | |
| | | | 290 | | | | | 295 | | | | | 300 | | | |
| tat | gcc | aac | agc | tgt | gcc | aac | ccc | atc | ctt | tat | ggc | ttc | ctc | tcc | tac | 963 |
| Tyr | Ala | Asn | Ser | Cys | Ala | Asn | Pro | Ile | Leu | Tyr | Gly | Phe | Leu | Ser | Tyr | |
| | | | 305 | | | | | 310 | | | | | 315 | | | |
| cgc | ttc | aag | cag | ggc | ttc | cgc | agg | gtc | ctg | ctg | cgg | ccc | tcc | cgc | cgt | 1011 |
| Arg | Phe | Lys | Gln | Gly | Phe | Arg | Arg | Val | Leu | Leu | Arg | Pro | Ser | Arg | Arg | |
| | | 320 | | | | | 325 | | | | | 330 | | | | |
| gtg | cgc | agc | cag | gag | ccc | act | gtg | ggg | ccc | ccg | gag | aag | act | gag | gag | 1059 |
| Val | Arg | Ser | Gln | Glu | Pro | Thr | Val | Gly | Pro | Pro | Glu | Lys | Thr | Glu | Glu | |
| 335 | | | | | 340 | | | | | 345 | | | | | 350 | |
| gag | gat | gag | gag | gag | gag | gat | ggg | gag | gag | agc | agg | gag | ggg | ggc | aag | 1107 |
| Glu | Asp | Glu | Glu | Glu | Glu | Asp | Gly | Glu | Glu | Ser | Arg | Glu | Gly | Gly | Lys | |
| | | | | 355 | | | | | 360 | | | | | 365 | | |
| ggg | aag | gag | atg | aac | ggc | cgg | gtc | agc | cag | atc | acg | cag | cct | ggc | acc | 1155 |
| Gly | Lys | Glu | Met | Asn | Gly | Arg | Val | Ser | Gln | Ile | Thr | Gln | Pro | Gly | Thr | |
| | | | 370 | | | | | 375 | | | | | 380 | | | |
| agc | ggg | cag | gag | cgg | ccg | ccc | agc | aga | gtg | gcc | agc | aag | gag | cag | cag | 1203 |
| Ser | Gly | Gln | Glu | Arg | Pro | Pro | Ser | Arg | Val | Ala | Ser | Lys | Glu | Gln | Gln | |
| | 385 | | | | | 390 | | | | | 395 | | | | | |
| ctc | cta | ccc | caa | gag | gct | tcc | act | ggg | gag | aag | tcc | agc | acg | atg | cgc | 1251 |
| Leu | Leu | Pro | Gln | Glu | Ala | Ser | Thr | Gly | Glu | Lys | Ser | Ser | Thr | Met | Arg | |
| | 400 | | | | | 405 | | | | | 410 | | | | | |
| atc | agc | tac | ctg | tag | | | | | | | | | | | | 1266 |
| Ile | Ser | Tyr | Leu | | | | | | | | | | | | | |
| 415 | | | | | | | | | | | | | | | | |

```
<210> SEQ ID NO 12
<211> LENGTH: 418
<212> TYPE: PRT
<213> ORGANISM: Homo sapiens

<400> SEQUENCE: 12
```

Met Asp Met Leu His Pro Ser Val Ser Thr Thr Ser Glu Pro Glu
1               5                   10                  15

Asn Ala Ser Ser Ala Trp Pro Pro Asp Ala Thr Leu Gly Asn Val Ser
                20                  25                  30

Ala Gly Pro Ser Pro Ala Gly Leu Ala Val Ser Gly Val Leu Ile Pro
            35                  40                  45

Leu Val Tyr Leu Val Val Cys Val Val Gly Leu Leu Gly Asn Ser Leu
        50                  55                  60

Val Ile Tyr Val Val Leu Arg His Thr Ala Ser Pro Ser Val Thr Asn
65                  70                  75                  80

Val Tyr Ile Leu Asn Leu Ala Leu Ala Asp Glu Leu Phe Met Leu Gly
                85                  90                  95

Leu Pro Phe Leu Ala Ala Gln Asn Ala Leu Ser Tyr Trp Pro Phe Gly
            100                 105                 110

Ser Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
    130                 135                 140

Val Val His Pro Thr Arg Ser Ala Arg Trp Arg Thr Ala Pro Val Ala
145                 150                 155                 160

Arg Thr Val Ser Ala Ala Val Trp Val Ala Ser Ala Val Val Val Leu

```
            165                 170                 175
Pro Val Val Phe Ser Gly Val Pro Arg Gly Met Ser Thr Cys His
        180                 185                 190

Met Gln Trp Pro Glu Pro Ala Ala Trp Arg Ala Gly Phe Ile Ile
        195                 200                 205

Tyr Thr Ala Ala Leu Gly Phe Phe Gly Pro Leu Leu Val Ile Cys Leu
    210                 215                 220

Cys Tyr Leu Leu Ile Val Val Lys Val Arg Ser Ala Gly Arg Arg Val
225                 230                 235                 240

Trp Ala Pro Ser Cys Gln Arg Arg Arg Ser Glu Arg Arg Val Thr
                245                 250                 255

Arg Met Val Val Ala Val Ala Leu Phe Val Leu Cys Trp Met Pro
        260                 265                 270

Phe Tyr Val Leu Asn Ile Val Asn Val Val Cys Pro Leu Pro Glu Glu
    275                 280                 285

Pro Ala Phe Phe Gly Leu Tyr Phe Leu Val Val Ala Leu Pro Tyr Ala
    290                 295                 300

Asn Ser Cys Ala Asn Pro Ile Leu Tyr Gly Phe Leu Ser Tyr Arg Phe
305                 310                 315                 320

Lys Gln Gly Phe Arg Arg Val Leu Leu Arg Pro Ser Arg Arg Val Arg
                325                 330                 335

Ser Gln Glu Pro Thr Val Gly Pro Pro Glu Lys Thr Glu Glu Asp
        340                 345                 350

Glu Glu Glu Glu Asp Gly Glu Glu Ser Arg Glu Gly Gly Lys Gly Lys
                355                 360                 365

Glu Met Asn Gly Arg Val Ser Gln Ile Thr Gln Pro Gly Thr Ser Gly
        370                 375                 380

Gln Glu Arg Pro Pro Ser Arg Val Ala Ser Lys Glu Gln Gln Leu Leu
385                 390                 395                 400

Pro Gln Glu Ala Ser Thr Gly Glu Lys Ser Ser Thr Met Arg Ile Ser
                405                 410                 415

Tyr Leu

<210> SEQ ID NO 13
<211> LENGTH: 1383
<212> TYPE: DNA
<213> ORGANISM: Mus musculus
<220> FEATURE:
<221> NAME/KEY: CDS
<222> LOCATION: (41)..(1327)

<400> SEQUENCE: 13
gttagggctg gttggctgct gactgatcct catctcagcc atg gcc act gtt acc      55
                                            Met Ala Thr Val Thr
                                            1               5 tat ccc tca tcc gag cct atg acc ttg gac cct ggg aac aca tcc tcg     103
Tyr Pro Ser Ser Glu Pro Met Thr Leu Asp Pro Gly Asn Thr Ser Ser
            10                  15                  20 acc tgg ccc ctg gat acc acc ctg ggg aac aca tcc gct ggc gct agc     151
Thr Trp Pro Leu Asp Thr Thr Leu Gly Asn Thr Ser Ala Gly Ala Ser
        25                  30                  35 ctg aca ggc ctg gct gtc agt ggc atc ttg atc tct ctg gtg tac ctg     199
Leu Thr Gly Leu Ala Val Ser Gly Ile Leu Ile Ser Leu Val Tyr Leu
    40                  45                  50 gtg gtg tgc gtg gtg ggt ctg ctg ggc aac tcg ctg gtg atc tac gtg     247
Val Val Cys Val Val Gly Leu Leu Gly Asn Ser Leu Val Ile Tyr Val
55                  60                  65
```

-continued

| | | |
|---|---|---|
| gtc ctg cgg cac acg tcc agc cca tca gtg acc agt gtc tat atc ctc<br>Val Leu Arg His Thr Ser Ser Pro Ser Val Thr Ser Val Tyr Ile Leu<br>70                          75                          80                         85 | 295 |
| aac ctg gct ctg gct gat gag ctc ttc atg cta ggg cta ccc ttc ctg<br>Asn Leu Ala Leu Ala Asp Glu Leu Phe Met Leu Gly Leu Pro Phe Leu<br>                          90                        95                        100 | 343 |
| gct gct cag aac gcc ctg tcc tac tgg ccc ttt gga tct ctc atg tgc<br>Ala Ala Gln Asn Ala Leu Ser Tyr Trp Pro Phe Gly Ser Leu Met Cys<br>                    105                        110                       115 | 391 |
| cgt ctg gtc atg gcc gtg gat ggc atc aac cag ttc acc agc atc ttc<br>Arg Leu Val Met Ala Val Asp Gly Ile Asn Gln Phe Thr Ser Ile Phe<br>         120                     125                       130 | 439 |
| tgc ctc acc gtc atg agt gtg gac cgc tat ctg gct gtg gtg cac ccc<br>Cys Leu Thr Val Met Ser Val Asp Arg Tyr Leu Ala Val Val His Pro<br>135                        140                        145 | 487 |
| aca cgc tca gcc cgc tgg cgc acg gca cca gtg gct cgc acg gtc agt<br>Thr Arg Ser Ala Arg Trp Arg Thr Ala Pro Val Ala Arg Thr Val Ser<br>150                        155                        160                       165 | 535 |
| gca gct gtc tgg gtg gcc tcg gct gtg gtg gtg ctg cct gtg gtt gtg<br>Ala Ala Val Trp Val Ala Ser Ala Val Val Val Leu Pro Val Val Val<br>                    170                        175                       180 | 583 |
| ttc tca gga gtg ccc cgg ggc atg agc acg tgc cac atg cag tgg cca<br>Phe Ser Gly Val Pro Arg Gly Met Ser Thr Cys His Met Gln Trp Pro<br>                    185                        190                       195 | 631 |
| gag cca gcg gct gcc tgg cga aca gcc ttc atc atc tac acg gcc gca<br>Glu Pro Ala Ala Ala Trp Arg Thr Ala Phe Ile Ile Tyr Thr Ala Ala<br>         200                     205                       210 | 679 |
| ctg ggc ttc ttt ggg ccc ctg ctg gtc atc tgc ttg tgc tac ttg ctc<br>Leu Gly Phe Phe Gly Pro Leu Leu Val Ile Cys Leu Cys Tyr Leu Leu<br>      215                        220                       225 | 727 |
| att gtg gta aag gtg cgg tcg acc acc cgg cgg gtg cgg gcg ccc tcg<br>Ile Val Val Lys Val Arg Ser Thr Thr Arg Arg Val Arg Ala Pro Ser<br>230                        235                        240                       245 | 775 |
| tgt cag tgg gta cag gca ccc gca tgc cag cgg cga cgc cgc tct gag<br>Cys Gln Trp Val Gln Ala Pro Ala Cys Gln Arg Arg Arg Arg Ser Glu<br>                    250                        255                       260 | 823 |
| cgc agg gtc aca cgc atg gtg gtg gcc gtg gtg gca ctc ttc gtc ctc<br>Arg Arg Val Thr Arg Met Val Val Ala Val Val Ala Leu Phe Val Leu<br>         265                     270                       275 | 871 |
| tgc tgg atg cct ttc tat ctg ctc aac atc gtc aat gtg gtg tgc ccg<br>Cys Trp Met Pro Phe Tyr Leu Leu Asn Ile Val Asn Val Val Cys Pro<br>                    280                        285                       290 | 919 |
| ctg ccg gag gag ccc gcc ttc ttc ggc ctc tac ttc ctg gtg gtg gcg<br>Leu Pro Glu Glu Pro Ala Phe Phe Gly Leu Tyr Phe Leu Val Val Ala<br>      295                        300                       305 | 967 |
| ctg ccc tac gcc aac agc tgc gca aac ccc atc ctc tac ggc ttc ctc<br>Leu Pro Tyr Ala Asn Ser Cys Ala Asn Pro Ile Leu Tyr Gly Phe Leu<br>310                        315                        320                       325 | 1015 |
| tcc tac cgc ttc aag cag ggc ttt cgc agg atc ctg cta aga cca tca<br>Ser Tyr Arg Phe Lys Gln Gly Phe Arg Arg Ile Leu Leu Arg Pro Ser<br>                          330                        335                       340 | 1063 |
| cgt cgc att cgg agc cag gag cca ggg tcg gga cct cca gag aag act<br>Arg Arg Ile Arg Ser Gln Glu Pro Gly Ser Gly Pro Pro Glu Lys Thr<br>         345                     350                       355 | 1111 |
| gaa gag gag gag gat gaa gaa gaa gaa gag aga agg gaa gag gag gag<br>Glu Glu Glu Glu Asp Glu Glu Glu Glu Arg Arg Glu Glu Glu Glu<br>                       360                       365                       370 | 1159 |
| cgg agg atg cag aga ggg cag gag atg aac ggg agg ctc agt cag atc<br>Arg Arg Met Gln Arg Gly Gln Glu Met Asn Gly Arg Leu Ser Gln Ile | 1207 |

```
                    375                 380                 385
gca cag gct ggc act agt gga caa cag cca cgg ccc tgc aca ggg act      1255
Ala Gln Ala Gly Thr Ser Gly Gln Gln Pro Arg Pro Cys Thr Gly Thr
390                 395                 400                 405 gct aag gag cag cag ctt ctg ccc cag gag gcc aca gct ggg gac aag      1303
Ala Lys Glu Gln Gln Leu Leu Pro Gln Glu Ala Thr Ala Gly Asp Lys
                410                 415                 420 gcc agc aca ctg agc cat ctg taa ggaccttcaa agaaccagcg tggttcagaa     1357
Ala Ser Thr Leu Ser His Leu
                425 aagagcagaa gctgggcttg acctcg                                         1383

<210> SEQ ID NO 14
<211> LENGTH: 428
<212> TYPE: PRT
<213> ORGANISM: Mus musculus

<400> SEQUENCE: 14

Met Ala Thr Val Thr Tyr Pro Ser Ser Glu Pro Met Thr Leu Asp Pro
1               5                   10                  15

Gly Asn Thr Ser Ser Thr Trp Pro Leu Asp Thr Thr Leu Gly Asn Thr
            20                  25                  30

Ser Ala Gly Ala Ser Leu Thr Gly Leu Ala Val Ser Gly Ile Leu Ile
        35                  40                  45

Ser Leu Val Tyr Leu Val Val Cys Val Val Gly Leu Leu Gly Asn Ser
    50                  55                  60

Leu Val Ile Tyr Val Val Leu Arg His Thr Ser Ser Pro Ser Val Thr
65                  70                  75                  80

Ser Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
            100                 105                 110

Gly Ser Leu Met Cys Arg Leu Val Met Ala Val Asp Gly Ile Asn Gln
        115                 120                 125

Phe Thr Ser Ile Phe Cys Leu Thr Val Met Ser Val Asp Arg Tyr Leu
    130                 135                 140

Ala Val Val His Pro Thr Arg Ser Ala Arg Trp Arg Thr Ala Pro Val
145                 150                 155                 160

Ala Arg Thr Val Ser Ala Ala Val Trp Val Ala Ser Ala Val Val Val
                165                 170                 175

Leu Pro Val Val Phe Ser Gly Val Pro Arg Gly Met Ser Thr Cys
            180                 185                 190

His Met Gln Trp Pro Glu Pro Ala Ala Ala Trp Arg Thr Ala Phe Ile
        195                 200                 205

Ile Tyr Thr Ala Ala Leu Gly Phe Phe Gly Pro Leu Leu Val Ile Cys
    210                 215                 220

Leu Cys Tyr Leu Leu Ile Val Val Lys Val Arg Ser Thr Thr Arg Arg
225                 230                 235                 240

Val Arg Ala Pro Ser Cys Gln Trp Val Gln Ala Pro Ala Cys Gln Arg
                245                 250                 255

Arg Arg Arg Ser Glu Arg Arg Val Thr Arg Met Val Val Ala Val Val
            260                 265                 270

Ala Leu Phe Val Leu Cys Trp Met Pro Phe Tyr Leu Leu Asn Ile Val
        275                 280                 285

Asn Val Val Cys Pro Leu Pro Glu Glu Pro Ala Phe Phe Gly Leu Tyr
```

```
                    290                 295                 300

Phe Leu Val Val Ala Leu Pro Tyr Ala Asn Ser Cys Ala Asn Pro Ile
305                 310                 315                 320

Leu Tyr Gly Phe Leu Ser Tyr Arg Phe Lys Gln Gly Phe Arg Arg Ile
                325                 330                 335

Leu Leu Arg Pro Ser Arg Arg Ile Arg Ser Gln Glu Pro Gly Ser Gly
                340                 345                 350

Pro Pro Glu Lys Thr Glu Glu Glu Asp Glu Glu Glu Glu Glu Glu Arg
                355                 360                 365

Arg Glu Glu Glu Arg Arg Met Gln Arg Gly Gln Glu Met Asn Gly
                370                 375                 380

Arg Leu Ser Gln Ile Ala Gln Ala Gly Thr Ser Gly Gln Gln Pro Arg
385                 390                 395                 400

Pro Cys Thr Gly Thr Ala Lys Glu Gln Gln Leu Leu Pro Gln Glu Ala
                405                 410                 415

Thr Ala Gly Asp Lys Ala Ser Thr Leu Ser His Leu
                420                 425

<210> SEQ ID NO 15
<211> LENGTH: 1258
<212> TYPE: DNA
<213> ORGANISM: Homo sapiens
<220> FEATURE:
<221> NAME/KEY: CDS
<222> LOCATION: (65)..(1231)

<400> SEQUENCE: 15
ccgagctctc tggcgcagcg ctagctccgc cgcgctcagc tgccctgcgc cggcacccct    60 ggtc atg agc gcc ccc tcg acg ctg ccc ccc ggg ggc gag gaa ggg ctg    109
     Met Ser Ala Pro Ser Thr Leu Pro Pro Gly Gly Glu Glu Gly Leu
     1               5                   10                  15 ggg acg gcc tgg ccc tct gca gcc aat gcc agt agc gct ccg gcg gag    157
Gly Thr Ala Trp Pro Ser Ala Ala Asn Ala Ser Ser Ala Pro Ala Glu
                20                  25                  30 gcg gag gag gcg gtg gcg ggg ccc ggg gac gcg cgg gcg gcg ggc atg    205
Ala Glu Glu Ala Val Ala Gly Pro Gly Asp Ala Arg Ala Ala Gly Met
            35                  40                  45 gtc gct atc cag tgc atc tac gcg ctg gtg tgc ctg gtg ggg ctg gtg    253
Val Ala Ile Gln Cys Ile Tyr Ala Leu Val Cys Leu Val Gly Leu Val
        50                  55                  60 ggc aac gcc ctg gtc atc ttc gtg atc ctt cgc tac gcc aag atg aag    301
Gly Asn Ala Leu Val Ile Phe Val Ile Leu Arg Tyr Ala Lys Met Lys
65                  70                  75 acg gct acc aac atc tac ctg ctc aac ctg gcc gta gcc gac gag ctc    349
Thr Ala Thr Asn Ile Tyr Leu Leu Asn Leu Ala Val Ala Asp Glu Leu
80                  85                  90                  95 ttc atg ctg agc gtg ccc ttc gtg gcc tcg tcg gcc gcc ctg cgc cac    397
Phe Met Leu Ser Val Pro Phe Val Ala Ser Ser Ala Ala Leu Arg His
                100                 105                 110 tgg ccc ttc ggc tcc gtg ctg tgc cgc gcg gtg ctc agc gtc gac ggc    445
Trp Pro Phe Gly Ser Val Leu Cys Arg Ala Val Leu Ser Val Asp Gly
            115                 120                 125 ctc aac atg ttc acc agc gtc ttc tgt ctc acc gtg ctc agc gtg gac    493
Leu Asn Met Phe Thr Ser Val Phe Cys Leu Thr Val Leu Ser Val Asp
        130                 135                 140 cgc tac gtg gcc gtg gtg cac cct ctg cgc gcg gcg acc tac cgg cgg    541
Arg Tyr Val Ala Val Val His Pro Leu Arg Ala Ala Thr Tyr Arg Arg
145                 150                 155
```

-continued

| | | |
|---|---|---|
| ccc agc gtg gcc aag ctc atc aac ctg ggc gtg tgg ctg gca tcc ctg<br>Pro Ser Val Ala Lys Leu Ile Asn Leu Gly Val Trp Leu Ala Ser Leu<br>160                    165                    170                    175 | 589 |
| ttg gtc act ctc ccc atc gcc atc ttc gca gac acc aga ccg gct cgc<br>Leu Val Thr Leu Pro Ile Ala Ile Phe Ala Asp Thr Arg Pro Ala Arg<br>                    180                    185                    190 | 637 |
| ggc ggc cag gcc gtg gcc tgc aac ctg cag tgg cca cac ccg gcc tgg<br>Gly Gly Gln Ala Val Ala Cys Asn Leu Gln Trp Pro His Pro Ala Trp<br>195                    200                    205 | 685 |
| tcg gca gtc ttc gtg gtc tac act ttc ctg ctg ggc ttc ctg ctg ccc<br>Ser Ala Val Phe Val Val Tyr Thr Phe Leu Leu Gly Phe Leu Leu Pro<br>210                    215                    220 | 733 |
| gtg ctg gcc att ggc ctg tgc tac ctg ctc atc gtg ggc aag atg cgc<br>Val Leu Ala Ile Gly Leu Cys Tyr Leu Leu Ile Val Gly Lys Met Arg<br>225                    230                    235 | 781 |
| gcc gtg gcc ctg cgc gct ggc tgg cag cag cgc agg cgc tcg gag aag<br>Ala Val Ala Leu Arg Ala Gly Trp Gln Gln Arg Arg Arg Ser Glu Lys<br>240                    245                    250                    255 | 829 |
| aaa atc acc agg ctg gtg ctg atg gtc gtg gtc gtc ttt gtg ctc tgc<br>Lys Ile Thr Arg Leu Val Leu Met Val Val Val Val Phe Val Leu Cys<br>                    260                    265                    270 | 877 |
| tgg atg cct ttc tac gtg gtg cag ctg ctg aac ctc ttc gtg acc agc<br>Trp Met Pro Phe Tyr Val Val Gln Leu Leu Asn Leu Phe Val Thr Ser<br>275                    280                    285 | 925 |
| ctt gat gcc acc gtc aac cac gtg tcc ctt atc ctt agc tat gcc aac<br>Leu Asp Ala Thr Val Asn His Val Ser Leu Ile Leu Ser Tyr Ala Asn<br>                    290                    295                    300 | 973 |
| agc tgc gcc aac ccc att ctc tat ggc ttc ctc tcc gac aac ttc cgc<br>Ser Cys Ala Asn Pro Ile Leu Tyr Gly Phe Leu Ser Asp Asn Phe Arg<br>305                    310                    315 | 1021 |
| cga ttc ttc cag cgg gtt ctc tgc ctg cgc tgc tgc ctc ctg gaa ggt<br>Arg Phe Phe Gln Arg Val Leu Cys Leu Arg Cys Cys Leu Leu Glu Gly<br>320                    325                    330                    335 | 1069 |
| gct gga ggt gct gag gag gag ccc ctg gac tac tat gcc act gct ctc<br>Ala Gly Gly Ala Glu Glu Glu Pro Leu Asp Tyr Tyr Ala Thr Ala Leu<br>                    340                    345                    350 | 1117 |
| aag agc aaa ggt ggg gca ggg tgc atg tgc ccc cca ctc ccc tgc cag<br>Lys Ser Lys Gly Gly Ala Gly Cys Met Cys Pro Pro Leu Pro Cys Gln<br>355                    360                    365 | 1165 |
| cag gaa gcc ctg caa cca gaa ccc ggc cgc aag cgc atc ccc ctc acc<br>Gln Glu Ala Leu Gln Pro Glu Pro Gly Arg Lys Arg Ile Pro Leu Thr<br>                    370                    375                    380 | 1213 |
| agg acc acc acc ttc tga ggagcccttc ccctacccac cctgcgt<br>Arg Thr Thr Thr Phe<br>385 | 1258 |

<210> SEQ ID NO 16
<211> LENGTH: 388
<212> TYPE: PRT
<213> ORGANISM: Homo sapiens

<400> SEQUENCE: 16

Met Ser Ala Pro Ser Thr Leu Pro Pro Gly Gly Glu Glu Gly Leu Gly
1                  5                    10                    15

Thr Ala Trp Pro Ser Ala Ala Asn Ala Ser Ser Ala Pro Ala Glu Ala
                    20                    25                    30

Glu Glu Ala Val Ala Gly Pro Gly Asp Ala Arg Ala Ala Gly Met Val
                35                    40                    45

Ala Ile Gln Cys Ile Tyr Ala Leu Val Cys Leu Val Gly Leu Val Gly
50                    55                    60

```
Asn Ala Leu Val Ile Phe Val Ile Leu Arg Tyr Ala Lys Met Lys Thr
 65                  70                  75                  80

Ala Thr Asn Ile Tyr Leu Leu Asn Leu Ala Val Ala Asp Glu Leu Phe
                 85                  90                  95

Met Leu Ser Val Pro Phe Val Ala Ser Ser Ala Leu Arg His Trp
            100                 105                 110

Pro Phe Gly Ser Val Leu Cys Arg Ala Val Leu Ser Val Asp Gly Leu
            115                 120                 125

Asn Met Phe Thr Ser Val Phe Cys Leu Thr Val Leu Ser Val Asp Arg
130                 135                 140

Tyr Val Ala Val Val His Pro Leu Arg Ala Ala Thr Tyr Arg Arg Pro
145                 150                 155                 160

Ser Val Ala Lys Leu Ile Asn Leu Gly Val Trp Leu Ala Ser Leu Leu
                165                 170                 175

Val Thr Leu Pro Ile Ala Ile Phe Ala Asp Thr Arg Pro Ala Arg Gly
            180                 185                 190

Gly Gln Ala Val Ala Cys Asn Leu Gln Trp Pro His Pro Ala Trp Ser
            195                 200                 205

Ala Val Phe Val Val Tyr Thr Phe Leu Leu Gly Phe Leu Leu Pro Val
210                 215                 220

Leu Ala Ile Gly Leu Cys Tyr Leu Leu Ile Val Gly Lys Met Arg Ala
225                 230                 235                 240

Val Ala Leu Arg Ala Gly Trp Gln Gln Arg Arg Arg Ser Glu Lys Lys
                245                 250                 255

Ile Thr Arg Leu Val Leu Met Val Val Val Phe Val Leu Cys Trp
            260                 265                 270

Met Pro Phe Tyr Val Val Gln Leu Leu Asn Leu Phe Val Thr Ser Leu
            275                 280                 285

Asp Ala Thr Val Asn His Val Ser Leu Ile Leu Ser Tyr Ala Asn Ser
290                 295                 300

Cys Ala Asn Pro Ile Leu Tyr Gly Phe Leu Ser Asp Asn Phe Arg Arg
305                 310                 315                 320

Phe Phe Gln Arg Val Leu Cys Leu Arg Cys Cys Leu Leu Glu Gly Ala
                325                 330                 335

Gly Gly Ala Glu Glu Glu Pro Leu Asp Tyr Tyr Ala Thr Ala Leu Lys
            340                 345                 350

Ser Lys Gly Gly Ala Gly Cys Met Cys Pro Pro Leu Pro Cys Gln Gln
            355                 360                 365

Glu Ala Leu Gln Pro Glu Pro Gly Arg Lys Arg Ile Pro Leu Thr Arg
370                 375                 380

Thr Thr Thr Phe
385

<210> SEQ ID NO 17
<211> LENGTH: 1898
<212> TYPE: DNA
<213> ORGANISM: Mus musculus
<220> FEATURE:
<221> NAME/KEY: CDS
<222> LOCATION: (86)..(1240)

<400> SEQUENCE: 17
gaccccagcc cagcctcttg gtccttggct cacggtccgc tgctctccac gcattccgct    60
gctccggggt gggctacccc gagac atg aac gcg cca gca act ctg ctc cgg   112
                              Met Asn Ala Pro Ala Thr Leu Leu Arg
```

```
                       1                   5
ggg gtc gag gac acc acc tgg acc cct ggg atc aac gcc agc tgg gct      160
Gly Val Glu Asp Thr Thr Trp Thr Pro Gly Ile Asn Ala Ser Trp Ala
 10              15                  20                  25 ccg gag cag gag gag gat gcg atg ggg tcc gac ggc aca ggg aca gcg      208
Pro Glu Gln Glu Glu Asp Ala Met Gly Ser Asp Gly Thr Gly Thr Ala
                 30                  35                  40 ggc atg gtc act atc cag tgc atc tat gcg ctc gtg tgt ctg gtg ggc      256
Gly Met Val Thr Ile Gln Cys Ile Tyr Ala Leu Val Cys Leu Val Gly
                     45                  50                  55 ctg gtg gga aac gcc ctg gtc atc ttc gtg atc cta cgc tat gcc aag      304
Leu Val Gly Asn Ala Leu Val Ile Phe Val Ile Leu Arg Tyr Ala Lys
                 60                  65                  70 atg aag aca gcc acc aac atc tac cta ctc aac ctg gcc gtc gcc gat      352
Met Lys Thr Ala Thr Asn Ile Tyr Leu Leu Asn Leu Ala Val Ala Asp
 75                  80                  85 gag ctc ttc atg ctc agc gtg cca ttc gtg cgc tcg gcg gct gcc ctg      400
Glu Leu Phe Met Leu Ser Val Pro Phe Val Arg Ser Ala Ala Ala Leu
 90              95                 100                 105 cgc cac tgg ccg ttc ggg gcg gtg ctg tgt cgc gca gtg ctt agc gtg      448
Arg His Trp Pro Phe Gly Ala Val Leu Cys Arg Ala Val Leu Ser Val
                    110                 115                 120 gac ggc ctg aac atg ttc act agt gtc ttc tgc ctc acc gtg ctc agc      496
Asp Gly Leu Asn Met Phe Thr Ser Val Phe Cys Leu Thr Val Leu Ser
                125                 130                 135 gtg gac cgc tat gtg gct gtt gtg cac cct ctg cgc acc gcc acc tac      544
Val Asp Arg Tyr Val Ala Val Val His Pro Leu Arg Thr Ala Thr Tyr
                140                 145                 150 cgg cgg ccc agc gtg gcc aag cta atc aac ctg gga gtg tgg cta gca      592
Arg Arg Pro Ser Val Ala Lys Leu Ile Asn Leu Gly Val Trp Leu Ala
    155                 160                 165 tcc ttg ctg gtc acc ctg ccc atc gca gtc ttc gct gac acc agg cca      640
Ser Leu Leu Val Thr Leu Pro Ile Ala Val Phe Ala Asp Thr Arg Pro
170                 175                 180                 185 gct cgt ggg ggt gag gcc gtg gct tgc aac ctg cac tgg cct cac ccg      688
Ala Arg Gly Gly Glu Ala Val Ala Cys Asn Leu His Trp Pro His Pro
                    190                 195                 200 gcc tgg tct gcg gtc ttt gtg atc tat act ttt ttg ttg ggc ttc cta      736
Ala Trp Ser Ala Val Phe Val Ile Tyr Thr Phe Leu Leu Gly Phe Leu
                205                 210                 215 ccc ccg gtt ctg gcc atc gga tta tgc tac ctg ctt att gtg ggc aag      784
Pro Pro Val Leu Ala Ile Gly Leu Cys Tyr Leu Leu Ile Val Gly Lys
                220                 225                 230 atg cgc gct gtg gcc ctg cgc ggt ggc tgg caa caa cgg agg cgc tca      832
Met Arg Ala Val Ala Leu Arg Gly Gly Trp Gln Gln Arg Arg Arg Ser
235                 240                 245 gag aag aag atc act agg ctc gtg cta atg gtg gtg acc gtc ttt gtg      880
Glu Lys Lys Ile Thr Arg Leu Val Leu Met Val Val Thr Val Phe Val
250                 255                 260                 265 cta tgc tgg atg cct ttc tat gtg gtg cag ctt ctg aac ctg ttt gtc      928
Leu Cys Trp Met Pro Phe Tyr Val Val Gln Leu Leu Asn Leu Phe Val
                270                 275                 280 acc agc ctc gat gcc act gtc aac cat gtg tcc ctc atc ctg agc tat      976
Thr Ser Leu Asp Ala Thr Val Asn His Val Ser Leu Ile Leu Ser Tyr
                285                 290                 295 gcc aac agc tgt gcc aat ccc att ctc tat ggc ttc ctc tct gac aac     1024
Ala Asn Ser Cys Ala Asn Pro Ile Leu Tyr Gly Phe Leu Ser Asp Asn
                300                 305                 310 ttc cgg cgc tct ttc cag cgg gtt ctg tgc ctg cgc tgc tgt ctc ctg     1072
```

-continued

```
                Phe Arg Arg Ser Phe Gln Arg Val Leu Cys Leu Arg Cys Cys Leu Leu
                    315                 320                 325 gaa aca act gga ggt gct gag gaa gag ccc ctg gac tac tat gcc act          1120
Glu Thr Thr Gly Gly Ala Glu Glu Glu Pro Leu Asp Tyr Tyr Ala Thr
330                 335                 340                 345 gct ctc aaa agc aga ggg ggt gca gga tgc ata tgc cct cct ctg ccc          1168
Ala Leu Lys Ser Arg Gly Gly Ala Gly Cys Ile Cys Pro Pro Leu Pro
                350                 355                 360 tgc cag cag gag ccc gtg caa gca gaa cct ggc tgc aag caa gtc cct          1216
Cys Gln Gln Glu Pro Val Gln Ala Glu Pro Gly Cys Lys Gln Val Pro
            365                 370                 375 ttc acc aag acc act act ttc tga aaaccatttt accctccctc acctcgcctg         1270
Phe Thr Lys Thr Thr Thr Phe
            380 caaacgggtc tgcgccactc tctcaagcca gcaacttcaa gaacaactcc tgttttcact        1330 aagccaggcc ctttcagcag cctgtgtgct gtccccagga gcctcaggac tcctgctagt        1390 ccctccctct cctaggactg gctccaagga cacctccatg ggggtaggac tgccctggga        1450 tttgggctaa agtaccatcc attcctgggc tctggcaatt ttttcaagag gtgggaagca       1510 ggtggtggtc agaaaggaat gtctacccctt gtgtgacttg tgacagtgac tgcttgaaag       1570 agcccttggg aggctgaggt aggcagagct gtgctctgtg taggctcttt gctgtatggt       1630 agcatagtgt gtatggtgag acaagggaga agataggata actccaagtg gtttccctct       1690 gtgtcggtct gaggctctcg ttgctaagtg agatgtctac gtaacagacg aagggcactt       1750 gcactgtcac tgtacaagtg ttttccagtt gtcaaggggc cagtagagac ttcctgtgag       1810 tgtgaaaggc ttaaagaagc atgatgtggg gcggttttttg caaggcataa aacttctggt      1870 caggaattca aaggcagaag gattaaaa                                           1898
```

<210> SEQ ID NO 18
<211> LENGTH: 384
<212> TYPE: PRT
<213> ORGANISM: Mus musculus

<400> SEQUENCE: 18

```
Met Asn Ala Pro Ala Thr Leu Leu Arg Gly Val Glu Asp Thr Thr Trp
1               5                   10                  15

Thr Pro Gly Ile Asn Ala Ser Trp Ala Pro Glu Gln Glu Glu Asp Ala
            20                  25                  30

Met Gly Ser Asp Gly Thr Gly Thr Ala Gly Met Val Thr Ile Gln Cys
        35                  40                  45

Ile Tyr Ala Leu Val Cys Leu Val Gly Leu Val Gly Asn Ala Leu Val
    50                  55                  60

Ile Phe Val Ile Leu Arg Tyr Ala Lys Met Lys Thr Ala Thr Asn Ile
65                  70                  75                  80

Tyr Leu Leu Asn Leu Ala Val Ala Asp Glu Leu Phe Met Leu Ser Val
                85                  90                  95

Pro Phe Val Arg Ser Ala Ala Ala Leu Arg His Trp Pro Phe Gly Ala
            100                 105                 110

Val Leu Cys Arg Ala Val Leu Ser Val Asp Gly Leu Asn Met Phe Thr
        115                 120                 125

Ser Val Phe Cys Leu Thr Val Leu Ser Val Asp Arg Tyr Val Ala Val
    130                 135                 140

Val His Pro Leu Arg Thr Ala Thr Tyr Arg Arg Pro Ser Val Ala Lys
145                 150                 155                 160
```

| Leu | Ile | Asn | Leu | Gly | Val | Trp | Leu | Ala | Ser | Leu | Val | Thr | Leu | Pro |
| | | | | 165 | | | | | 170 | | | | | 175 |

| Ile | Ala | Val | Phe | Ala | Asp | Thr | Arg | Pro | Ala | Arg | Gly | Gly | Glu | Ala | Val |
| | | | 180 | | | | | 185 | | | | | 190 | | |

| Ala | Cys | Asn | Leu | His | Trp | Pro | His | Pro | Ala | Trp | Ser | Ala | Val | Phe | Val |
| | | | 195 | | | | | 200 | | | | | 205 | | |

| Ile | Tyr | Thr | Phe | Leu | Leu | Gly | Phe | Leu | Pro | Pro | Val | Leu | Ala | Ile | Gly |
| | 210 | | | | | 215 | | | | | 220 | | | | |

| Leu | Cys | Tyr | Leu | Leu | Ile | Val | Gly | Lys | Met | Arg | Ala | Val | Ala | Leu | Arg |
| 225 | | | | | 230 | | | | | 235 | | | | | 240 |

| Gly | Gly | Trp | Gln | Gln | Arg | Arg | Ser | Glu | Lys | Lys | Ile | Thr | Arg | Leu |
| | | | | 245 | | | | | 250 | | | | | 255 |

| Val | Leu | Met | Val | Val | Thr | Val | Phe | Val | Leu | Cys | Trp | Met | Pro | Phe | Tyr |
| | | | 260 | | | | | 265 | | | | | 270 | | |

| Val | Val | Gln | Leu | Leu | Asn | Leu | Phe | Val | Thr | Ser | Leu | Asp | Ala | Thr | Val |
| | | 275 | | | | | 280 | | | | | 285 | | | |

| Asn | His | Val | Ser | Leu | Ile | Leu | Ser | Tyr | Ala | Asn | Ser | Cys | Ala | Asn | Pro |
| | 290 | | | | | 295 | | | | | 300 | | | | |

| Ile | Leu | Tyr | Gly | Phe | Leu | Ser | Asp | Asn | Phe | Arg | Arg | Ser | Phe | Gln | Arg |
| 305 | | | | | 310 | | | | | 315 | | | | | 320 |

| Val | Leu | Cys | Leu | Arg | Cys | Cys | Leu | Leu | Glu | Thr | Thr | Gly | Gly | Ala | Glu |
| | | | | 325 | | | | | 330 | | | | | 335 | |

| Glu | Glu | Pro | Leu | Asp | Tyr | Tyr | Ala | Thr | Ala | Leu | Lys | Ser | Arg | Gly | Gly |
| | | | 340 | | | | | 345 | | | | | 350 | | |

| Ala | Gly | Cys | Ile | Cys | Pro | Pro | Leu | Pro | Cys | Gln | Gln | Glu | Pro | Val | Gln |
| | | 355 | | | | | 360 | | | | | 365 | | | |

| Ala | Glu | Pro | Gly | Cys | Lys | Gln | Val | Pro | Phe | Thr | Lys | Thr | Thr | Thr | Phe |
| 370 | | | | | 375 | | | | | 380 | | | | | |

<210> SEQ ID NO 19
<211> LENGTH: 10494
<212> TYPE: DNA
<213> ORGANISM: Homo sapiens
<220> FEATURE:
<221> NAME/KEY: CDS
<222> LOCATION: (7926)..(9020)

<400> SEQUENCE: 19

| ggccagggga | ctcctgccca | gaactcaggg | tggccgatgt | ggggaggggc | actgtggggc | 60 |
| cgacaggtcc | cctctctggc | catcaggccc | ccaggagggc | ccaggtgctt | ggaggtgggg | 120 |
| ggtgtcccag | cttgatgttg | gggatgtgag | tagatccagc | gcccacccac | ccgcagggct | 180 |
| gagctcccac | tgggcgctgg | gccgtgactc | gcacaccgga | ccctgcaccc | ctggggcacc | 240 |
| cagtgattcc | agaacagtgg | gaccccagag | gcttctcagg | gagccccaga | acatgacaga | 300 |
| tgggggccca | ggtgcgaggc | agtgggagct | ggaggaacac | agccaggggc | tgaggcgaga | 360 |
| accatgagga | tggtgggcag | aggctgaggg | gaggggcagc | agatggagat | ggggaggag | 420 |
| ttaggggtca | caaagggggt | tctcagagga | tctgccttgg | gaagccactg | ctgtgggagg | 480 |
| gtgggaggga | tacagcccag | gtacctccag | agaggatgga | aaggcttatg | gggcggattc | 540 |
| tgggcagggg | acctgggacc | agcctgcagc | ctcccctgag | ggcctggcca | tggccgcagg | 600 |
| ctggggagga | gggagggga | ccttggggcc | aggtgccatg | gtcctctaag | cactcttgct | 660 |
| cgatggtaaa | cataacacgc | gctgcttgca | gaacatgtgg | aaacactgaa | acgcttaaag | 720 |
| gagagaacat | ggtcccggta | cccggccttc | aagggagctg | ctggcgcctg | ttcaacagga | 780 |

```
gccgacccca cctgtgaaca gacggcaggc ggctgctccc atgtccctc  agagagggc     840 cctccgagtt ctgctgtcac ctggggcgc  ctcacttcat tcagccagtg gcggggctcc    900
ctgggtcggc acagagtcag ggagggggc  tgggggacct cctggtggga aaatgtccgg    960
tgatccccag cctccgcgct cagcgggagg aggcgctcgg tcccgcttct tacaaccagc   1020
ggcgctcacg gcgggcccgg ggatcagcat cccgggagct tctcaggaat gcagattccc   1080
aggccctcac tgcctgggga gtcggggcc  cagctcgagg cccaggaatc tgctttgagg   1140
acccaggtga ctctgctgcc tgcctgagaa ccccacctta ggtgagggac taaggtgtac   1200
ccatggattc atttcagggg aaataaaaag aacaacttag caggtagtct atgcttaaat   1260
atgtgtagga tccacaaata aggcatggat aaaacccgag tggagtgtcc tggaaatccc   1320
acgaccacgg acccccctcg ctggggctgc ctgccgcccc accagcctc  cacacaccca   1380 cttatctcca caaccccagc ccacccctca gagacgtctg cagagcccct gaccctctcc   1440
ccttgaacaa ggaccctcca ccctcttcag actctcgacg agggaccccc tggactcctg   1500
ctggcggcag gacccccacc ccaagctggg gtctaccaca gagcggacag caagaaaata   1560
gggtgggggc gcaggcgatc atggggtcac tgccagtggg accagggctg tgggcgagtg   1620
cgccagggtt cccggaggcc agacgtggga cccgggagtc gagcaggtga agcggccctg   1680
ccccgccccc accaggcact ggccccgccc ccgccccgcc ccgccccctc ccagccggcg   1740
cccgggagcc cggagccagt gccgcgcgga catcggggct cccccgttca gagggcgccg   1800
ccgcccaggt gagtgccgcc cgccccatgt ccccctcccg cgcgggcacc cctgcccctc   1860
ggctgttatc cccactgggg gtttcaccct gtgtgcgcag ccccggcccg gggtcccgcc   1920
gtgcgccccc agcccgctgc acgcactgtc ccccacgcgc cctccgcaca cccgcggggc   1980
tctcctgccg ccgccggggg tccctcсccct cccgttccat ccactcccag cagctccatc   2040
cctcccatct cctgccccca ccccacaact caccatctgc aggcaccccg tgtgccaggg   2100
tcagcccaga agccacaggg gacccagatg gccccactct gcccaccgcg ccgctcccgg   2160
cctctcctcc ccacgacggg ggccacagcg gggctggctc ctggagctgg aggagggtgg   2220
gtaaggctgg ggagggctcg gagcctgggg ctggggccg  gaagtggcac tcaggccaca   2280
gggaaccact gggccacgga aggagggtcc cagggtgccc gtggcaccca gcgaggggag   2340
gatccgcaat ttgggtgccg ggggaggcaa ctggtgcctg cgcgcagctg ggtcggtgag   2400
ctcctggaag gcagcaggca gaggccagca cccagggggcc ctgtgacctg gcactcacag   2460
atgggttccc tgaaacccaa gactggggag gctggggtgc caccccgccc gctgcgaaca   2520
gagccccctc ctgtccaagg caccgcgtgt acctggaatc ctcctggcgt cttcaccctc   2580
tccagaatag agaacacgcc actgggtgt  gtgcccttgg ccctcctccc ccaccccaga   2640
cccacccacg tgcccgaccc gctgtcccca gcctgccagc ctgcctgggg ccccctcaag   2700
ggcaagagag cggagtgcat ggtgacagaa gttggggatg gttccagtga ggctgagccc   2760
tttctgaagg cagtgattct ggactatgta ggtggggact gccagagcct cctgggcaga   2820
aactggtcaa cagcaccaag gacaggcgcc tggcgttgat ttccagagca agacccagcg   2880
aggctgtcag gaggtgcctg gtgtggaggg tgccccgaga agcgttcgcg gagcacgcgg   2940
gacccctgct gctgctgctc caggctggcc cacacctgcc tcagtttccc tctcctgggg   3000
agggtatgtg cccctggcca caggctgccg cagggacagg tggcgtgtat gtggggggaca   3060 ggcagggtg  ccattggctg cactcacaga gctggacccc aagggggcag tggcctgcca   3120
ccaggccacc cttacgacag aggaaacagg tcagaacgct tgtcctggga gcacaggcct   3180
```

```
ggctccgggg cctttggagg ggctggggcc tgtagtctta gctagggtgt ccccgacgt   3240 ttgcccctgc ccagcacaca atggaggagc ccgggtgggt ctgcagcctc tccagggtgc   3300
ggcgtgggcc ccggccgtgt gagccgctgc ctccccgagc agcaggttcc gcagcccctc   3360
caagctgcag ccgcatcgct gccccccatg aaggagccga ctccccgacc tcgtgctggg   3420
ttagcctgga aggagttggc agggtgcagg ctagacctcc acccagtcat ggaggacttg   3480
gtgctgaggc cccgcctctg gtcccaggcc cctgtgaaga ctgccccctt ctccgaggag   3540
cccagcggcc tcctggatgc tggggaaatg ctgggctgct tagggcagct tgtgggagca   3600
atcgttgagc gcccagtgta tgccagcccc gctgtggtcc ccgtcgtggg gaggtgaggc   3660
cgggagcggt gctgtgggca gactgggcc  atctgggtcc cctgtggctt ctgggctgac   3720
cctggcacac cggcacctg  cagatggtga gttgtgggt  gggggcagga gatggagggg   3780
atggatgctg ctgggagtgg atgcacgcag caccctgcac acagaagctc actcagtttc   3840
atcagctcag caaccctaca gtttgcagga gttgcctatc ccagaagctg ggctcagaga   3900
agcccgtgac ttaccccaga ccacgcagcc cgtgtgggga gtggtcaggg gccggggtct   3960
ctcccagtgc catgtcaggc tgagcagatc ccttcgtggc cgagggctcg ggatcagaaa   4020
gctcctactg ctggctcccc ctccagtgaa tcccccaccc acaagggaca gggccaccgg   4080
gacaattccc cgtgagtgcg taattttatg attcagagga tactgcttcc aaataacggc   4140
tcttgcagaa ttatgttcca agagtcaggt acagcaataa tggtctattt gtgtcctttg   4200
ctgctctgaa gtctaactcc ggaggtggag cactgggggc cgcagagccg ggacctggc   4260 agcctgtgga gcccctcgct gggctctggg catgggagtg gccttggagg aaccctgagg   4320
ctcctctgaa gctaagaagc tacaaagaca gggaggctga ggcaggagga tcacttgagc   4380
acaggtcgag gctgcagtga gctgtgatca cagcaccact tcgatccagc tcgggcaaca   4440
gagcaagacc ccatctcgaa aacaaaaaat caaacaggca tttgggaacc acacgtgctg   4500
gggacccagg gcctgtgttg gagatggacc ggagcccgac agccgccctc tccctgtccc   4560
accatcggtg gctcctctgt cccctccacc tggcctcctt gctacggagg aatgggccga   4620
aagtgcctcc ccagggaggg tgcagctcag aggcctctgc acctgggccg ccatcccacc   4680
cacctggact cccacgcagc ccgcgggctg tctccagacc actgtccttc cggaatgcat   4740
gctccacagg cagccagagg gagccgcaaa catggcgtgt tggatttcca tgctggtccc   4800
tggggagcgg agagccacag gcctcttccc ctccctctcc ctctccctcc ctccctctct   4860 cccctaccc  tgtctctctc tctcccccc  cactctctct ccctccctct ctcccccac   4920 cctgtctttc tctctcccctc cccacctccc cctctctctc cctcccccct ctcccctccc   4980
cctccctttc cctccctctc tccctctctc ctcgccgcct cccatccct  ctccctctct   5040 ctcctctctc tctcccctac cctgtctttc tctctgcctc ccgcctccc  cttccctctc   5100 cccccacctt ttctctctcc ctcccccacct cccctccct  ctccctcccc cctcacctcc   5160
cctccctttc cctccctctc tccctctctc tccccgcct cccatccct  ctccctctcc   5220 ctcctctctc tctcccccta ccctgttttc tctctccctc cccgcctccc cctccctctc   5280
ccccatcccc tatctttctc tctccctccc tgccacccac tccctctccc tctccctctc   5340
cctctccctc cctctctccc cacaccctgt ctttctttct ccctcccac  ctcccctctt   5400 ctcccacccc cggggtctgc gtggaggcca ctgctccgtc cctgctgagg attctgctgc   5460
actctggctc ctgcctgtgg gaatccgtcc tgtctctctg gctggtgtct ctctggctgg   5520
```

```
cgtccctgcc cagatgccgc agcttgatgg ggatgctctt tcattccttt atgctgcttg   5580
ggacaggtgc gctcccagaa gggatcctgt cgccagttct gggggagccc agccatgctc   5640
tcccctgcc caccccacag agccctctct ggaccttgtg ccagcaccct gctccagtga    5700
atctttcaac cctcttccca ttcaccaatt ctctcttcag tgctgtccac actggagttg   5760
gttctgacca cttttgtagt gttttttttcc acttaaatga ttgtattttt tacatccagg  5820
atttgtaatt tttaaaaata gatgcctgtt cattttactc cttagacaga agccaaatgt   5880
atttcctaac attttatcca tgctgtctct gtggatcctg cacatattta aacatagcct   5940
aagcgtacct gtttgctcgt tattttttatc tccctgagat ggatccatgg gtccactggc  6000
cctgttgatt ttctgagtcg tatttcttag tgtgtttggg ccatgcgagc ttggggatgt   6060
tgatttctag gtttgttggg gacagagggc tttctctttg tgctgtcagc cttgtgttct   6120
gggctccccc gtccccagct ctcctttcct tgtctaccag atttcagtgg ccttggccca   6180
gccccacagc cccagccag gactgtggcc tttcctggca gctgctgggg tcgtcctgtg    6240
ctctgaggtg cctccaggt cagggccggt cagctgagca gccccaggc tccagacggc    6300
acatgctgag gtcaccacag ccggctccac ccctgctcag gccgaggtcc cccagggagg   6360
ggcttgtccc tggtctggat cctaggggac actttgattc tctgctggcc acccccagag   6420
tcacacagct ccagggtcaa cccaaacatc cggacttcct ccgccccact cgtcagggga   6480
ggcattgatc ttcttttga cagggtct tgctcagtca cccaggctgg cgtgcagtgg     6540
tgtaatcaca gctcactgca gcctcaacct cctgggctca aatgatcctc ctgactcagc   6600
ctcctcagtg gctgggacta caggcgcccg ccaccacact ggctaatttt ttgtattttt   6660
tgtagacgg ggggtctcac catgttgccc aggctggtct tgaactcctg tcctcaggtg    6720
atccacccgc ctcggcctcc cacagtgctg ggatgacagg cttgagccac tgcacccagc   6780
cggagtatca ttttatgaa tgatttcaaa catgcagaaa aatacaaaaa caatatacga    6840
ggtacacacg tgcccatggc cttggaccca cagacgtcac cattcccagc ccaccttct    6900
ccatggacac ccctccctcc cctccccaa gtctcccctg ttctctctct gggccacagt    6960
gggggggttcc agggcctggg aggggctca aagctccgat gggactgggc agtgtcaggt   7020
ggctgcagcc cccatacgct atgcctctga cccgcccaca cccccaccg cggcttctcc    7080
tccgggctgc agggtgtgca gccccgccc gcagtccccc ctccttcgcc ctgtgtgact    7140
cctggggctc cgtgtgacca ctctgtgtgg tttgtgtgtt tgcttctctg cagccgcccc   7200
gtggggaggg tggtgtctct ctggccctgt gctgtgcccc cgcctgggtt tacagatgtc   7260
tgtcattgct gtgggggtga cggtccctgc gctggcctgg agagaggttc ggggccaacg   7320
ggcagcgggc accccggtga aagtccctcg aggctgcggt ggcgacacca cgtccagcca   7380
cttctcaggt cgtcctagcc aggtgccatt catcccaggc ggacaggggg ccgaccaccg   7440
gccccatctc tctccactgc cacctctccc tgtgtgtccc gggaggggcc gcccgctggg   7500
cctcggctcc ttacctggta gacgagggca gcagcactgc agggcaggct ctgagggggct 7560
tcagggagac gcaggtgctg gcctcagact ccaggatgct gcggccaggc caggcgccat   7620
ctgggtgcag gggcggccac agggcagctg tcgccatatc gacagcagcc gtccgtctgg   7680
gctcccgggg ccacctgccc gccgctcctt cctctcctgg cttatttcc aaacaatttg    7740
cttaacgtga ttcccggcca agctaaacat gactaatcgt gtttaccggg tgatcccgcg   7800
cctcctggca ggcggggctg gggcccagga ggaaggaatg cctgcatgtg ctggttcagg   7860
gactcaccac cctggcgtcc tcccttcttc tcttgcagag cctgacgcac cccagggctg   7920
```

-continued

```
ccgcc atg gag ccc ctg ttc cca gcc tcc acg ccc agc tgg aac gcc tcc    7970
      Met Glu Pro Leu Phe Pro Ala Ser Thr Pro Ser Trp Asn Ala Ser
      1               5                   10                  15 tcc ccg ggg gct gcc tct gga ggc ggt gac aac agg acg ctg gtg ggg      8018
Ser Pro Gly Ala Ala Ser Gly Gly Gly Asp Asn Arg Thr Leu Val Gly
                20                  25                  30 ccg gcg ccc tcg gca ggg gcc cgg gcg gtg ctg gtc ccc gtg ctg tac      8066
Pro Ala Pro Ser Ala Gly Ala Arg Ala Val Leu Val Pro Val Leu Tyr
            35                  40                  45 ctg ctg gtg tgt gcg gcc ggg ctg ggc ggg aac acg ctg gtc atc tac      8114
Leu Leu Val Cys Ala Ala Gly Leu Gly Gly Asn Thr Leu Val Ile Tyr
        50                  55                  60 gtg gtg ctg cgc ttc gcc aag atg aag acc gtc acc aac atc tac att      8162
Val Val Leu Arg Phe Ala Lys Met Lys Thr Val Thr Asn Ile Tyr Ile
    65                  70                  75 ctc aac ctg gca gtg gcc gac gtc ctg tac atg ctg ggg ctg cct ttc      8210
Leu Asn Leu Ala Val Ala Asp Val Leu Tyr Met Leu Gly Leu Pro Phe
80                  85                  90                  95 ctg gcc acg cag aac gcc gcg tcc ttc tgg ccc ttc ggc ccc gtc ctg      8258
Leu Ala Thr Gln Asn Ala Ala Ser Phe Trp Pro Phe Gly Pro Val Leu
                100                 105                 110 tgc cgc ctg gtc atg acg ctg gac ggc gtc aac cag ttc acc agt gtc      8306
Cys Arg Leu Val Met Thr Leu Asp Gly Val Asn Gln Phe Thr Ser Val
            115                 120                 125 ttc tgc ctg aca gtc atg agc gtg gac cgc tac ctg gca gtg gtg cac      8354
Phe Cys Leu Thr Val Met Ser Val Asp Arg Tyr Leu Ala Val Val His
        130                 135                 140 ccg ctg agc tcg gcc cgc tgg cgc cgc ccg cgt gtg gcc aag ctg gcg      8402
Pro Leu Ser Ser Ala Arg Trp Arg Arg Pro Arg Val Ala Lys Leu Ala
    145                 150                 155 agc gcc gcg gcc tgg gtc ctg tct ctg tgc atg tcg ctg ccg ctc ctg      8450
Ser Ala Ala Ala Trp Val Leu Ser Leu Cys Met Ser Leu Pro Leu Leu
160                 165                 170                 175 gtg ttc gcg gac gtg cag gag ggc ggt acc tgc aac gcc agc tgg ccg      8498
Val Phe Ala Asp Val Gln Glu Gly Gly Thr Cys Asn Ala Ser Trp Pro
                180                 185                 190 gag ccc gtg ggg ctg tgg ggc gcc gtc ttc atc atc tac acg gcc gtg      8546
Glu Pro Val Gly Leu Trp Gly Ala Val Phe Ile Ile Tyr Thr Ala Val
            195                 200                 205 ctg ggc ttc ttc gcg ccg ctg ctg gtc atc tgc ctg tgc tac ctg ctc      8594
Leu Gly Phe Phe Ala Pro Leu Leu Val Ile Cys Leu Cys Tyr Leu Leu
        210                 215                 220 atc gtg gtg aag gtg agg gcg gcg ggc gtg cgc gtg ggc tgc gtg cgg      8642
Ile Val Val Lys Val Arg Ala Ala Gly Val Arg Val Gly Cys Val Arg
    225                 230                 235 cgg cgc tcg gag cgg aag gtg acg cgc atg gtg ttg gtg gtg gtg ctg      8690
Arg Arg Ser Glu Arg Lys Val Thr Arg Met Val Leu Val Val Val Leu
240                 245                 250                 255 gtg ttt gcg gga tgt tgg ctg ccc ttc ttc acc gtc aac atc gtc aac      8738
Val Phe Ala Gly Cys Trp Leu Pro Phe Phe Thr Val Asn Ile Val Asn
                260                 265                 270 ctg gcc gtg gcg ctg ccc cag gag ccc gcc tcc gcc ggc ctc tac ttc      8786
Leu Ala Val Ala Leu Pro Gln Glu Pro Ala Ser Ala Gly Leu Tyr Phe
            275                 280                 285 ttc gtg gtc atc ctc tcc tac gcc aac agc tgt gcc aac ccc gtc ctc      8834
Phe Val Val Ile Leu Ser Tyr Ala Asn Ser Cys Ala Asn Pro Val Leu
        290                 295                 300 tac ggc ttc ctc tct gac aac ttc cgc cag agc ttc cag aag gtt ctg      8882
Tyr Gly Phe Leu Ser Asp Asn Phe Arg Gln Ser Phe Gln Lys Val Leu
```

```
                305              310                 315
tgc ctc cgc aag ggc tct ggt gcc aag gac gct gac gcc acg gag ccg    8930
Cys Leu Arg Lys Gly Ser Gly Ala Lys Asp Ala Asp Ala Thr Glu Pro
320                 325                 330                 335 cgt cca gac agg atc cgg cag cag cag gag gcc acg ccg ccc gcg cac    8978
Arg Pro Asp Arg Ile Arg Gln Gln Gln Glu Ala Thr Pro Pro Ala His
                340                 345                 350 cgc gcc gca gcc aac ggg ctt atg cag acc agc aag ctg tga            9020
Arg Ala Ala Ala Asn Gly Leu Met Gln Thr Ser Lys Leu
                355                 360 gagtgcaggc gggggtggg cggccccgtg tcaccccag gagcggaggt tgcactgcgg     9080 tgaccccac ccatgacctg ccagtcagga tgctccccgg cggtggtgtg aggacagagc    9140
tggctgaagc caggctgggg tagacacagg gcagtaggtt ccccaccgtg accgaccatc   9200
ccctctaacc gtctgccaca cagcgggggc tcccgggagg taggggaggt ggccagaccg   9260 gtgggggct ccgccatgcc gtgcaagtgc tcagggccgc ctcaccctcc atctggcccc    9320
agcccatgcc ggccttccct ctggggagcg acttttccag aaggccggcc aggcgagagg   9380
gtcttcctga cggcggagct gacctgcccg gccaccagc tgcatgtcag ctccgagcca    9440
ccgggtcccc gtccaaggct gctctgctaa gttaaagaca cccgaaagcg cttgactcag   9500
gtccccggag tcctggcca gggcccagc cctcgcttg ccctgcactg tgtggactct     9560
ggggatgcag gtgtaagggg agtgtggctg ggcagcccct ggtcagccag ggtcacgcct   9620
gtcctggggg ccccacccctg ctgcccgaca ccccccatgg gaggctgcgg gcggcagttg  9680
ctgtctcaga gagggagtg tgggggcttg gcgctggcc tagccagggg cgaggtgggg    9740
aggcggctgg tgcagaggag agctgggggc tgaggttggg gtgaaggctg cagccctcca   9800
ggctgctggg ggtgcagatg gctgtgccgt gctgagattg gctctgtctg gagggtcca   9860 gtgtggggtg cctgagggca ctagggagag gtgctcctgc tgcaggagga cctgagggtc   9920
agggcttgga gaggacaggg aacctgcggc cgtctcttct gctttgggc aggggctctg   9980 gcccgggaga ggaacggggg acaggagcag aggacggtca tccaggcgca gcgggagct    10040 gctccccagg ccacagcaga cagcactgct gagaggcagc ggccgcgcgg gtgacgcaaa   10100
tggcaggccc tgggaatccc gccgcctccc acctagaatt gtcctacctc ccccacccca   10160
aacaccagct tttcctggcg ccccaggccc agaacgtggg cccagagagc cttgctgggg   10220
tctctggggc accttggcct tgctctgagg ctggaaggag aaggaccagg gtgcggcatc    10280
actcggcctc agggacccct ctgccctgcc cagcactggc cccgacccgt gctcccgccg   10340
tctgcccaga gcaggacctc aacctcctgg agggcacagg gagcggctga gtgggcacaa   10400
atcctggcag gagaaaggcc caggctgagg ccaggcctgg gaaacatcca agcagtgagg   10460
acacgcgtgt ttgacaactg ctcccctgaa taaa                               10494

<210> SEQ ID NO 20
<211> LENGTH: 364
<212> TYPE: PRT
<213> ORGANISM: Homo sapiens

<400> SEQUENCE: 20

Met Glu Pro Leu Phe Pro Ala Ser Thr Pro Ser Trp Asn Ala Ser Ser
1               5                   10                  15

Pro Gly Ala Ala Ser Gly Gly Gly Asp Asn Arg Thr Leu Val Gly Pro
                20                  25                  30

Ala Pro Ser Ala Gly Ala Arg Ala Val Leu Val Pro Val Leu Tyr Leu
```

|  |  |  | 35 |  |  |  | 40 |  |  |  | 45 |  |  |  |

Leu Val Cys Ala Ala Gly Leu Gly Gly Asn Thr Leu Val Ile Tyr Val
 50                      55                      60

Val Leu Arg Phe Ala Lys Met Lys Thr Val Thr Asn Ile Tyr Ile Leu
 65                      70                      75                      80

Asn Leu Ala Val Ala Asp Val Leu Tyr Met Leu Gly Leu Pro Phe Leu
                         85                      90                      95

Ala Thr Gln Asn Ala Ala Ser Phe Trp Pro Phe Gly Pro Val Leu Cys
                        100                     105                     110

Arg Leu Val Met Thr Leu Asp Gly Val Asn Gln Phe Thr Ser Val Phe
                115                     120                     125

Cys Leu Thr Val Met Ser Val Asp Arg Tyr Leu Ala Val Val His Pro
130                     135                     140

Leu Ser Ser Ala Arg Trp Arg Pro Arg Val Ala Lys Leu Ala Ser
145                     150                     155                     160

Ala Ala Ala Trp Val Leu Ser Leu Cys Met Ser Leu Pro Leu Leu Val
                        165                     170                     175

Phe Ala Asp Val Gln Glu Gly Gly Thr Cys Asn Ala Ser Trp Pro Glu
                180                     185                     190

Pro Val Gly Leu Trp Gly Ala Val Phe Ile Ile Tyr Thr Ala Val Leu
                195                     200                     205

Gly Phe Phe Ala Pro Leu Leu Val Ile Cys Leu Cys Tyr Leu Leu Ile
210                     215                     220

Val Val Lys Val Arg Ala Ala Gly Val Arg Val Gly Cys Val Arg Arg
225                     230                     235                     240

Arg Ser Glu Arg Lys Val Thr Arg Met Val Leu Val Val Val Leu Val
                        245                     250                     255

Phe Ala Gly Cys Trp Leu Pro Phe Phe Thr Val Asn Ile Val Asn Leu
                260                     265                     270

Ala Val Ala Leu Pro Gln Glu Pro Ala Ser Ala Gly Leu Tyr Phe Phe
                275                     280                     285

Val Val Ile Leu Ser Tyr Ala Asn Ser Cys Ala Asn Pro Val Leu Tyr
290                     295                     300

Gly Phe Leu Ser Asp Asn Phe Arg Gln Ser Phe Gln Lys Val Leu Cys
305                     310                     315                     320

Leu Arg Lys Gly Ser Gly Ala Lys Asp Ala Asp Ala Thr Glu Pro Arg
                        325                     330                     335

Pro Asp Arg Ile Arg Gln Gln Gln Glu Ala Thr Pro Pro Ala His Arg
                340                     345                     350

Ala Ala Ala Asn Gly Leu Met Gln Thr Ser Lys Leu
        355                     360

<210> SEQ ID NO 21
<211> LENGTH: 1525
<212> TYPE: DNA
<213> ORGANISM: Mus musculus
<220> FEATURE:
<221> NAME/KEY: CDS
<222> LOCATION: (241)..(1329)

<400> SEQUENCE: 21
ccgagccacc catcctcctg tccctgcagg tggcttcttc ttcctctcta gcttgttttc      60
caaacaattt gcttaatgtg attcctggtc aagttgaaca tgactaaagg tgttttact     120 catcaccgtc tggcaggcgg gctccccacg acaggaggaa ggaatgcctg aatgtgccca    180

-continued

```
ctagtgacac cctcttctct tgcagagata catgtgctct ggcatcctga acctcacagc    240 atg gag ccc ctc tct ttg gct tcc aca cct agc tgg aat gcc tca gct     288
Met Glu Pro Leu Ser Leu Ala Ser Thr Pro Ser Trp Asn Ala Ser Ala
1               5                   10                  15 gct tcc agc ggt agc cat aac tgg tca cta gtg gac ccg gtg tca ccc     336
Ala Ser Ser Gly Ser His Asn Trp Ser Leu Val Asp Pro Val Ser Pro
            20                  25                  30 atg gga gcc cgg gcg gta tta gtg cct gtg ctc tac ttg ttg gta tgc     384
Met Gly Ala Arg Ala Val Leu Val Pro Val Leu Tyr Leu Leu Val Cys
        35                  40                  45 acc gtg gga ctg ggt gga aac aca ctg gtc atc tat gtg gtg ttg cgg    432
Thr Val Gly Leu Gly Gly Asn Thr Leu Val Ile Tyr Val Val Leu Arg
    50                  55                  60 tat gcc aag atg aag aca gtt act aat gtg tac atc ctg aac ctg gcc    480
Tyr Ala Lys Met Lys Thr Val Thr Asn Val Tyr Ile Leu Asn Leu Ala
65                  70                  75                  80 gtg gct gac gtg ttg ttt atg ttg ggg ctt cct ttc ctg gca acg cag    528
Val Ala Asp Val Leu Phe Met Leu Gly Leu Pro Phe Leu Ala Thr Gln
                85                  90                  95 aat gct gtc tcc tac tgg ccc ttt ggc tcc ttc ttg tgc cgc ctg gtc    576
Asn Ala Val Ser Tyr Trp Pro Phe Gly Ser Phe Leu Cys Arg Leu Val
            100                 105                 110 atg acg ctg gac ggt atc aac cag ttc acc agt atc ttc tgc ctg atg    624
Met Thr Leu Asp Gly Ile Asn Gln Phe Thr Ser Ile Phe Cys Leu Met
        115                 120                 125 gtc atg agt gtc gac cgc tac ctg gcc gtg gtc cac cct ctc cgc tca    672
Val Met Ser Val Asp Arg Tyr Leu Ala Val Val His Pro Leu Arg Ser
    130                 135                 140 gcc cgg tgg cgt cgc cca cgg gta gcc aag ctg gct agt gct gcc gtc    720
Ala Arg Trp Arg Arg Pro Arg Val Ala Lys Leu Ala Ser Ala Ala Val
145                 150                 155                 160 tgg gtc ttc tcg ctg ctc atg tct ctg ccg ctc ttg gtc ttt gcg gat    768
Trp Val Phe Ser Leu Leu Met Ser Leu Pro Leu Leu Val Phe Ala Asp
                165                 170                 175 gtc cag gaa ggc tgg ggc acc tgc aac ctg agc tgg cca gag cct gtg    816
Val Gln Glu Gly Trp Gly Thr Cys Asn Leu Ser Trp Pro Glu Pro Val
            180                 185                 190 gga ctg tgg ggt gca gcc ttc atc act tac aca tct gtg ctg ggc ttc    864
Gly Leu Trp Gly Ala Ala Phe Ile Thr Tyr Thr Ser Val Leu Gly Phe
        195                 200                 205 ttt ggg ccc ctg ctg gtc atc tgc ttg tgc tat ttg ctc atc gta gtg    912
Phe Gly Pro Leu Leu Val Ile Cys Leu Cys Tyr Leu Leu Ile Val Val
    210                 215                 220 aag gtg aag gct gca ggt atg cgt gtg ggc tcc tca cgg cgg agg cgc    960
Lys Val Lys Ala Ala Gly Met Arg Val Gly Ser Ser Arg Arg Arg Arg
225                 230                 235                 240 tca gaa cgc aag gtg act cgc atg gtg gtg gta gtg gtg ctg gtg ttc   1008
Ser Glu Arg Lys Val Thr Arg Met Val Val Val Val Val Leu Val Phe
                245                 250                 255 gtg ggc tgc tgg ctg cct ttc ttc atc gtc aac atc gtc aac ctg gcc   1056
Val Gly Cys Trp Leu Pro Phe Phe Ile Val Asn Ile Val Asn Leu Ala
            260                 265                 270 ttc acg cta ccc gag gag ccc acc tct gcc ggc ctc tac ttc ttt gtg   1104
Phe Thr Leu Pro Glu Glu Pro Thr Ser Ala Gly Leu Tyr Phe Phe Val
        275                 280                 285 gtg gtc ctg tct tat gcc aat agc tgt gcc aac ccc ctg cta ctg tgg   1152
Val Val Leu Ser Tyr Ala Asn Ser Cys Ala Asn Pro Leu Leu Leu Trp
    290                 295                 300 ctt ctc tct gat aac ttc gcg cag agt ttc cgg aag gct ctg tgc cta   1200
```

```
                    Leu Leu Ser Asp Asn Phe Arg Gln Ser Phe Arg Lys Ala Leu Cys Leu
                    305                 310                 315                 320 cgt aga gga tac ggt gtg gag gat gca gat gcc ata gag cca cgg cca       1248
Arg Arg Gly Tyr Gly Val Glu Asp Ala Asp Ala Ile Glu Pro Arg Pro
                    325                 330                 335 gac aag agt ggg cgg cca cag acc aca ctg ccc aca cgc agc tgt gag       1296
Asp Lys Ser Gly Arg Pro Gln Thr Thr Leu Pro Thr Arg Ser Cys Glu
                340                 345                 350 gcc aac ggg ctc atg cag acc agc agg ctt tga gtgtcccagt aacacctggg     1349
Ala Asn Gly Leu Met Gln Thr Ser Arg Leu
                355                 360 gggtcctgcg gggcctctgt ggtgttgtct tctgggatat gagagtttgc tgagatgcac     1409
tcgcccccag gcctataagt tggactcctc ttggtggcag tgtgaagaca gctgtctgcg     1469
gctaagccat gggtgactga tcatctctct caccaaaacg ttctgctaga ccaggg         1525

<210> SEQ ID NO 22
<211> LENGTH: 362
<212> TYPE: PRT
<213> ORGANISM: Mus musculus

<400> SEQUENCE: 22

Met Glu Pro Leu Ser Leu Ala Ser Thr Pro Ser Trp Asn Ala Ser Ala
1               5                   10                  15

Ala Ser Ser Gly Ser His Asn Trp Ser Leu Val Asp Pro Val Ser Pro
                20                  25                  30

Met Gly Ala Arg Ala Val Leu Val Pro Val Leu Tyr Leu Leu Val Cys
            35                  40                  45

Thr Val Gly Leu Gly Gly Asn Thr Leu Val Ile Tyr Val Val Leu Arg
        50                  55                  60

Tyr Ala Lys Met Lys Thr Val Thr Asn Val Tyr Ile Leu Asn Leu Ala
65                  70                  75                  80

Val Ala Asp Val Leu Phe Met Leu Gly Leu Pro Phe Leu Ala Thr Gln
                85                  90                  95

Asn Ala Val Ser Tyr Trp Pro Phe Gly Ser Phe Leu Cys Arg Leu Val
                100                 105                 110

Met Thr Leu Asp Gly Ile Asn Gln Phe Thr Ser Ile Phe Cys Leu Met
            115                 120                 125

Val Met Ser Val Asp Arg Tyr Leu Ala Val Val His Pro Leu Arg Ser
        130                 135                 140

Ala Arg Trp Arg Arg Pro Arg Val Ala Lys Leu Ala Ser Ala Ala Val
145                 150                 155                 160

Trp Val Phe Ser Leu Leu Met Ser Leu Pro Leu Leu Val Phe Ala Asp
                165                 170                 175

Val Gln Glu Gly Trp Gly Thr Cys Asn Leu Ser Trp Pro Glu Pro Val
                180                 185                 190

Gly Leu Trp Gly Ala Ala Phe Ile Thr Tyr Thr Ser Val Leu Gly Phe
            195                 200                 205

Phe Gly Pro Leu Leu Val Ile Cys Leu Cys Tyr Leu Leu Ile Val Val
        210                 215                 220

Lys Val Lys Ala Ala Gly Met Arg Val Gly Ser Ser Arg Arg Arg
225                 230                 235                 240

Ser Glu Arg Lys Val Thr Arg Met Val Val Val Val Leu Val Phe
                245                 250                 255

Val Gly Cys Trp Leu Pro Phe Phe Ile Val Asn Ile Val Asn Leu Ala
            260                 265                 270
```

-continued

```
Phe Thr Leu Pro Glu Glu Pro Thr Ser Ala Gly Leu Tyr Phe Phe Val
        275                 280                 285

Val Val Leu Ser Tyr Ala Asn Ser Cys Ala Asn Pro Leu Leu Leu Trp
    290                 295                 300

Leu Leu Ser Asp Asn Phe Arg Gln Ser Phe Arg Lys Ala Leu Cys Leu
305                 310                 315                 320

Arg Arg Gly Tyr Gly Val Glu Asp Ala Asp Ala Ile Glu Pro Arg Pro
                325                 330                 335

Asp Lys Ser Gly Arg Pro Gln Thr Thr Leu Pro Thr Arg Ser Cys Glu
                340                 345                 350

Ala Asn Gly Leu Met Gln Thr Ser Arg Leu
            355                 360
```